United States Patent
Kitamura et al.

(10) Patent No.: US 10,804,469 B2
(45) Date of Patent: Oct. 13, 2020

(54) CHARGE TRANSPORT MATERIAL, ORGANIC ELECTROLUMINESCENT ELEMENT, AND ILLUMINATION DEVICE, DISPLAY DEVICE, OR LIGHT-EMITTING DEVICE CHARACTERIZED BY USING SAID ELEMENT

(75) Inventors: Tetsu Kitamura, Kanagawa (JP); Kousuke Watanabe, Kanagawa (JP)

(73) Assignee: UDC IRELAND LIMITED, Dublin (IE)

( * ) Notice: Subject to any disclaimer, the term of this patent is extended or adjusted under 35 U.S.C. 154(b) by 886 days.

(21) Appl. No.: 14/008,347

(22) PCT Filed: Mar. 29, 2012

(86) PCT No.: PCT/JP2012/058362
§ 371 (c)(1),
(2), (4) Date: Feb. 7, 2014

(87) PCT Pub. No.: WO2012/133653
PCT Pub. Date: Oct. 4, 2012

(65) Prior Publication Data
US 2015/0069332 A1 Mar. 12, 2015

(30) Foreign Application Priority Data

Mar. 31, 2011 (JP) .................................. 2011-080216
Mar. 27, 2012 (JP) .................................. 2012-072477

(51) Int. Cl.
*H01L 51/00* (2006.01)
*C07D 409/04* (2006.01)
(Continued)

(52) U.S. Cl.
CPC ........ *H01L 51/0054* (2013.01); *C07D 307/91* (2013.01); *C07D 333/76* (2013.01); *C07D 405/14* (2013.01); *C07D 409/04* (2013.01); *C09B 1/00* (2013.01); *C09B 3/78* (2013.01); *C09B 23/141* (2013.01); *C09B 57/00* (2013.01); *C09B 57/001* (2013.01); *C09B 57/008* (2013.01); *C09B 69/008* (2013.01); *H01L 51/0052* (2013.01); *H01L 51/0067* (2013.01); *H01L 51/0073* (2013.01); (Continued)

(58) Field of Classification Search
CPC .. C07D 307/91; C07D 405/14; C07D 409/04; C07D 333/76; H01L 51/0073; H01L 51/0074; H01L 51/0054; H01L 51/0067; H01L 51/0094; H01L 51/5056; H01L 51/0052; H01L 2251/5361; H01L 51/0072; H01L 51/5016; H01L 51/5096; H01L 51/5072; H01L 51/5048; H01L 51/5203; C09B 57/001; C09B 3/78; C09B 57/00; C09B 57/008; C09B 23/141; C09B 1/00; C09B 69/008
See application file for complete search history.

(56) References Cited

U.S. PATENT DOCUMENTS 7,279,232 B2 * 10/2007 Knowles ............. C07F 15/0033
257/E51.044
7,279,704 B2 * 10/2007 Walters .................. C09K 11/06
257/40
(Continued)

FOREIGN PATENT DOCUMENTS

| JP | 2009099783 | 5/2009 |
|---|---|---|
| JP | 2010535809 | 11/2010 |
| WO | 2007142083 | 12/2007 |
| WO | 2009/021107 | 2/2009 |
| WO | 2010/074087 | 1/2010 |

OTHER PUBLICATIONS

Di et al, The Influence of Molecular Structure on Collision Radium for Optical Sensing of Molecular Oxygen Based on Cyclometalatd Ir(III) Complexes, RSC Advances, Issue 71, 2018, pp. 41040-41047.*

*Primary Examiner* — Alexander C Kollias
(74) *Attorney, Agent, or Firm* — Riverside Law LLP

(57) ABSTRACT

[This] charge transport material which comprises a compound expressed by the following formula has a high efficiency and drive durability after high-temperature storage and resists the occurrence of dark spots ($X^{101}$ represents a sulfur atom or an oxygen atom; $R^{101}$ and $R^{102}$ represent each independently an alkyl group, an aryl group, a heteroaryl group, a fluorine atom, or a silyl group, and may further be substituted with these groups; n101 represents an integer from 0 to 11; n102 represents an integer from 0 to 7; a plurality of $R^{101}$ and $R^{102}$ [groups] may be the same or different; and $L^{101}$ represents a single bond or a divalent linking group; however, one of $R^{101}$, $L^{101}$, and $R^{102}$ includes a fluorine atom, a fluoroalkyl group, a cycloalkyl group, a cycloalkylene group, a silyl group, an alkylsilyl group, an arylsilyl group, or a silicon atom linking group.)

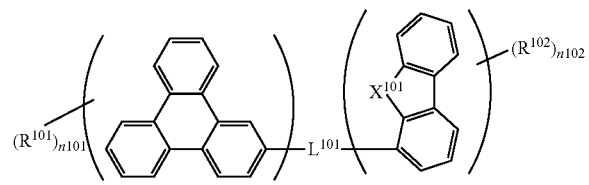

17 Claims, 1 Drawing Sheet

(51) Int. Cl.
*C07D 405/14* (2006.01)
*C07D 307/91* (2006.01)
*C07D 333/76* (2006.01)
*C09B 57/00* (2006.01)
*C09B 3/78* (2006.01)
*C09B 23/14* (2006.01)
*C09B 1/00* (2006.01)
*C09B 69/00* (2006.01)
*H01L 51/50* (2006.01)

(52) U.S. Cl.
CPC ...... *H01L 51/0074* (2013.01); *H01L 51/0094* (2013.01); *H01L 51/5056* (2013.01); *H01L 51/0072* (2013.01); *H01L 51/5016* (2013.01); *H01L 51/5072* (2013.01); *H01L 51/5096* (2013.01); *H01L 2251/5361* (2013.01)

(56) References Cited

U.S. PATENT DOCUMENTS

| | | | |
|---|---|---|---|
| 2006/0280965 A1 | 12/2006 | Kwong et al. | |
| 2007/0141387 A1* | 6/2007 | Nakano | C09K 11/06 428/690 |
| 2009/0030202 A1* | 1/2009 | Iwakuma | C07D 333/76 544/251 |
| 2010/0237334 A1* | 9/2010 | Ma | C07D 307/91 257/40 |
| 2010/0295030 A1* | 11/2010 | Kawamura | C07C 15/38 257/40 |

\* cited by examiner

CHARGE TRANSPORT MATERIAL, ORGANIC ELECTROLUMINESCENT ELEMENT, AND ILLUMINATION DEVICE, DISPLAY DEVICE, OR LIGHT-EMITTING DEVICE CHARACTERIZED BY USING SAID ELEMENT

CROSS-REFERENCE TO RELATED APPLICATIONS

The present application is a U.S. National Stage Entry of International Patent Application No. PCT/JP2012/058362, filed 29 Mar. 2012, which in turn claims priority benefit from Japanese Patent Application Nos. 2011-080216, filed 31 Mar. 2011; and 2012-072477, filed 27 Mar. 2012, all of which are hereby incorporated by reference in their entireties.

TECHNICAL FIELD

The present invention relates to a charge transport material, an organic electroluminescent element, and an illumination device, display device, or light-emitting device characterized by using this element.

BACKGROUND ART

Organic electroluminescent elements (hereinafter also referred to as "elements" or "organic EL elements") emit light at high brightness and at a low drive voltage and have therefore been the subject of active research and development. An organic electroluminescent element has an organic layer between a pair of electrodes. Electrons injected from the cathode and holes injected from the anode are rebound at the organic layer, and the energy of the excitons thus produced is utilized to emit light.

The efficiency of elements has been on the rise in recent years through the use of iridium (Ir) complexes, platinum (Pt) complexes, and other such phosphorescent materials. Furthermore, doped elements featuring a light-emitting layer in which a host material has been doped with a light-emitting material have been widely employed.

A great deal of development has also gone into charge transport materials contained in the host materials used in light-emitting layers and other such organic layers.

For example, Patent Document 1 discloses an organic electroluminescent element that makes use of a compound having a triphenylene structure, and describes organic electroluminescent elements that make use of a compound in which dibenzothiophene and triphenylene are linked with a benzene ring. Moreover, Patent Document 2 discloses an organic electroluminescent element that makes use of a compound in which dibenzofuran and triphenylene are linked with a naphthalene ring.

Various types of display device, including organic electroluminescent elements, have been widely used in recent years, and these need to be capable of stable operation over an extended period under various environments. For example, in automotive applications, not only does [the device] need to have a long service light (so-called durability), it also needs to have characteristics that will not change after storage at high temperature since an automobile interior can become quite hot when parked or driven in sunshine. In addition, such a lack of change in characteristics after storage at high temperature is also considered important because organic electroluminescent elements generate as much or more heat during their drive as a conventional light-emitting device.

RELATED ART DOCUMENTS

Patent Documents

Patent Document 1: Japanese Translation of PCT International Application 2010-535809
Patent Document 2: International Laid-Open WO 2009/074087

SUMMARY OF THE INVENTION

Problems to be Solved by the Invention

The present inventors studied the characteristics of organic electroluminescent elements featuring the compounds described in Patent Documents 1 and 2, and as a result, found that in addition to inadequate durability and efficiency after high-temperature storage, there is a new problem in that the occurrence of dark spots has been confirmed.

The problem to be solved by the present invention is to provide a charge transport material and an organic electroluminescent element with which drive durability and efficiency after high-temperature storage are high, and few dark spots are generated.

Means for Solving the Problems

As a result of diligent study, the present inventors discovered that a charge transport material and an organic electroluminescent element with which drive durability and efficiency after high-temperature storage are high and few dark spots are generated can be provided by a compound that includes a triphenylene structure and a dibenzothiophene structure or a dibenzofuran structure having a specific substituent.

Specifically, the present invention can be achieved by the following means:

(1) A charge transport material comprising a compound expressed by General Formula $1^1$ below:

[1] Translator's note: In the Japanese original document, the labeling number for each of the general formulas is indicated in parentheses, but we have omitted the parentheses in the translation to avoid confusion with other parenthetical notations.

[First Chemical Formula]

General Formula 1

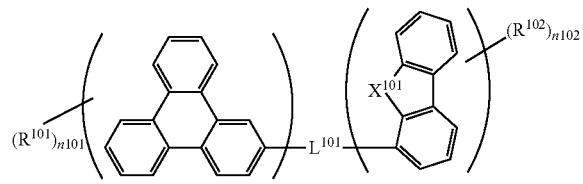

(in General Formula 1, $X^{101}$ represents a sulfur atom or an oxygen atom; $R^{101}$ and $R^{102}$ represent each independently an alkyl group, an aryl group, a heteroaryl group, a fluorine atom, or a silyl group, and may further be substituted with these groups; n101 represents an integer from 0 to 11; n102 represents an integer from 0 to 7; a plurality of $R^{101}$ and $R^{102}$ [groups] may be the same or different; and $L^{101}$ represents a single bond or a divalent linking group; however, one of $R^{101}$, $L^{101}$, and $R^{102}$ includes a fluorine atom, a fluoroalkyl group, a cycloalkyl group, a cycloalkylene group, a silyl group, an alkylsilyl group, an arylsilyl group, or a silicon atom linking group.)

(2) The charge transport material according to (1), wherein the compound expressed by General Formula 1 above is expressed by General Formula 2 below:

[Second Chemical Formula]

General Formula 2

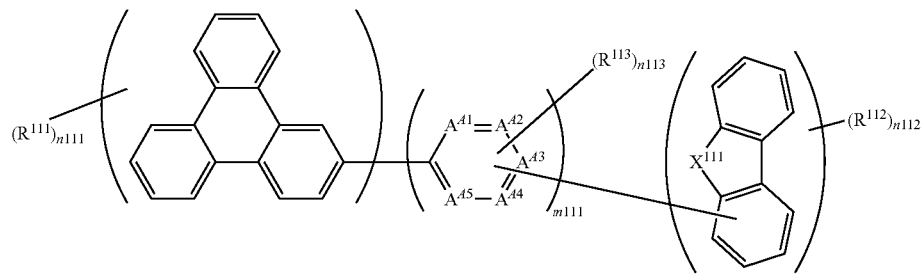

(in General Formula 2, $X^{111}$ represents a sulfur atom or an oxygen atom; $R^{111}$, $R^{112}$, and $R^{113}$ represent each independently an alkyl group, an aryl group, a heteroaryl group, a fluorine atom, or a silyl group, and may further be substituted with these groups; n111 represents an integer from 0 to 11; n112 represents an integer from 0 to 7; n113 represents an integer from 0 to 4; a plurality of $R^{111}$, $R^{112}$, and $R^{113}$ [groups] may be the same or different; $A^{41}$ to $A^{45}$ represent each independently CH (the hydrogen atom of the CH may be substituted with $R^{113}$) or a nitrogen atom; m111 represents an integer from 0 to 6; however, one of $R^{111}$, $R^{112}$, and $R^{113}$ includes a fluorine atom, a fluoroalkyl group, a cycloalkyl group, a silyl group, an alkylsilyl group, or an arylsilyl group; and n111, n112, and n113 will not be 0 at the same time.)

(3) The charge transport material according to (2), wherein m111 in General Formula 2 above is from 1 to 5.

(4) The charge transport material according to any one of (1) to (3), wherein the compound expressed by General Formula 1 above is expressed by General Formula 3 below:

fluorine atom, or a silyl group, and may further be substituted with these groups; n121 represents an integer from 0 to 11; n122 represents an integer from 0 to 7; n123 represents an integer from 0 to 4; a plurality of $R^{121}$, $R^{122}$, and $R^{123}$ [groups] may be the same or different; m121 represents an integer from 0 to 6; however, one of $R^{121}$, $R^{122}$, and $R^{123}$ includes a fluorine atom, a fluoroalkyl group, a cycloalkyl group, a silyl group, an alkylsilyl group, or an arylsilyl group; and n121, n122, and n123 will not be 0 at the same time.)

(5) The charge transport material according to any one of (1) to (4), wherein n101 in General Formula 1 above is 0.

(6) The charge transport material according to any one of (1) to (5), wherein n102 in General Formula 1 above is an integer from 0 to 2.

(7) The charge transport material according to any one of (1) to (6), wherein the compound expressed by General Formula 1 above is composed of only carbon atoms and hydrogen atoms, excluding the oxygen atoms and sulfur atoms in the dibenzothiophene skeleton and the dibenzofuran skeleton.

(8) The charge transport material according to any one of (1) to (7), wherein the compound expressed by General Formula 1 above includes a cycloalkyl group.

(9) The charge transport material according to any one of (1) to (8), wherein the molecular weight of the compound expressed by General Formula 1 is 1200 or less.

[Third Chemical Formula]

General Formula 3

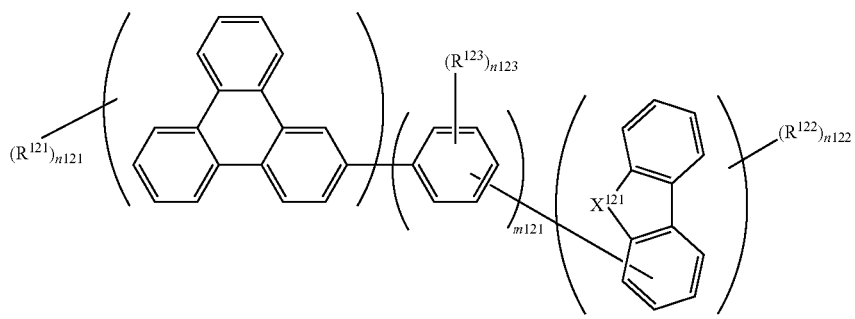

(in General Formula 3, $X^{121}$ represents a sulfur atom or an oxygen atom; $R^{121}$, $R^{122}$, and $R^{123}$ represent each independently an alkyl group, an aryl group, a heteroaryl group, a

(10) An organic electroluminescent element having a substrate, a pair of electrodes that are disposed on this substrate and that include an anode and a cathode, and an organic layer disposed between these electrodes, wherein the aforementioned organic layer includes a phosphorescent material and the charge transport material according to any one of (1) to (9).

(11) The organic electroluminescent element according to (10), wherein the aforementioned phosphorescent material is expressed by General Formula E-1 below:

[Fourth Chemical Formula]

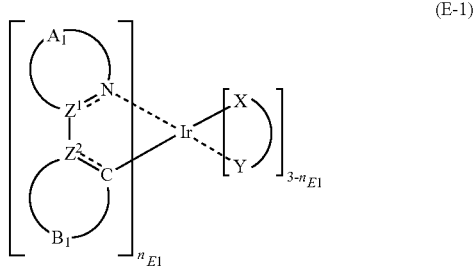

(E-1)

(in General Formula E-1, $Z^1$ and $Z^2$ represent each independently a carbon atom or a nitrogen atom; $A_1$ represents a group of atoms forming a five- or six-membered heterocycle together with $Z^1$ and the nitrogen atom; $B_1$ represents a group of atoms forming a five- or six-membered ring together with $Z^2$ and the carbon atom; (X—Y) represents a monoanionic bidentate ligand; and $n_{E1}$ represents an integer from 1 to 3.)

(12) The organic electroluminescent element according to (11), wherein the phosphorescent material expressed by General Formula E-1 above is expressed by General Formula E-2 below:

[Fifth Chemical Formula]

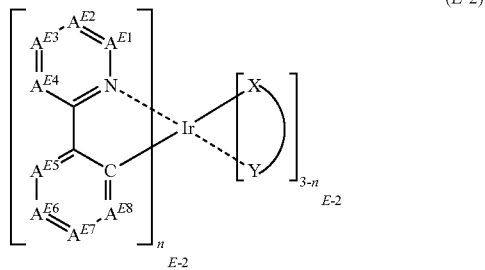

(E-2)

(in General Formula E-2, $A^{E1}$ to $A^{E8}$ represent each independently a nitrogen atom or a carbon atom substituted with $R^E$; $R^E$ represents a hydrogen atom or a substituent; (X—Y) represents a monoanionic bidentate ligand; and $n_{E2}$ represents an integer from 1 to 3.)

(13) The organic electroluminescent element according to (11) or (12), wherein the maximum emission wavelength of the phosphorescent material expressed by General Formula E-1 above is from 500 to 700 nm.

(14) The organic electroluminescent element according to any one of (10) to (13), wherein
the aforementioned organic layer includes a light-emitting layer containing the aforementioned phosphorescent material and other organic layers, and
the aforementioned light-emitting layer includes a compound expressed by General Formula 1 above.

(15) The organic electroluminescent element according to any one of (10) to (14), wherein
the aforementioned organic layer includes a light-emitting layer containing the aforementioned phosphorescent material and other organic layers,
these other organic layers include a hole blocking layer disposed between the aforementioned light-emitting layer and the aforementioned cathode, and this hole blocking layer contains a compound expressed by General Formula 1 above.

(16) A light-emitting device, display device, or illumination device characterized by using the organic electroluminescent element according to any one of (10) to (15).

Effects of the Invention

By using the compound expressed by General Formula 1 in the present invention, it is possible to provide a charge transport material and an organic electroluminescent element with which drive durability and efficiency after high-temperature storage are high, and dark spots tend not to be generated.

DETAILED DESCRIPTION OF EMBODIMENTS

Figure 1:
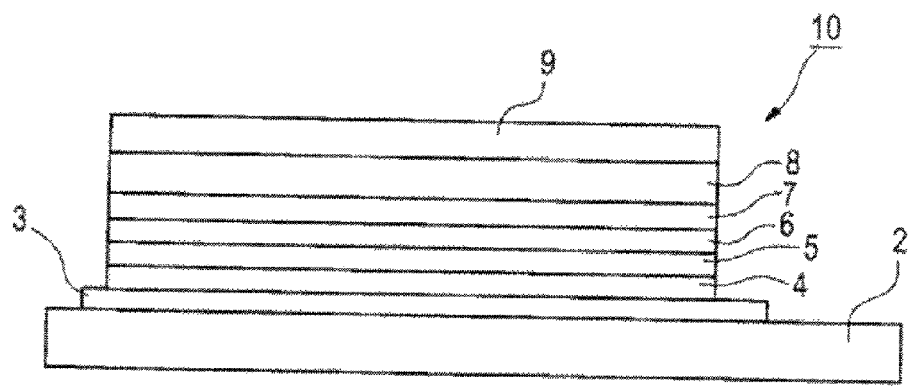
FIG. 1 is a schematic diagram illustrating one example of the configuration of the organic electroluminescent element according to the present invention.

The content of the present invention will be described in detail below. The description of the constituent elements mentioned below may be based on typical embodiments of the present invention, but the present invention is in no way limited to such embodiments. Note that "from . . . to . . . " in the Specification of the present application is used to mean that the numerical values given are included as the minimum value and maximum value, respectively.

Charge Transport Material

The charge transport material of the present invention is characterized by comprising a compound expressed by General Formula 1 below:

[Sixth Chemical Formula]

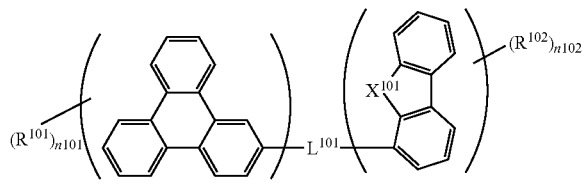

General Formula 1

(in General Formula 1, $X^{101}$ represents a sulfur atom or an oxygen atom; $R^{101}$ and $R^{102}$ represent each independently an alkyl group, an aryl group, a heteroaryl group, a fluorine atom, or a silyl group, and may further be substituted with these groups; n101 represents an integer from 0 to 11; n102 represents an integer from 0 to 7; a plurality of $R^{101}$ and $R^{102}$ [groups] may be the same or different; and $L^{101}$ represents a single bond or a divalent linking group; however, one of $R^{101}$, $L^{101}$, and $R^{102}$ includes a fluorine atom, a fluoroalkyl group, a cycloalkyl group, a cycloalkylene group, a silyl group, an alkylsilyl group, an arylsilyl group, or a silicon atom linking group.)

Although this does not adhere to any theory, because the charge transport material of the present invention has such a constitution, it is possible to adequately suppress intermolecular interaction by introducing a fluorine atom, a fluoroalkyl group, a cycloalkyl group, a cycloalkylene group, a silyl group, an alkylsilyl group, an arylsilyl group, or a silicon atom linking group. As a result, a good quality film can be obtained, and occurrence of dark spots can be suppressed. Furthermore, the investigation on the part of the present inventors resulted in [the discovery] that these substituents can increase the Tg of the organic film without sacrificing the drive durability and efficiency of the element. Accordingly, an organic electroluminescent element that uses the charge transport material of the present invention is also superior in terms of drive durability and efficiency after high-temperature storage.

The charge transport material of the present invention expressed by General Formula 1 above can be used favorably in electrophotography, organic transistors, organic opto-electric conversion elements (energy conversion applications, sensor applications, etc.), organic electroluminescent elements, and other such organic electronics elements, and can be used especially favorably in an organic electroluminescent element.

The charge transport material of the present invention can also be used in a thin film containing the compound expressed by General Formula 1 above. This thin film can be formed by using the aforementioned composition by vapor deposition, sputtering, or another such dry film formation method, or by transfer, printing, or another such wet film formation method. The thickness of the thin film may be any thickness depending on the application, but it is preferably 0.1 nm to 1 mm, more preferably 0.5 nm to 1 µm, even more preferably 1 nm to 200 nm, and especially preferably 1 nm to 100 nm.

Preferred ranges of the charge transport material composed of the compound expressed by General Formula 1 above will be described below.

Note that in the present invention, the hydrogen atom (H) in the description of General Formula 1 above also includes isotopes (deuterium atoms (D)), and the atoms that constitute the substituents also include isotopes thereof.

In the present invention, when the term "substituent" is used, that substituent may be substituted. For example, when "alkyl group" is referred to in the present invention, it encompasses alkyl groups that have been substituted with a fluorine atom (such as a trifluoromethyl group), alkyl groups that have been substituted with an aryl group (such as a triphenylmethyl group), and so forth, and when the term "$C_1$ to $C_6$ alkyl group" is used, this indicates that the carbon number is from 1 to 6 for the entire group, including one that has been substituted.

In the present invention, a fluorine atom, fluoroalkyl group, cycloalkyl group, cycloalkylene group, silyl group, alkylsilyl group, arylsilyl group, or silicon atom linking group are also referred to as "specific substituent."

However, in this Specification, "cycloalkylene group" means a collective term for 1,4-cyclohexanediyl, 1,3-cyclohexanediyl, 1,2-cyclohexanediyl, cyclopentane, and the like and does not refer to a ring in which one hydrogen atom is removed from cycloalkene.

In General Formula 1 above, $X^{101}$ represents an oxygen atom or a sulfur atom. A sulfur atom, which has a large van der Waals radius, is preferable from the standpoint of increasing electron mobility.

In General Formula 1 above, $R^{101}$ and $R^{102}$ represent each independently an alkyl group, an aryl group, a heteroaryl group, a fluorine atom, or a silyl group and may further be substituted with these groups.

If the aforementioned $R^{101}$ and $R^{102}$ are alkyl groups, these alkyl groups may be in the form of a straight-chain, branched, or cyclic and are alkyl groups generally with a carbon number of 1 to 30, preferably with a carbon number of 1 to 20, more preferably with a carbon number of 1 to 10, even more preferably with a carbon number of 1 to 6, and most preferably with a carbon number of 1 to 4. Examples include a methyl group, ethyl group, n-propyl group, isopropyl group, n-butyl group, isobutyl group, sec-butyl group, t-butyl group, n-pentyl group, isopentyl group, neopentyl group, n-hexyl group, n-octyl group, n-decyl group, n-hexadecyl group, cyclopropyl group, cyclopentyl group, and cyclohexyl group, with a methyl group, ethyl group, n-propyl group, n-butyl group, t-butyl group, cyclopentyl group, and cyclohexyl group being preferable, a methyl group, t-butyl group, cyclopentyl group, or cyclohexyl group being more preferable, a cyclopentyl group and cyclohexyl group being especially preferable, and a cyclohexyl group being most preferable.

The alkyl groups as the aforementioned $R^{101}$ and $R^{102}$ may further have an alkyl group, an aryl group, a heteroaryl group, a fluorine atom, or a silyl group as a substituent. Of these, substitution with a fluorine atom is preferable, and it is more preferable for all of the hydrogen atoms to be substituted with a fluorine atom to form a perfluoroalkyl group and especially preferable to form a trifloromethyl group.

If the aforementioned $R^{101}$ and $R^{102}$ are silyl groups, these silyl groups are preferably substituted, and the substituent is preferably an alkyl group or an aryl group. If the silyl groups as the aforementioned $R^{101}$ and $R^{102}$ are substituted with an alkyl group or an aryl group, it is more preferable if all of the hydrogen atoms are substituted with an alkyl group or an aryl group, forming a trialkylsilyl group or a triarylsilyl group, and it is especially favorable to form a trimethylsilyl group or a triphenylsilyl group.

If the aforementioned $R^{101}$ and $R^{102}$ are a heteroaryl group, a five- or six-membered heterocycle containing a nitrogen atom is preferable as this heteroaryl group. Examples of the aforementioned five- or six-membered heterocycle containing a nitrogen atom include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring. Of these, if the charge transport material of the present invention is used in an organic electroluminescent element, from the standpoints of stability, control of emission wavelength, and luminescent quantum yield, it is more preferably a pyridine ring, a pyrazine ring, an imidazole ring, or a pyrazole ring, with a pyridine ring, an imidazole ring, or a pyrazine ring being especially favorable, a pyridine ring or an imidazole ring being even more favorable, and a pyridine ring being most favorable.

If the aforementioned $R^{101}$ and $R^{102}$ are an aryl group, preferably with a carbon number of 6 to 30, more preferably with a carbon number of 6 to 20, and especially preferably with a carbon number of 6 to 12; examples include phenyl, naphthyl, and anthryl. The aforementioned $R^{101}$ is preferably a monocyclic aryl group and more preferably a phenyl group. Meanwhile, the aforementioned $R^{102}$ may be either a monocyclic aryl group or an aryl group having a condensed ring, and if it is a monocyclic aryl group, a phenyl group is preferable, and if it is an aryl group having a condensed ring, a triphenylene group is preferable. Note that a triphenylene group in the case of the aforementioned $R^{102}$ may have a further substituent, and preferred ranges thereof are the same as the preferred ranges of the aforementioned $R^{101}$.

The aryl groups or heteroaryl groups as the aforementioned $R^{101}$ and $R^{102}$ may further have an alkyl group, an aryl group, a heteroaryl group, a fluorine atom, or a silyl group as a substituent.

If the aryl groups or heteroaryl groups as the aforementioned $R^{101}$ and $R^{102}$ are substituted with an alkyl group, a fluorine atom, or a silyl group, the preferred ranges of the alkyl group, heteroaryl group, fluorine atom, or silyl group as the substituent are the same as when $R^{101}$ and $R^{102}$ are an alkyl group, a heteroaryl group, a fluorine atom, or a silyl group. If the aryl groups or heteroaryl groups as the aforementioned $R^{101}$ and $R^{102}$ are substituted with a heteroaryl group, a fluorine atom, or a silyl group, the number of these substituents is preferably from one to three per aryl group or heteroaryl group as the aforementioned $R^{101}$ and $R^{102}$, and more preferably one or two, with one being especially favorable.

If the aryl groups or heteroaryl groups as the aforementioned $R^{101}$ and $R^{102}$ are substituted with an aryl group or a heteroaryl group, the aryl group and arylene group, or the heteroaryl group and heteroarylene group, formed by substitution are preferably both monocycles, and more preferably are both 6-membered monocycles.

If the aryl groups or heteroaryl groups as the aforementioned $R^{101}$ and $R^{102}$ are substituted with an aryl group or a heteroaryl group, and the aryl group and arylene group, or the heteroaryl group and heteroarylene group, which are six-membered monocycles, or the linking groups and substituents of these, are combined and linked together, then these six-membered monocycles are preferably a plurality of univalent substituents linked by single bonds (the number of six-membered monocycles linked by single bonds is preferably three or fewer and more preferably one or two). Examples of preferred structures when an aryl group and an arylene group (six-membered monocycles) form a linking substituent include a phenyl group, a biphenyl group, a terphenyl group, a quaterphenyl group, and a quinquephenyl group. Of these, a phenyl group, a biphenyl group, or a terphenyl group (and especially a 3,5-diphenylphenyl) is preferable, a phenyl group or a biphenyl group is more preferable, and a phenyl group is most preferable. The aforementioned examples are the same structures when a heteroaryl group and a heteroarylene group are linked together.

First, the aforementioned $R^{101}$ here is especially preferably the following linking substituent ($R^{101}$):

[Seventh Chemical Formula]

General Formula 4: linking substituent ($R^{101}$)

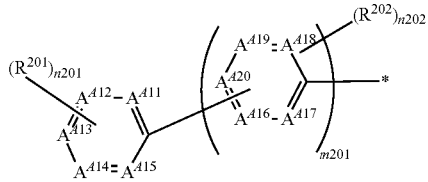

(In the above formula, $A^{411}$ to $A^{420}$ represent each independently CH (the hydrogen atom of the CH may be substituted) or a nitrogen atom, and m201 represents an integer from 0 to 2. However, the aryl group and arylene group, or the heteroaryl group and heteroarylene group, which are six-membered monocycles expressed by $A^{411}$ to $A^{420}$ do not have an aryl group or a heteroaryl group as a further substituent. $R^{201}$ and $R^{202}$ represent each independently an alkyl group, a fluorine atom, or a silyl group. n201 represents an integer from 0 to 5. n202 represents an integer from 0 to 4. The asterisk indicates the bonding position to the triphenylene ring.)

In the linking substituent ($R^{101}$), the preferred ranges of the aryl group and arylene group, or the heteroaryl group and heteroarylene group, which are six-membered monocycles expressed by $A^{11}$ to $A^{420}$, or a combination of these groups, are the same as the preferred ranges for the aryl groups or heteroaryl groups as $R^{101}$ and $R^{102}$ in General Formula 1 above, except that there is no aryl group or heteroaryl group as a further substituent.

In the linking substituent ($R^{101}$), the preferred ranges of $R^{201}$ and $R^{202}$ are the same as the preferred ranges for the alkyl group, the fluorine atom, and the silyl group as $R^{101}$ and $R^{102}$ in General Formula 1 above.

In the linking substituent ($R^{101}$), the preferred range of m201 is 0 or 1, with 0 being more preferable.

In the linking substituent ($R^{101}$), the preferred ranges of n201 and n202 when $R^{201}$ and $R^{202}$ are alkyl groups or silyl groups are each independently 0 to 2 and more preferably 0 or 1. The preferred ranges of n201 and n202 when $R^{201}$ and $R^{202}$ are fluorine atoms are each independently 0 to 3, and more preferably 0 to 2, with 0 or 1 being especially favorable. The preferred range for the total of n201 and n202 is the same as the preferred range for n101.

When m201 in the aforementioned linking substituent ($R^{101}$) is 2 or more, the repeating units expressed by m201 may be the same as or different from each other.

$R^{101}$ in General Formula 1 above may include any of a fluorine atom, a fluoroalkyl group, a cycloalkyl group, a cycloalkylene group, a silyl group, an alkylsilyl group, an arylsilyl group, or a silicon atom linking group (the aforementioned specific substituent), but in the present invention, a preferable mode is one in which $R^{101}$ in General Formula 1 above includes a fluorine atom, a fluoroalkyl group, or an alkylsilyl group, and a mode in which none of these specific substituents is included is more preferable.

Next, the aforementioned $R^{102}$ is especially favorably the following linking substituent ($R^{102}$):

[Eighth Chemical Formula]

General Formula 5: linking substituent ($R^{102}$)

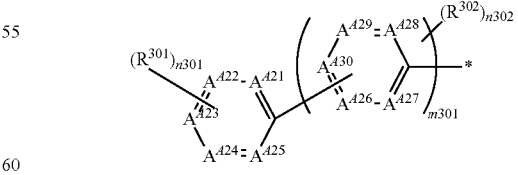

(In the above formula, $A^{421}$ to $A^{430}$ represent each independently CH (the hydrogen atom of the CH may be substituted) or a nitrogen atom, and m301 represents an integer from 0 to 3. However, the aryl group and arylene group, or the heteroaryl group and heteroarylene group, which are six-membered monocycles expressed by $A^{421}$ to $A^{430}$ do not have an aryl group or a heteroaryl group as a further substituent. $R^{301}$ and $R^{302}$ represent each independently an alkyl group, a fluorine atom, or a silyl group. n301 represents an integer from 0 to 5. n302 represents an integer from 0 to 4. The asterisk indicates the bonding position to the dibenzothiophene or dibenzofuran structure.)

In the linking substituent ($R^{102}$), the preferred ranges of the aryl group and arylene group, or the heteroaryl group and heteroarylene group, which are six-membered monocycles expressed by $A^{421}$ to $A^{430}$, are the same as the preferred ranges for the aryl groups or heteroaryl groups as $R^{101}$ and $R^{102}$ in General Formula 1 above, except that there is no aryl group or heteroaryl group as a further substituent.

In the linking substituent ($R^{102}$), the preferred ranges of $R^{301}$ and $R^{302}$ are the same as the preferred ranges for the alkyl group, the fluorine atom, and the silyl group as $R^{101}$ and $R^{102}$ in General Formula 1 above.

In the linking substituent ($R^{102}$), the preferred range of m301 is an integer from 0 to 2, and more preferably 0 or 1, with 0 being especially preferable.

In the linking substituent ($R^{102}$), the preferred ranges of n301 and n302 when $R^{301}$ and $R^{302}$ are alkyl groups or silyl groups are each independently 0 to 2 and more preferably 0 or 1. The preferred ranges of n301 and n302 when $R^{301}$ and $R^{302}$ are fluorine atoms are each independently 0 to 3, and more preferably 0 to 2, with 0 or 1 being especially favorable. The preferred range for the total of n301 and n302 is the same as the preferred range for n102.

When m301 in the aforementioned linking substituent ($R^{102}$) is 2 or more, the repeating units expressed by m301 may be the same as or different from each other. It is especially favorable for the repeating units expressed by m301 to be different from each other, in which case it is more preferable for a heteroarylene group and an arylene group to be bonded in that order, starting from the bonding position to the dibenzothiophene or dibenzofuran structure.

$R^{102}$ in General Formula 1 above may include a fluorine atom, a fluoroalkyl group, a cycloalkyl group, a cycloalkylene group, a silyl group, an alkylsilyl group, an arylsilyl group, or a silicon atom linking group (the aforementioned specific substituent), but in the present invention, a preferable mode is one in which $R^{102}$ in General Formula 1 above includes a fluorine atom, a fluoroalkyl group, a cycloalkyl group, or an alkylsilyl group, a more preferable mode is one in which a cycloalkyl group, an alkylsilyl group, or an arylsilyl group is included, and a especially preferable mode is one in which a cycloalkyl group is included.

In the aforementioned linking substituent ($R^{101}$) and the aforementioned linking substituent ($R^{102}$), the number of the aforementioned six-membered monocycles linked at the para position is preferably three or fewer. For example, when another six-membered monocycle is linked to the terminal of a p-terphenylene group, it is preferably linked at the meta position or the ortho position and more preferably linked at the meta position.

Note that the preferred range of the number of the aforementioned six-membered monocycles linked at the para position is the same for $L^{101}$ described below.

n101 in General Formula 1 above represents an integer from 0 to 11, and is preferably an integer from 0 to 2, with 0 or 1 being especially favorable, and 0 being even more especially favorable.

If n101 in General Formula 1 above is not zero, there are no particular restrictions on the position where the aforementioned $R^{101}$ is substituted on the triphenylene ring structure, but the triphenylene ring in General Formula 1 above preferably has a substituent $R^{101}$ besides the ring linked to the linking group $L^{101}$.

n102 in General Formula 1 above represents an integer from 0 to 7, and is preferably an integer from 0 to 2, with 0 or 1 being especially favorable, and 0 being even more especially favorable.

If n102 in General Formula 1 above is not zero, there are no particular restrictions on the position where the aforementioned $R^{102}$ is substituted on the dibenzothiophene or dibenzofuran structure, but the dibenzothiophene or dibenzofuran structure in General Formula 1 above preferably has a substituent $R^{102}$ besides the ring linked to the linking group $L^{101}$.

$L^{101}$ in General Formula 1 above is a single bond or a divalent linking group. There are no particular restrictions on the preferred range of $L^{101}$, but examples include a single bond and any divalent linking group. Of these, a single bond, an alkylene group, a silicon atom linking group, an arylene group, an aryl group, or a combination of these is preferable, and more preferable is a linking group expressed by General Formula 2 (described later). Moreover, if the aforementioned $L^{101}$ is an alkylene group, this alkylene group may have a substituent, and it is also favorable if the substituents of this alkyelene group, in particular, link together to form a cycloalkylene group.

One of $R^{101}$, $L^{101}$, and $R^{102}$ in General Formula 1 above includes a fluorine atom, a fluoroalkyl group, a cycloalkyl group, a cycloalkylene group, a silyl group, an alkylsilyl group, an arylsilyl group, or a silicon atom linking group (the aforementioned specific substituent). Specifically, if the aforementioned $R^{101}$ and $R^{102}$ do not include [any of] the aforementioned specific substituents, then $L^{101}$ includes the aforementioned specific substituent.

$L^{101}$ in General Formula 1 above may include any of a fluorine atom, a fluoroalkyl group, a cycloalkyl group, a cycloalkylene group, a silyl group, an alkylsilyl group, an arylsilyl group, or a silicon atom linking group (the aforementioned specific substituent), but in the present invention, of the aforementioned specific substituents, a preferable mode is one in which $L^{101}$ in General Formula 1 above includes a fluorine atom, a fluoroalkyl group, a cycloalkyl group, an alkylsilyl group, an arylsilyl group, or a silicon atom linking group, and a more preferable mode is one in which a fluorine atom, a fluoroalkyl group, or a cycloalkyl group is included, with a mode in which a cycloalkyl group is included being especially favorable.

The charge transport material of the present invention is preferably such that the compound expressed by General Formula 1 above is expressed by General Formula 2 below:

[Ninth Chemical Formula]

General Formula 2

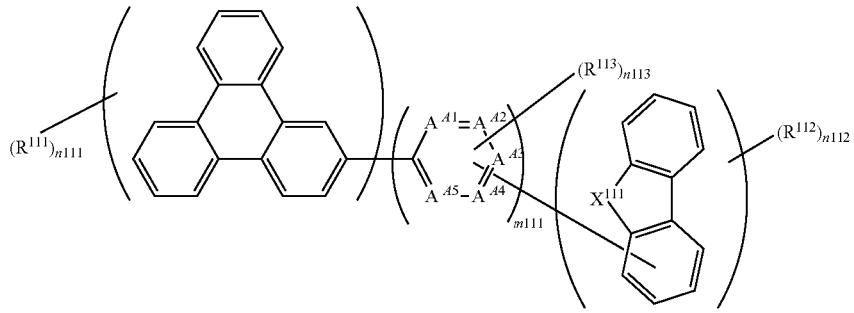

(in General Formula 2, $X^{111}$ represents a sulfur atom or an oxygen atom; $R^{111}$, $R^{112}$, and $R^{113}$ represent each independently an alkyl group, an aryl group, a heteroaryl group, a fluorine atom, or a silyl group, and may further be substituted with these groups; n111 represents an integer from 0 to 11; n112 represents an integer from 0 to 7; n113 represents an integer from 0 to 4; a plurality of $R^{111}$, $R^{112}$, and $R^{113}$ [groups] may be the same or different; $A^{41}$ to $A^{45}$ represent each independently CH (the hydrogen atom of the CH may be substituted with $R^{113}$) or a nitrogen atom; m111 represents an integer from 0 to 6; however, one of $R^{111}$, $R^{112}$, and $R^{113}$ includes a fluorine atom, a fluoroalkyl group, a cycloalkyl group, a silyl group, an alkylsilyl group, or an arylsilyl group; and n111, n112, and n113 will not be 0 at the same time.)

The preferred ranges of $X^{111}$, $R^{111}$, $R^{112}$, n111, and n112 in General Formula 2 above are respectively the same as the preferred ranges of $X^{101}$, $R^{101}$, $R^{102}$, n101, and n102 in General Formula 1 above.

The preferred ranges of the arylene group, or heteroarylene group, or a combination of these, which are six-membered monocycles, expressed by $A^{41}$ to $A^{45}$ in General Formula 2 above are the same as the preferred ranges of the aryl groups or heteroaryl groups [indicated] as $R^{101}$ and $R^{102}$ in General Formula 1 above.

m111 in General Formula 2 above is from 0 to 6, preferably from 1 to 6, more preferably from 1 to 5, and especially preferably from 1 to 4.

The $R^{113}$ [groups] in General Formula 2 above represent each independently an alkyl group, an aryl group, a heteroaryl group, a fluorine atom, or a silyl group, and may further be substituted with these groups. Examples of the alkyl group, aryl group, heteroaryl group, fluorine atom, or silyl group [indicated] as $R^{113}$ in General Formula 2 above are the same as the examples of $R^{202}$ in the aforementioned linking substituent ($R^{101}$).

The $R^{113}$ [groups] in General Formula 2 above preferably include a fluorine atom, a fluoroalkyl group, a cycloalkyl group, an alkylsilyl group, or an arylsilyl group, and more preferably include a fluorine atom, a fluoroalkyl group, or a cycloalkyl group, and especially preferably include a cycloalkyl group. The preferred range of each of these substituents is the same as the preferred range of each of the substituents listed for $R^{101}$ in General Formula 1 above.

n113 in General Formula 2 above represents an integer from 0 to 4, and if $R^{113}$ is a fluorine atom, it is preferably from 0 to 3, more preferably from 0 to 2, and especially preferably 0 or 1. If $R^{113}$ is an alkyl group, it is preferably from 0 to 2 and more preferably 0 or 1, with 0 being especially favorable. If $R^{201}$ and $R^{202}$ [sic] are aryl groups, heteroaryl groups, fluoroalkyl groups, alkylsilyl groups, or arylsilyl groups, it is preferably 0 or 1 and more preferably 0. If $R^{113}$ is a cycloalkyl group, it is preferably 0 or 1 and more preferably 1.

If m111 in General Formula 2 above is 2 or more, the repeating units expressed by m111 may be the same as or different from each other.

The repeating units expressed by m111 may have the number of $R^{113}$ [groups] within the preferred range given above in each of the repeating units, but if $R^{113}$ is a fluorine atom, the number of specific substituents in all the repeating units expressed by m111, that is, in all the $L^{111}$ [groups] in General Formula 1 above, is preferably from 0 to 3, more preferably from 0 to 2, and especially preferably 0 or 1. If $R^{113}$ is an alkyl group, [the number] is preferably from 0 to 2, and more preferably 0 or 1, with 0 being especially favorable. If $R^{201}$ and $R^{202}$ are aryl groups, heteroaryl groups, fluoroalkyl groups, alkylsilyl groups, or arylsilyl groups, [the number] is preferably 0 or 1 and more preferably 0. If $R^{113}$ is a cycloalkyl group, [the number] is preferably 0 or 1 and more preferably 1.

It is preferable for the repeating units expressed by m111 to have the number of $R^{113}$ [groups] within the aforementioned preferred range in each of the repeating units and have the number of $R^{113}$ [groups] within the aforementioned preferred range in all the repeating units expressed by m111. This does not apply, however, if the aforementioned specific substituent is a fluorine atom.

The charge transport material of the present invention is preferably such that the compound expressed by General Formula 1 above is expressed by General Formula 3 below:

[Tenth Chemical Formula]

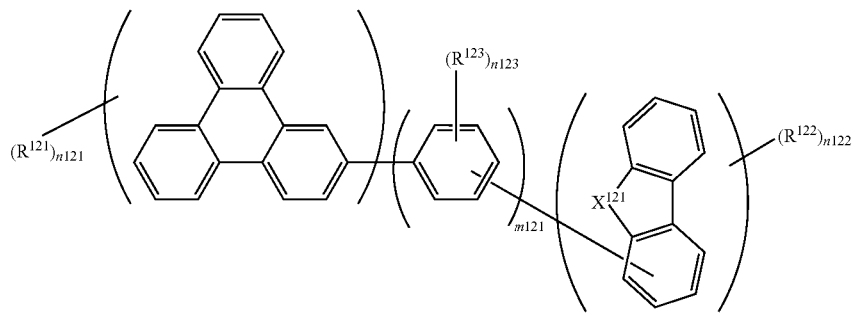

General Formula 3

(in General Formula 3, $X^{121}$ represents a sulfur atom or an oxygen atom; $R^{121}$, $R^{122}$, and $R^{123}$ represent each independently an alkyl group, an aryl group, a heteroaryl group, a fluorine atom, or a silyl group, and may further be substituted with these groups; n121 represents an integer from 0 to 11; n122 represents an integer from 0 to 7; n123 represents an integer from 0 to 4; a plurality of $R^{121}$, $R^{122}$, and $R^{123}$ [groups] may be the same or different; m121 represents an integer from 0 to 6; however, one of $R^{121}$, $R^{122}$, and $R^{123}$ includes a fluorine atom, a fluoroalkyl group, a cycloalkyl group, a silyl group, an alkylsilyl group, or an arylsilyl group; and n121, n122, and n123 will not be 0 at the same time.)

The preferred ranges of $X^{121}$, $R^{121}$, $R^{122}$, n121, and n122 in General Formula 3 above are respectively the same as the preferred ranges of $X^{101}$, $R^{101}$, $R^{102}$, n101, and n102 in General Formula 1 above.

The preferred ranges of $R^{123}$, m121, and n123 in General Formula 3 above are respectively the same as the preferred ranges of $R^{113}$, m111, and n113 in General Formula 2 above.

The charge transport material of the present invention is preferably such that the compound expressed by General Formula 3 above is expressed by General Formula 6 below:

[Eleventh Chemical Formula]

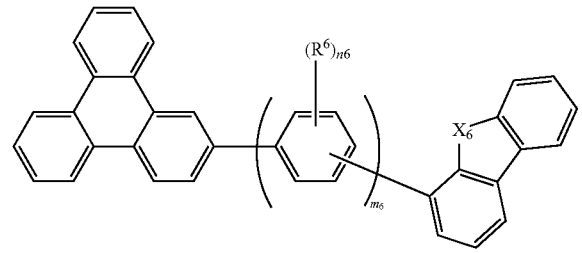

General Formula 6

(in General Formula 6, $X^6$ represents a sulfur atom or an oxygen atom; m6 represents an integer from 1 to 6; $R^6$ represents an alkyl group, an aryl group, a heteroaryl group, a fluorine atom, or a silyl group; n6 represents an integer from 0 to 4; however, of the m6×n6 number of $R^6$ [groups], at least one is a fluorine atom, a fluoroalkyl group, a cycloalkyl group, a silyl group, an alkylsilyl group, or an arylsilyl group.)

The preferred range of $X^6$ in General Formula 6 above is the same as the preferred range of $X^{101}$ in General Formula 1 above. The preferred ranges of $R^6$ and n6 in General Formula 6 above are respectively the same as the preferred ranges of $R^{113}$ and n113 in General Formula 2 above. m6 represents an integer from 1 to 6. m6 is preferably from 0 to 2 and more preferably 0 or 1. However, of the m6×n6 number of $R^6$ [groups], at least one is a fluorine atom, a fluoroalkyl group, a cycloalkyl group, a silyl group, an alkylsilyl group, or an arylsilyl group.

The compound expressed by General Formula 1 above is more preferably composed of only carbon atoms and hydrogen atoms, excluding the oxygen atoms and sulfur atoms in the dibenzothiophene skeleton and the dibenzofuran skeleton. In addition, it is even more preferable for the compound expressed by General Formula 1 above to include a cycloalkyl group.

The $T_1$ energy in a film state of the compound expressed by General Formula 1 above is preferably at least 2.39 eV (55.0 kcal/mol) and no more than 3.25 eV (75.0 kcal/mol), more preferably at least 2.47 eV (57.0 kcal/mol) and no more than 3.04 eV (70.0 kcal/mol), and even more preferably at least 2.52 eV (58.0 kcal/mol) and no more than 2.82 eV (65.0 kcal/mol). In particular, when a phosphorescent material is used as the light-emitting material, it is preferable for the $T_1$ energy to be within the aforementioned ranges.

By measuring the phosphorescence spectrum of a thin film of the material, the $T_1$ energy can be found from the short-wavelength end thereof. For instance, a film of the material is formed in a thickness of approximately 50 nm by a vacuum deposition method over a washed quartz glass substrate, and the phosphorescence spectrum of the thin film is measured using a Hitachi F-7000 spectrofluoro-photometer (Hitachi High-Technologies) at the temperature of liquid nitrogen. The $T_1$ energy can be found by converting the rising wavelength on the short-wavelength side of the emission spectrum thus obtained to energy units.

With the charge transport material of the present invention, the molecular weight of the compound expressed by General Formula 1 above is preferably no more than 1200, more preferably no more than 1000, even more preferably at least 500 and no more than 1000, with at least 550 and no more than 900 being especially favorable, and at least 600 and no more than 850 being most favorable. By keeping the molecular weight within these ranges, it is possible to obtain a material that has good film quality and excellent suitability to vapor deposition and sublimation purification.

From the standpoint of stable operation of the organic electroluminescent element with respect to heat emission in element drive or during high-temperature drive, the glass transition temperature (Tg) of the compound expressed by General Formula 1 is preferably at least 80° C. and no more than 400° C., more preferably at least 100° C. and no more than 400° C., and even more preferably at least 120° C. and no more than 400° C.
Concrete examples of the compound expressed by General Formula 1 are given below, but the present invention is not limited to or by these:
[Twelfth Chemical Formula]
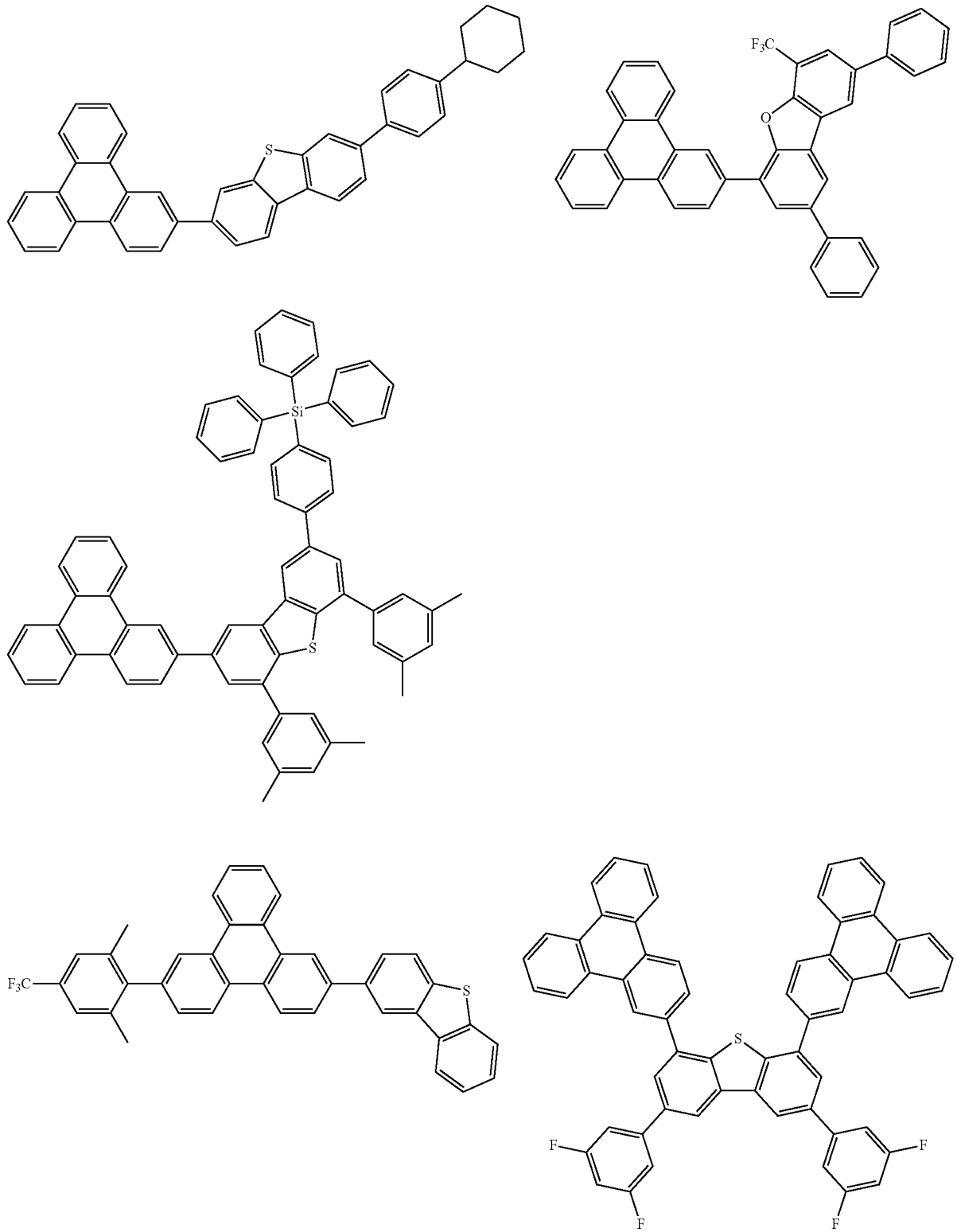

-continued
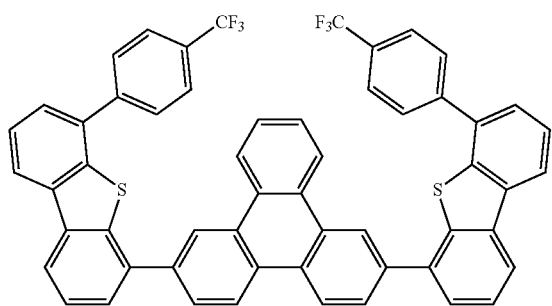
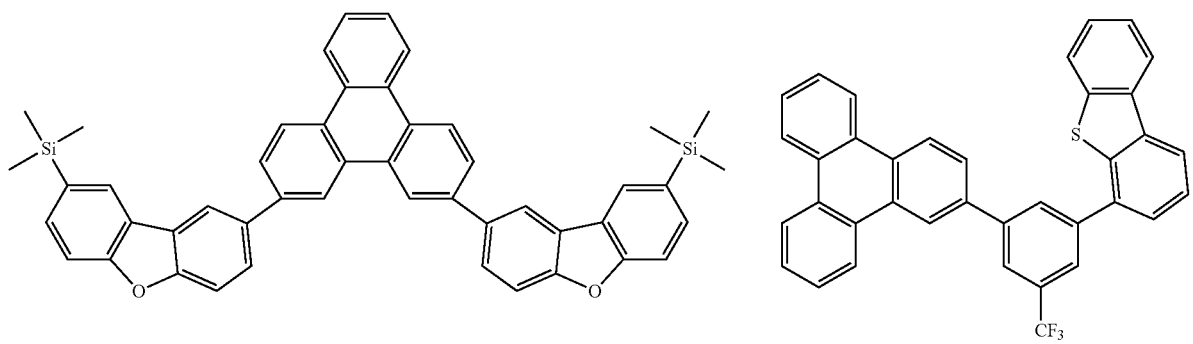
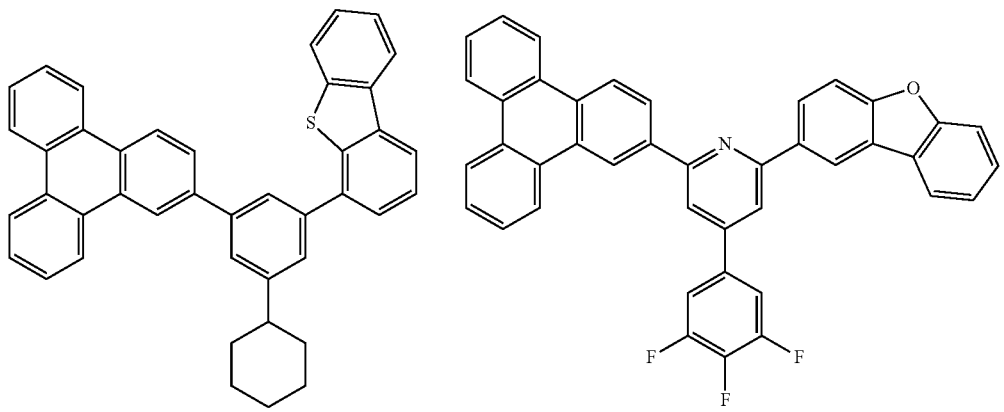
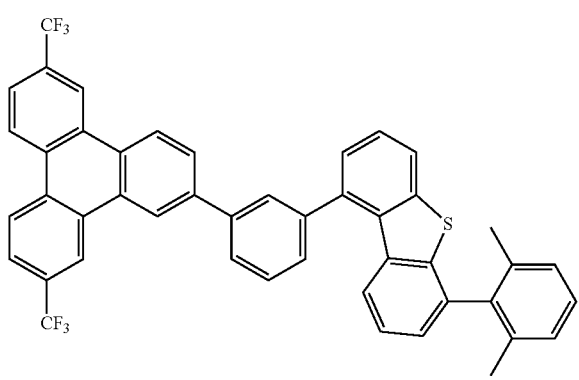

[Thirteenth Chemical Formula]
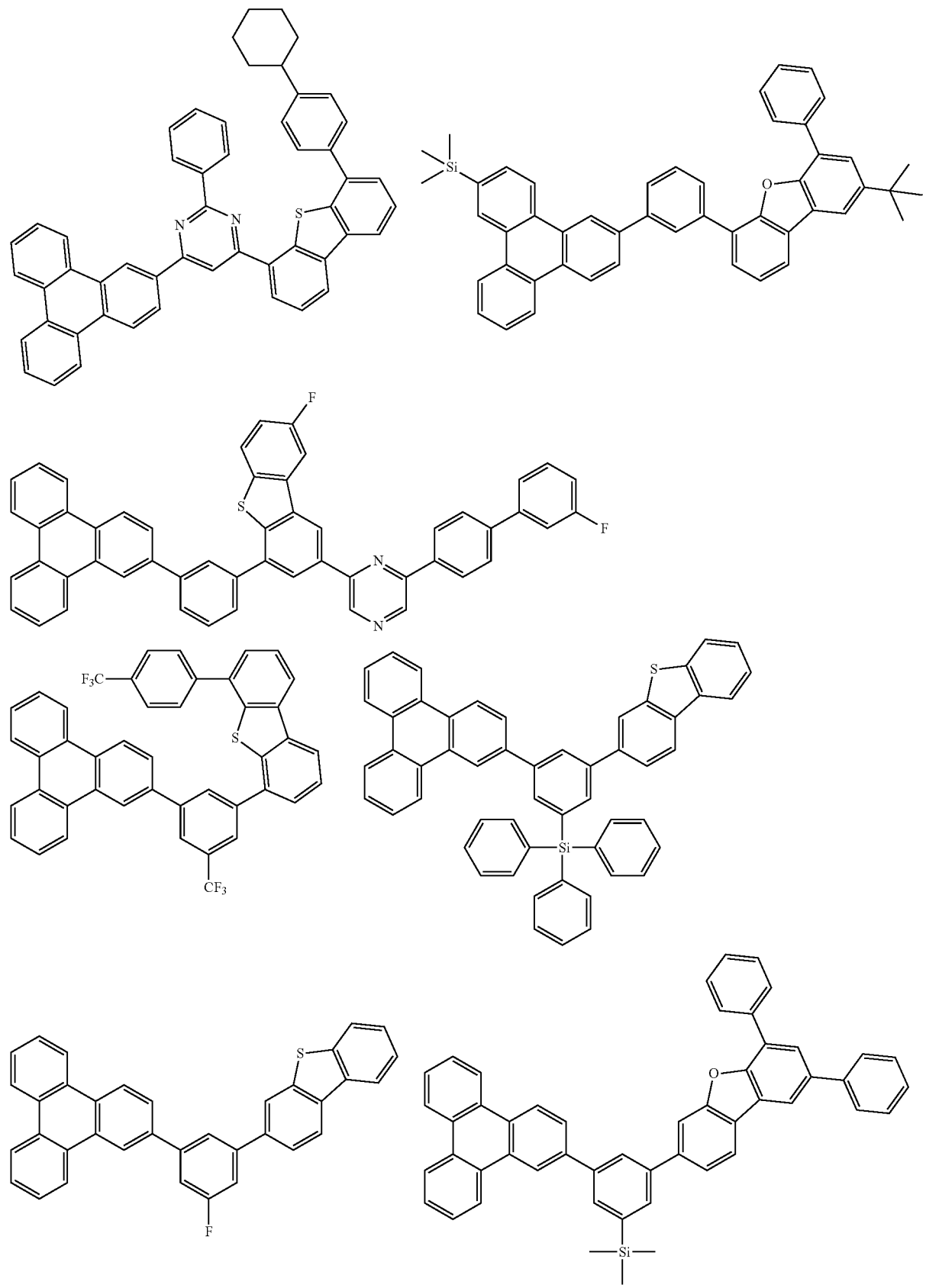

-continued
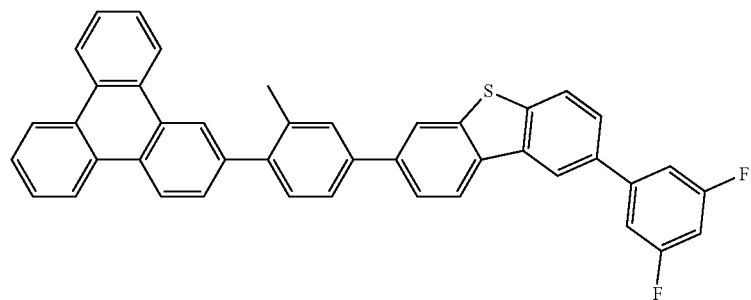
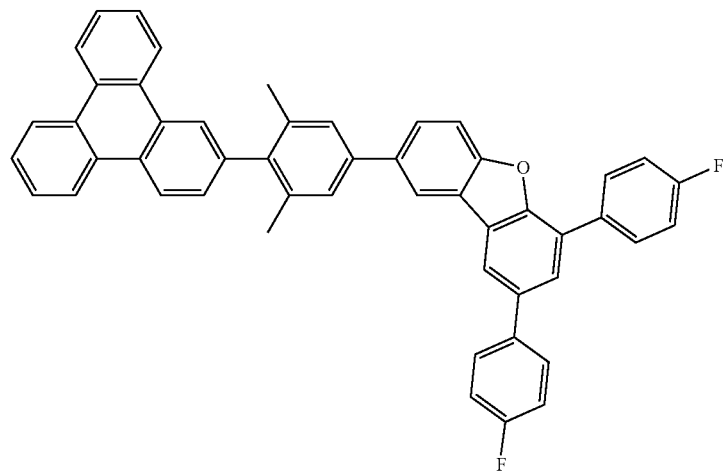
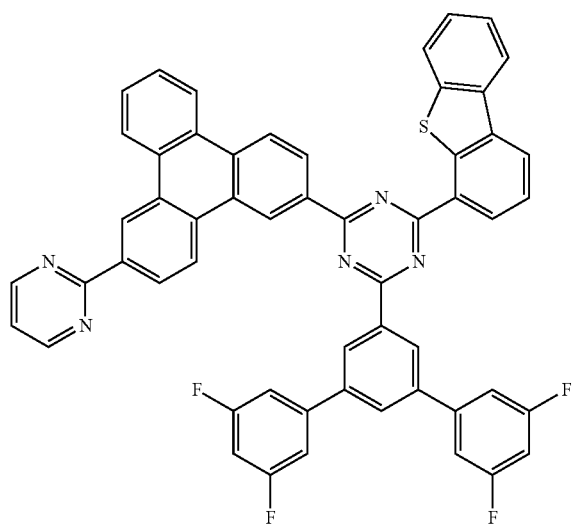
[Fourteenth Chemical Formula]
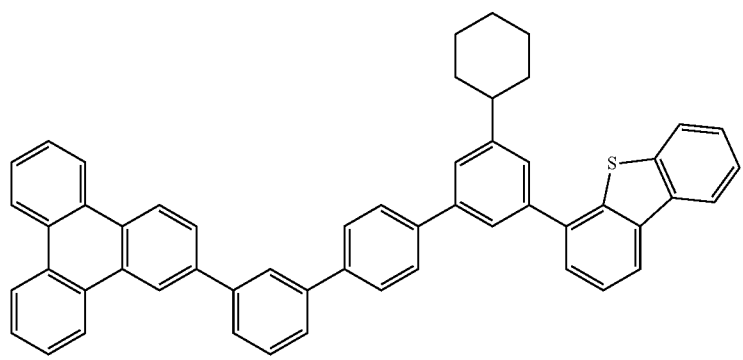

-continued
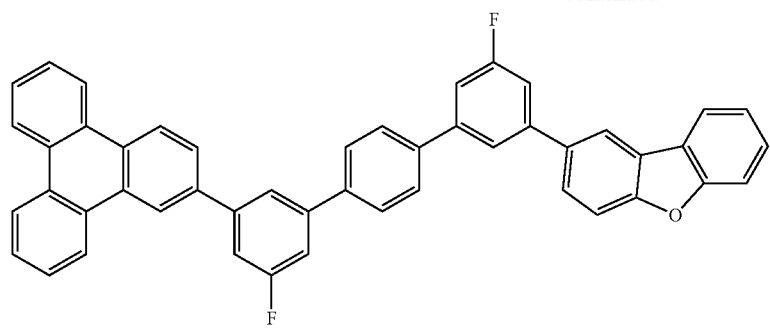
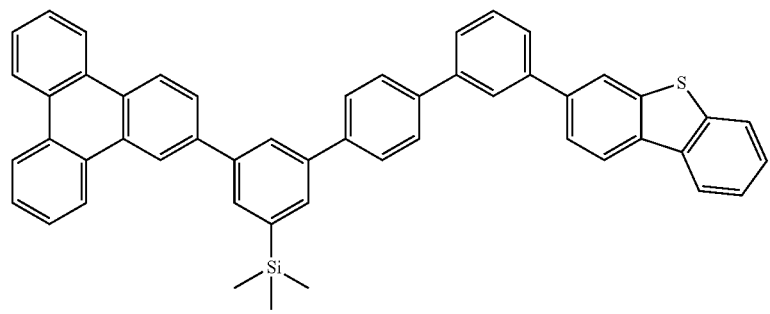
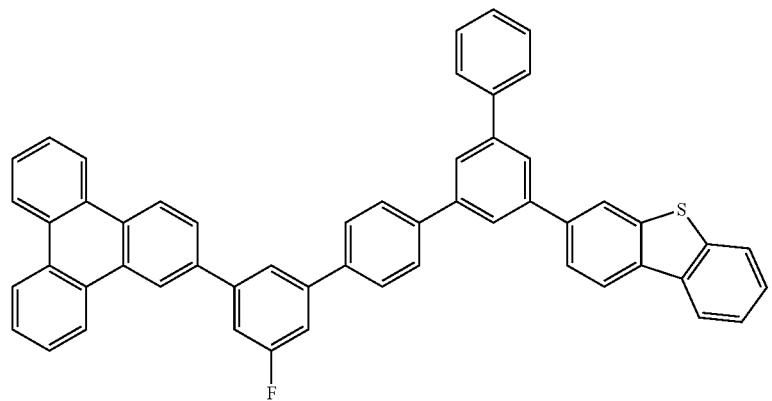
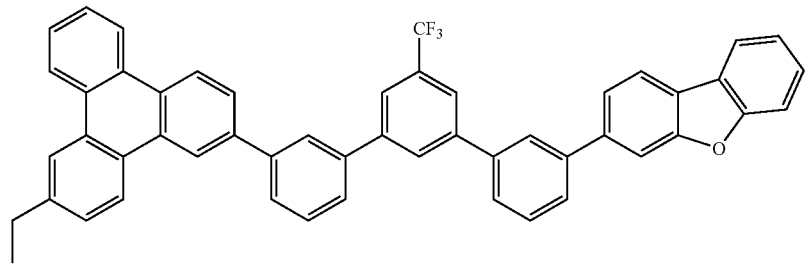
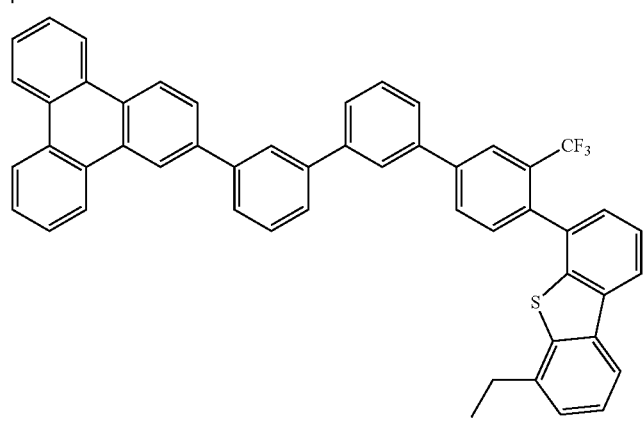

-continued
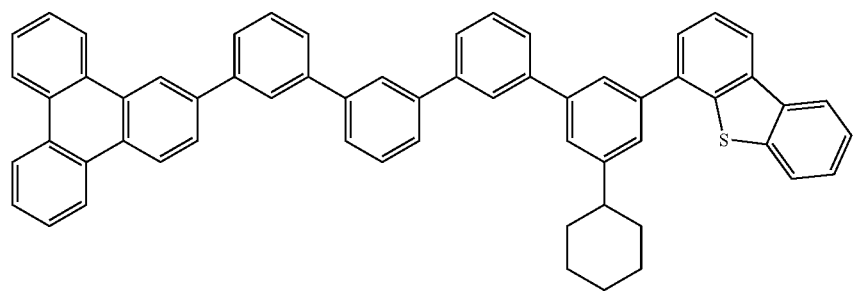
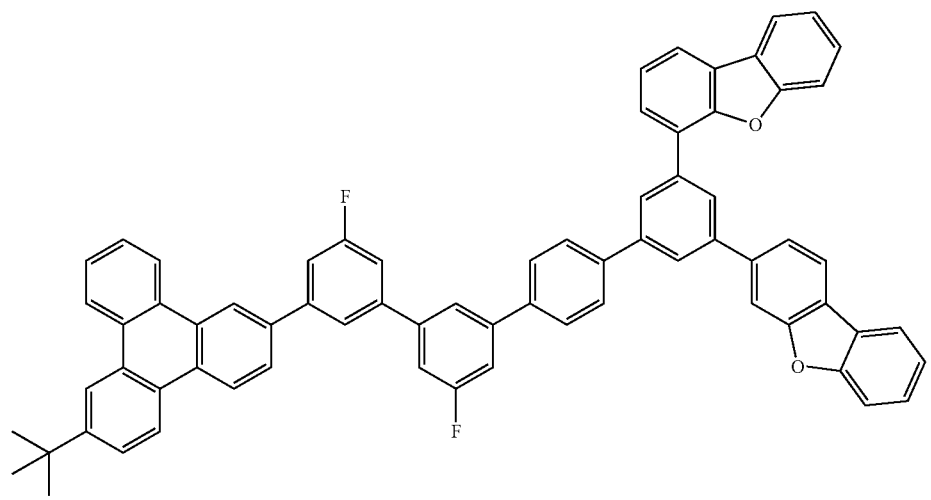
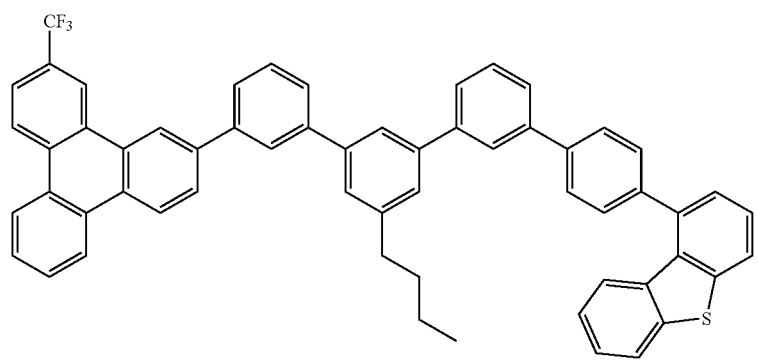
[Fifteenth Chemical Formula]
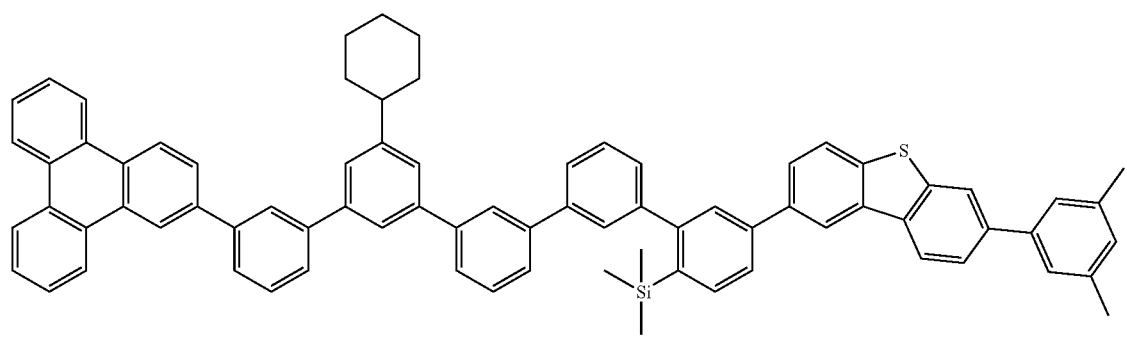

-continued
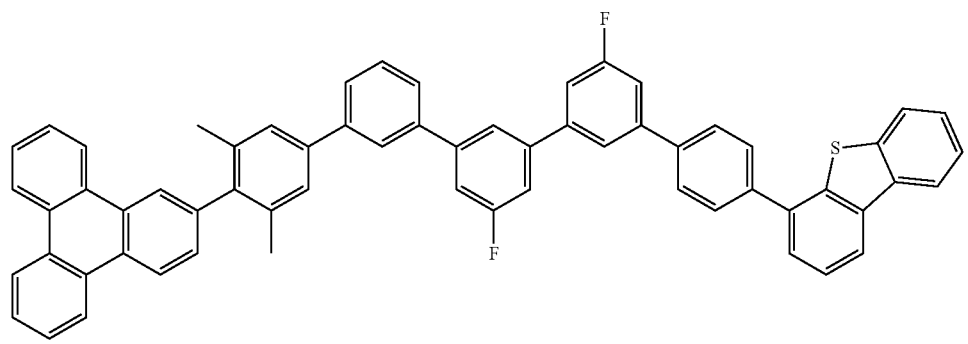
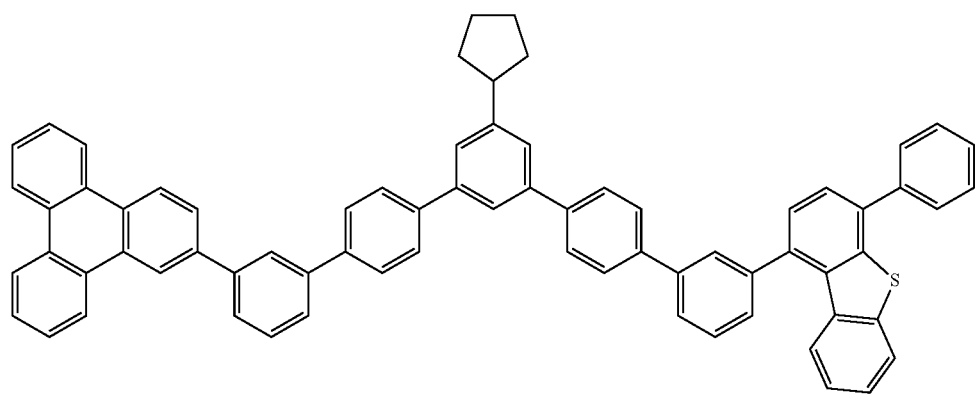
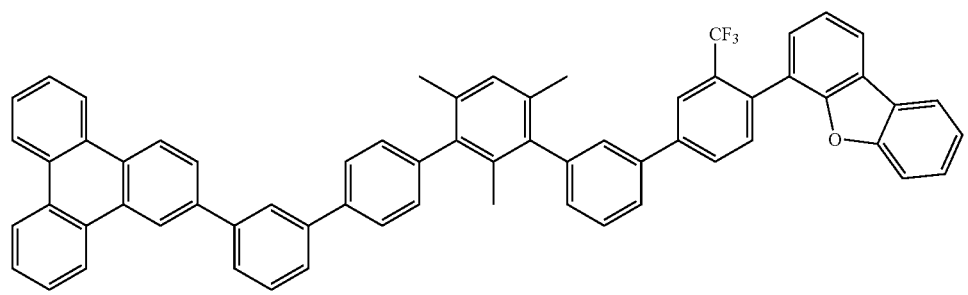
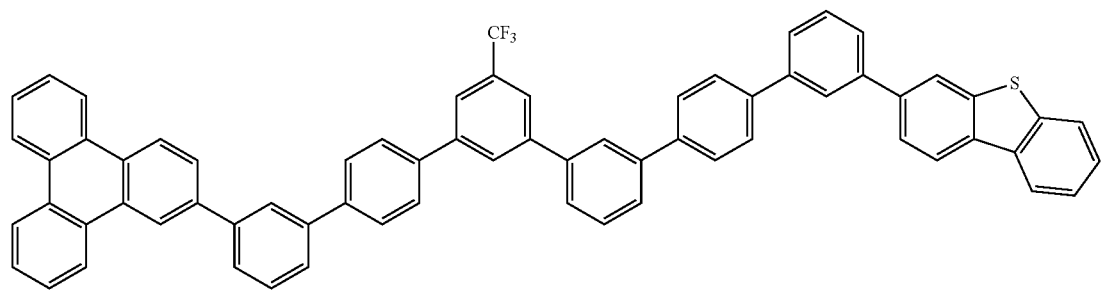
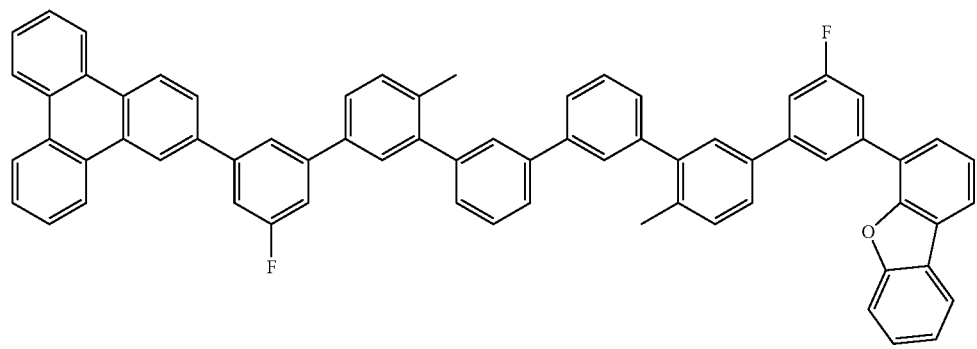

-continued
[Sixteenth Chemical Formula]
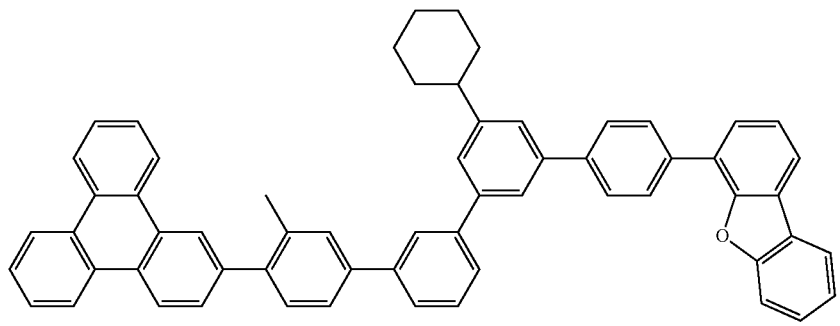
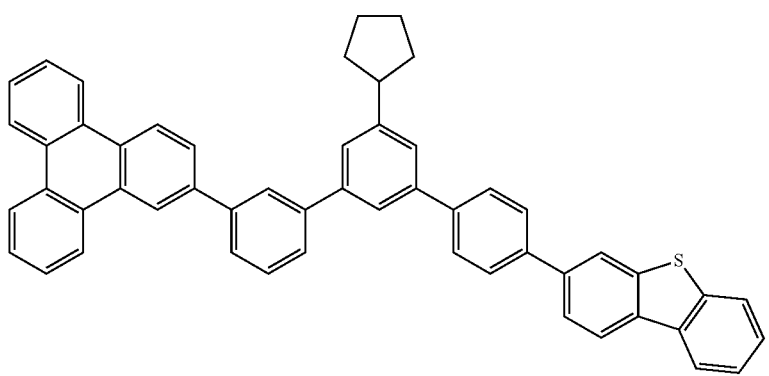
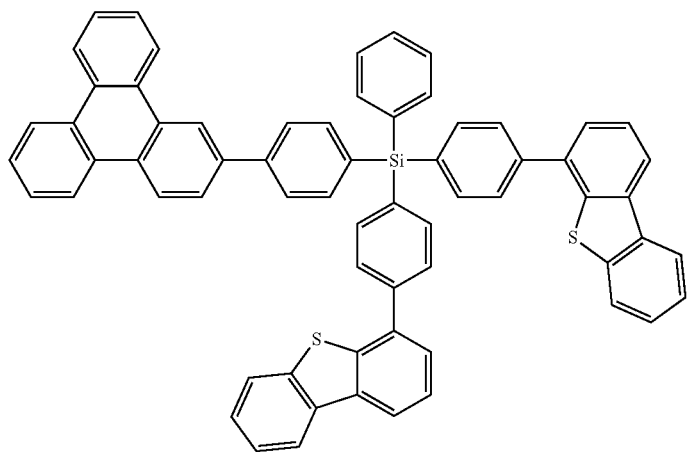
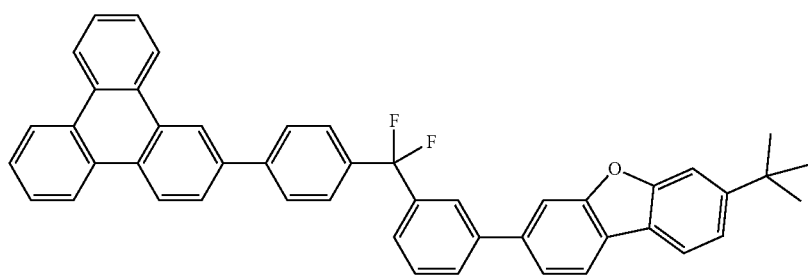

-continued

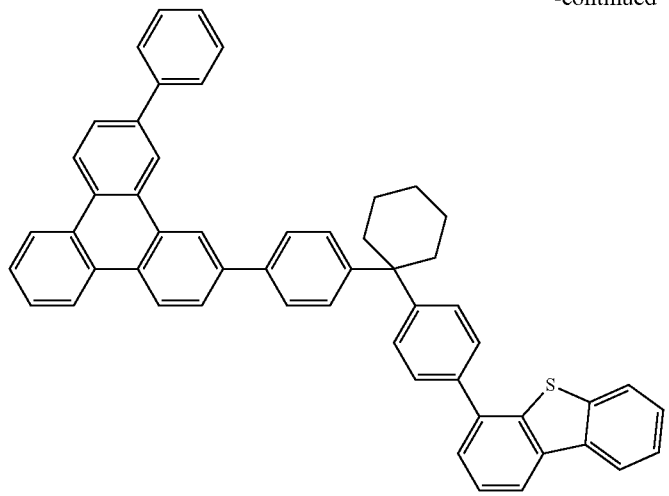

The compound expressed by General Formula 1 above can be synthesized by the methods described in Japanese Laid-Open Patent Applications 2004-43349 and 2004-83481, US 2006/0280965, WO 2009/021107, Japanese Laid-Open Patent Application 2009-114068, and Japanese Translation of PCT International Application 2010-535809, or by combining other publicly known reactions.

After synthesis, it is preferable for purification by column chromatography, recrystallization, or the like to be performed, followed by sublimation purification. Sublimation purification not only allows organic impurities to be separated, but also allows inorganic salts, residual solvents, and the like to be effectively removed.

Organic Electroluminescent Element

The organic electroluminescent element of the present invention has a substrate, a pair of electrodes that are disposed on this substrate and that include an anode and a cathode, and an organic layer disposed between these electrodes, and is characterized in that the aforementioned organic layer includes a phosphorescent material and the charge transport material of the present invention, i.e., the compound expressed by General Formula 1 above [sic][2].

[2] Translator's note: apparent error in the original; "above" should be "below."

[Seventeenth Chemical Formula]

General Formula 1

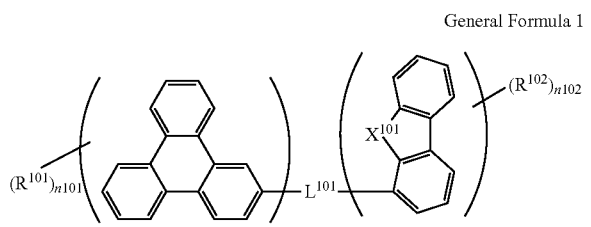

(in General Formula 1, $X^{101}$ represents a sulfur atom or an oxygen atom; $R^{101}$ and $R^{102}$ represent each independently an alkyl group, an aryl group, a heteroaryl group, a fluorine atom, or a silyl group, and may further be substituted with these groups; n101 represents an integer from 0 to 11; n102 represents an integer from 0 to 7; a plurality of $R^{101}$ and $R^{102}$ [groups] may be the same or different; and $L^{101}$ represents a single bond or a divalent linking group; however, one of $R^{101}$, $L^{101}$, and $R^{102}$ includes a fluorine atom, fluoroalkyl group, cycloalkyl group, cycloalkylene group, silyl group, alkylsilyl group, arylsilyl group, or silicon atom linking group.)

There are no particular restrictions on the configuration of the organic electroluminescent element of the present invention. FIG. 1 shows one example of the configuration of the organic electroluminescent element of the present invention. The organic electroluminescent element 10 of FIG. 1 has, on a substrate 2, organic layers between a pair of electrodes (an anode 3 and a cathode 9).

The element configuration, substrate, cathode, and anode of the organic electroluminescent element are discussed in detail in Japanese Laid-Open Patent Application 2008-270736, for example, and what is discussed in this publication can be applied to the present invention.

Preferred modes of the organic electroluminescent element of the present invention will be described in detail below in the order of the substrate, electrodes, organic layers, protective layer, sealing container, drive method, emission wavelength, and applications.

<Substrate>

The organic electroluminescent element of the present invention has a substrate.

The substrate used in the present invention is preferably a substrate that will not scatter or attenuate light emitted from the organic layers. In the case of an organic material, one with excellent heat resistance, dimensional stability, solvent resistance, electrical insulation properties, and workability is preferable.

<Electrodes>

The organic electroluminescent element of the present invention has a pair of electrodes that are disposed on the aforementioned substrate and that include an anode and a cathode.

For the quality of the light-emitting element, it is preferable that at least either the anode or cathode constituting the pair of electrodes be transparent or semitransparent.

(Anode)

In general, there are no particular restrictions on the shape, structure, size, and so forth of the anode as long as it functions as an electrode that supplies holes to the organic layers, and one can be suitably selected from publicly known electrode materials depending on the purpose and application of the light-emitting element. As was discussed above, the anode is usually provided as a transparent anode.

(Cathode)

In general, there are no particular restrictions on the shape, structure, size, and so forth of the cathode as long as it functions as an electrode that injects electrons into the organic layers, and one can be suitably selected from publicly known electrode materials depending on the purpose and application of the light-emitting element.

<Organic Layers>

The organic electroluminescent element of the present invention has organic layers disposed between the aforementioned electrodes and is characterized in that the aforementioned organic layers include a phosphorescent material and a compound expressed by General Formula 1 above.

There are no particular restrictions on the aforementioned organic layers, which can be suitably selected according to the purpose and application of the organic electroluminescent element, but [the organic layers] are preferably formed over the aforementioned transparent electrode(s) or the aforementioned semi-transparent electrode(s). In this case, the organic layers are formed on the entire surface or one face of the aforementioned transparent electrode(s) or the aforementioned semi-transparent electrode(s).

There are no particular restrictions on the shape, size, thickness, and so forth of the organic layers, which can be suitably selected according to the purpose.

The configuration of the organic layers, a method for forming the organic layers, preferred modes of various layers configuring the organic layers, and the materials used in the various layers in the organic electroluminescent element of the present invention will be described in order below.

(Configuration of Organic Layers)

In the organic electroluminescent element of the present invention, the aforementioned organic layers preferably include a charge transport layer. The aforementioned term "charge transport layer" refers to a layer in which charge movement occurs when voltage is applied to the organic electroluminescent element. Concrete examples include a hole injection layer, a hole transport layer, an electron blocking layer, a light-emitting layer, a hole blocking layer, an electron transport layer, or an electron injection layer. If the aforementioned charge transport layer is a hole injection layer, a hole transport layer, an electron blocking layer, or a light-emitting layer, it is possible to manufacture a low-cost and high-efficiency organic electroluminescent element.

It is preferable that the organic electroluminescent element of the present invention have a light-emitting layer containing the aforementioned phosphorescent material and other organic layers and that the aforementioned light-emitting layer include a compound expressed by General Formula 1 above. In the organic electroluminescent element of the present invention, furthermore, the aforementioned organic layers more preferably have a light-emitting layer containing the aforementioned phosphorescent material and other organic layers. However, it is not absolutely necessary for the organic electroluminescent element of the present invention to have any clear separation between layers even in cases where the aforementioned organic layers have a light-emitting layer and other organic layers.

The organic electroluminescent element of the present invention is such that the aforementioned organic layers include a phosphorescent material and a compound expressed by General Formula 1 above. In this case, there are no particular restrictions on the site where the aforementioned phosphorescent material and compound expressed by General Formula 1 above are included. In the present invention, it is more preferable that a light-emitting layer containing the aforementioned phosphorescent material and other organic layers be present in the aforementioned organic layers and that the aforementioned light-emitting layer include a compound expressed by General Formula 1 above. In this case, the compound expressed by General Formula 1 above is preferably used as the host material of the light-emitting layer (hereinafter also referred to as "host compound").

The compound expressed by General Formula 1 above may be contained in any of the organic layers between the cathode and the anode of the organic electroluminescent element.

Examples of organic layers that may contain the compound expressed by General Formula 1 above include the light-emitting layer, a hole injection layer, a hole transport layer, an electron transport layer, an electron injection layer, an exciton blocking layer, and a charge blocking layer (a hole blocking layer, an electron blocking layer, etc.), with the light-emitting layer, an exciton blocking layer, a charge blocking layer, an electron transport layer, or an electron injection layer being preferable, and the light-emitting layer, an exciton blocking layer, a charge blocking layer, or an electron transport layer being more preferable, and the light-emitting layer or a hole blocking layer being even more preferable.

When the compound expressed by General Formula 1 above is contained in the light-emitting layer, it is preferably contained in an amount of 0.1 to 99 wt %, more preferably 1 to 95 wt %, and [even] more preferably 10 to 95 wt %, with respect to the total weight of the light-emitting layer.

The maximum emission wavelength of the light-emitting material that uses the compound expressed by General Formula 1 above is preferably from 400 to 700 nm, more preferably from 500 to 700 nm, even more preferably from 520 to 650 nm, and most preferably from 520 to 550 nm.

Moreover, it is also preferable for the aforementioned electron transport layer or hole blocking layer (more preferably hole blocking layer) to be present between the aforementioned pair of electrodes and for the aforementioned electron transport layer or the aforementioned hole blocking layer to contain the compound expressed by General Formula 1 above.

When the compound expressed by General Formula 1 above is contained in an organic layer other than the light-emitting layer, it is preferably contained in an amount of 70 to 100 wt % and more preferably 85 to 100 wt % with respect to the total weight of this organic layer.

A plurality of each of these organic layers may be provided, and when a plurality of layers are provided, they may be formed from the same material, or they may be formed from different materials for each layer.

(Organic Layer Formation Method)

Each of the organic layers of the organic electroluminescent element of the present invention can be favorably formed by vapor deposition, sputtering, or another such dry film formation method, or by transfer, printing, spin coating, bar coating, or another such wet film formation method (solution coating method) as well.

In the organic electroluminescent element of the present invention, the organic layers disposed between the aforementioned pair of electrodes preferably include at least one layer that is formed by vapor deposition of a composition containing the compound expressed by General Formula 1 above.

(Light-Emitting Layer)

When an electric field is applied, the light-emitting layer accepts holes from the anode, the hole injection layer, or the hole transport layer, accepts electrons from the cathode, the electron injection layer, or the electron transport layer, and has the function of emitting light by providing a site for the rebinding of holes and electrons. However, the aforementioned light-emitting layer in the present invention is not necessarily limited to emission of light by such a mechanism. The light-emitting layer in the organic electroluminescent element of the present invention preferably contains at least one type of phosphorescent material.

The aforementioned light-emitting layer in the organic electroluminescent element of the present invention may be constituted solely from the aforementioned light-emitting material or may also be made up of a mixed layer of a host material and the aforementioned light-emitting material. With regard to the types of the aforementioned light-emitting material, there may be just one kind or two or more kinds. The aforementioned host material is preferably a charge transport material. With regard to the types of the aforementioned host material, there may be just one kind or two or more kinds. Examples include a mixed configuration of an electron transporting host material and a hole transporting host material. Furthermore, a material which does not have a charge transporting property and does not emit light may also be included in the aforementioned light-emitting layer.

Moreover, the light-emitting layer may be a single layer or a multilayer of two or more layers, and the same light-emitting material or host material may be included in each layer, or different materials may be included in each layer. When there are a plurality of light-emitting layers, each light-emitting layer may also emit light of a different color.

There are no particular restrictions on the thickness of the light-emitting layer, but in general, it is preferably from 2 to 500 nm, and from the standpoint of external quantum efficiency, it is more preferably from 3 to 200 nm and even more preferably from 5 to 100 nm.

A preferred mode of the organic electroluminescent element of the present invention is that the aforementioned light-emitting layer contains the compound expressed by General Formula 1 above, and a more preferred mode is that the compound expressed by General Formula 1 above is used as the host material of the aforementioned light-emitting layer. Here, in this Specification, the host material is a compound that mainly handles the injection and transport of charges in the light-emitting layer, and is also a compound that substantially does not emit light itself [The phrase] "substantially does not emit light" here means that the amount of light emitted from this compound that substantially does not emit light is preferably no more than 5% of the total amount of light emitted by the entire element, more preferably no more than 3%, and even more preferably no more than 1%.

Host materials other than the aforementioned light-emitting material and the compound expressed by General Formula 1 above will be described in order below as the material of the aforementioned light-emitting layer. Note that the compound expressed by General Formula 1 above may also be used in a layer other than the aforementioned light-emitting layer in the organic electroluminescent element of the present invention.

(Light-Emitting Material)

A phosphorescent material, fluorescent material, and the like can be used as the light-emitting material in the present invention.

The light-emitting layer in the present invention can contain two or more types of light-emitting material in order to improve color purity or expand the emission wavelength band. It is preferable for at least one type of the light-emitting material to be a phosphorescent material.

In the present invention, in addition to at least one type of phosphorescent material contained in the light-emitting layer, a fluorescent material or a phosphorescent material different from the phosphorescent material contained in the light-emitting layer can be used as the light-emitting material.

These fluorescent materials and phosphorescent materials are discussed at length, for example, in paragraph numbers [0100] to [0164] of Japanese Laid-Open Patent Application 2008-270736 and paragraph numbers [0088] to [0090] of Japanese Laid-Open Patent Application 2007-266458, and what is discussed in these publications can be applied to the present invention.

Examples of phosphorescent materials that can be used in the present invention include the phosphorescent compounds or the like described in patent documents such as U.S. Pat. No. 6,303,238 B1, U.S. Pat. No. 6,097,147, WO 00/57676, WO 00/70655, WO 01/08230, WO 01/39234 A2, WO 01/41512 A1, WO 02/02714 A2, WO 02/15645 A1, WO 02/44189 A1, WO 05/19373 A2, Japanese Laid-Open Patent Applications 2001-247859, 2002-302671, 2002-117978, 2003-133074, 2002-235076, 2003-123982, and 2002-170684, EP 1211257, and Japanese Laid-Open Patent Applications 2002-226495, 2002-234894, 2001-247859, 2001-298470, 2002-173674, 2002-203678, 2002-203679, 2004-357791, 2006-256999, 2007-19462, 2007-84635, and 2007-96259, and WO 07/095118, WO 10/111175, WO 10/027583, and WO 10/028151. Of these, examples of more preferable light-emitting materials include iridium (Ir) complexes, platinum (Pt) complexes, copper complexes, rhenium complexes, tungsten complexes, rhodium complexes, ruthenium complexes, palladium complexes, osmium complexes, europium complexes, terbium complexes, gadolinium complexes, dysprosium complexes, cerium complexes, and other such phosphorescent metal complex compounds. Especially preferable are iridium (Ir) complexes, platinum (Pt) complexes, and rhenium complexes, and of these, iridium (Ir) complexes, platinum (Pt) complexes, and rhenium complexes that include at least one coordination from among a metal-carbon bond, a metal-nitrogen bond, a metal-oxygen bond, and a metal-sulfur bond are preferred. From the standpoints of luminous efficiency, drive durability, chromaticity, and so forth, iridium (Ir) complexes and platinum (Pt) complexes are especially favorable, with iridium (Ir) complexes being most favorable.

For the phosphorescent material contained in the light-emitting layer in the present invention, it is preferable to use an iridium (Ir) complex expressed by General Formula E-1 below or a platinum (Pt) complex expressed by General Formula C-1 below:

The iridium (Ir) complex expressed by General Formula E-1 will be described.

[Eighteenth Chemical Formula]

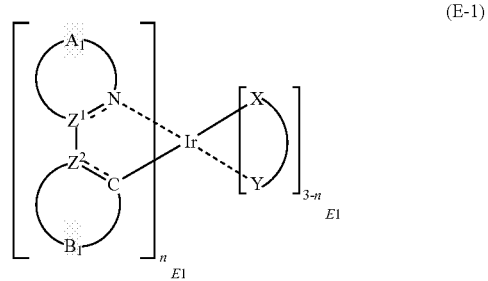

(E-1)

In General Formula E-1, $Z^1$ and $Z^2$ represent each independently a carbon atom or a nitrogen atom.

$A_1$ represents a group of atoms forming a five- or six-membered heterocycle together with $Z^1$ and a nitrogen atom.

$B_1$ represents a group of atoms forming a five- or six-membered ring together with $Z^2$ and a carbon atom.

(X—Y) represents a monoanionic bidentate ligand.

$n_{E1}$ represents an integer from 1 to 3. If $n_{E1}$ is 2 or 3, then there are two or three ligands that include $Z^1$, $Z^2$, $A_1$, and $B_1$, and these two or three ligands may be the same as or different from each other.

$n_{E1}$ represents an integer from 1 to 3, with 2 or 3 being preferable, and 3 being more preferable.

$Z^1$ and $Z^2$ represent each independently a carbon atom or a nitrogen atom. $Z^1$ and $Z^2$ are preferably carbon atoms.

$A_1$ represents a group of atoms forming a five- or six-membered heterocycle together with $Z^1$ and a nitrogen atom. Examples of five- or six-membered heterocycles that contain $A_1$, $Z^1$, and a nitrogen atom include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring.

From the standpoints of the stability of the complex, control of emission wavelength, and luminescent quantum yield, the five- or six-membered heterocycle formed by $A_1$, $Z^1$, and a nitrogen atom is preferably a pyridine ring, a pyrazine ring, an imidazole ring, or a pyrazole ring, more preferably a pyridine ring, an imidazole ring, or a pyrazine ring, even more preferably a pyridine ring or an imidazole ring, and most preferably a pyridine ring.

The aforementioned five- or six-membered heterocycle formed by $A_1$, $Z^1$, and a nitrogen atom may have a substituent, and [a group from] Substituent Group A described below can be used as a substituent on a carbon atom, while [a group from] Substituent Group B described below can be used as a substituent on a nitrogen atom. The substituent on a carbon atom is preferably an alkyl group, a perfluoroalkyl group, an aryl group, a heteroaryl group, a dialkylamino group, a diarylamino group, an alkoxy group, a cyano group, or a fluorine atom.

<<Substituent Group A>>

Examples [of Substituent Group A] include alkyl groups (preferably with a carbon number of 1 to 30, more preferably with a carbon number of 1 to 20, and especially preferably with a carbon number of 1 to 10, such as a methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as a vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthryl); amino groups (preferably with a carbon number of 0 to 30, more preferably with a carbon number of 0 to 20, and especially preferably with a carbon number of 0 to 10, such as amino, methylamino, dimethylamino, diethylamino, dibenzylamino, diphenylamino, and ditolylamino); alkoxy groups (preferably with a carbon number of 1 to 30, more preferably with a carbon number of 1 to 20, and especially preferably with a carbon number of 1 to 10, such as methoxy, ethoxy, butoxy, and 2-ethylhexyloxy); aryloxy groups (preferably with a carbon number of 6 to 30, more preferably with a carbon number of 6 to 20, and especially preferably with a carbon number of 6 to 12, such as phenyloxy, 1-naphthyloxy, and 2-naphthyloxy); heterocyclic oxy groups (preferably with a carbon number of 1 to 30, more preferably with a carbon number of 1 to 20, and especially preferably with a carbon number of 1 to 12, such as pyridyloxy, pyrazinyloxy, pyrimidinyloxy, and quinolyloxy); acyl groups (preferably with a carbon number of 2 to 30, more preferably with a carbon number of 2 to 20, and especially preferably with a carbon number of 2 to 12, such as acetyl, benzoyl, formyl, and pivaloyl); alkoxycarbonyl groups (preferably with a carbon number of 2 to 30, more preferably with a carbon number of 2 to 20, and especially preferably with a carbon number of 2 to 12, such as methoxycarbonyl and ethoxycarbonyl); aryloxycarbonyl groups (preferably with a carbon number of 7 to 30, more preferably with a carbon number of 7 to 20, and especially preferably with a carbon number of 7 to 12, such as phenyloxycarbonyl); acyloxy groups (preferably with a carbon number of 2 to 30, more preferably with a carbon number of 2 to 20, and especially preferably with a carbon number of 2 to 10, such as acetoxy and benzoyloxy); acylamino groups (preferably with a carbon number of 2 to 30, more preferably with a carbon number of 2 to 20, and especially preferably with a carbon number of 2 to 10, such as acetylamino and benzoylamino); alkoxycarbonylamino groups (preferably with a carbon number of 2 to 30, more preferably with a carbon number of 2 to 20, and especially preferably with a carbon number of 2 to 12, such as methoxycarbonylamino); aryloxycarbonylamino groups (preferably with a carbon number of 7 to 30, more preferably with a carbon number of 7 to 20, and especially preferably with a carbon number of 7 to 12, such as phenyloxycarbonylamino); sulfonyl amino groups (preferably with a carbon number of 1 to 30, more preferably with a carbon number of 1 to 20, and especially preferably with a carbon number of 1 to 12, such as methanesulfonyl amino and benzenesulfonyl amino); sulfamoyl groups (preferably with a carbon number of 0 to 30, more preferably with a carbon number of 0 to 20, and especially preferably with a carbon number of 0 to 12, such as sulfamoyl, methylsulfamoyl, dimethylsulfamoyl, and phenylsulfamoyl); carbamoyl groups (preferably with a carbon number of 1 to 30, more preferably with a carbon number of 1 to 20, and especially preferably with a carbon number of 1 to 12, such as carbamoyl, methylcarbamoyl, diethylcarbamoyl, and phenylcarbamoyl); alkylthio groups (preferably with a carbon number of 1 to 30, more preferably with a carbon number of 1 to 20, and especially preferably with a carbon number of 1 to 12, such as methylthio and ethylthio); arylthio groups (preferably with a carbon number of 6 to 30, more preferably with a carbon number of 6 to 20, and especially preferably with a carbon number of 6 to 12, such as phenylthio); heterocyclic thio groups (preferably with a carbon number of 1 to 30, more preferably with a carbon number of 1 to 20, and especially preferably with a carbon number of 1 to 12, such as pyridylthio, 2-benzimidazolylthio, 2-benzoxazolylthio, and 2-benzothiazolylthio); sulfonyl groups (preferably with a carbon number of 1 to 30, more preferably with a carbon number of 1 to 20, and especially preferably with a carbon number of 1 to 12, such as mesyl and tosyl); sulfinyl groups (preferably with a carbon number of 1 to 30, more preferably with a carbon number of 1 to 20, and especially preferably with a carbon number of 1 to 12, such as methanesulfinyl and benzenesulfinyl); ureido groups (preferably with a carbon number of 1 to 30, more preferably with a carbon number of 1 to 20, and especially preferably with a carbon number of 1 to 12, such as ureido, methylureido, and phenylureido); phosphoric amide groups (preferably with a carbon number of 1 to 30, more preferably with a carbon number of 1 to 20, and especially preferably with a carbon number of 1 to 12, such as diethylphosphoramide and phenylphosphoramide); a hydroxy group; a mercapto group; halogen atoms (such as a fluorine atom, chlorine atom, bromine atom, and iodine atom); a cyano group; a sulfo group; a carboxyl group; a nitro group; a hydroxamic acid group; a sulfino group; a hydrazino group; an imino group; heterocyclic groups (also including heteroaryl groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidinyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group); silyl groups (preferably with a carbon number of 3 to 40, more preferably with a carbon number of 3 to 30, and especially preferably with a carbon number of 3 to 24, such as trimethylsilyl and triphenylsilyl); silyloxy groups (preferably with a carbon number of 3 to 40, more preferably with a carbon number of 3 to 30, and especially preferably with a carbon number of 3 to 24, such as trimethylsilyloxy and triphenylsilyloxy); and phosphoryl groups (such as a diphenylphosphoryl group and a dimethylphosphoryl group). These substituents may be further substituted, and examples of the further substituent include groups selected from the Substituent Group A described above. In addition, the substituents that have been substituted with a substituent may be further substituted, and examples of these further substituents include groups selected from the Substituent Group A described above. Furthermore, the substituents that substitute for substituents that substitute for substituents may be further substituted, and examples of these further substituents include groups selected from the aforementioned Substituent Group A.

<<Substituent Group B>>

Examples [of Substituent Group B] include alkyl groups (preferably with a carbon number of 1 to 30, more preferably with a carbon number of 1 to 20, and especially preferably with a carbon number of 1 to 10, such as a methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as a vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthryl); a cyano group; heterocyclic groups (also including heteroaryl groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidinyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group). These substituents may be further substituted, and examples of the further substituent include groups selected from the Substituent Group B described above. Moreover, the substituents that have been substituted with a substituent may be further substituted, and examples of these further substituents include groups selected from the Substituent Group B described above. In addition, the substituents that substitute for substituents that substitute for substituents may be further substituted, and examples of these further substituents include groups selected from the Substituent Group B described above.

The substituent can be suitably selected for the purpose of controlling the emission wavelength or potential, but if the wavelength is to be shortened, [the substituent is] preferably an electron-donating group, a fluorine atom, or an aromatic ring group; for example, an alkyl group, a dialkylamino group, an alkoxy group, a fluorine atom, an aryl group, a heteroaryl group, or the like is selected. Furthermore, if the wavelength is to be lengthened, [the substituent is] preferably an electron-withdrawing group; for example, a cyano group, a perfluoroalkyl group, or the like is selected.

The substituent on nitrogen is preferably an alkyl group, an aryl group, or a heteroaryl group, and from the standpoint of stability of the complex, an alkyl group or an aryl group is preferable.

The aforementioned substituents may be linked to each other to form a condensed ring. Examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. These rings thus formed may have a substituent, and examples of the substituent include the aforementioned substituent on a carbon atom and substituent on a nitrogen atom.

$B_1$ represents a five- or six-membered ring containing $Z^2$ and a carbon atom. Examples of the five- or six-membered ring formed by $B_1$, $Z^2$, and a carbon atom include a benzene ring, a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, and a furan ring.

From the standpoints of the stability of the complex, control of emission wavelength, and luminescent quantum yield, the five- or six-membered ring formed by $B_1$, $Z^2$, and a carbon atom is preferably a benzene ring, a pyridine ring, a pyrazine ring, an imidazole ring, a pyrazole ring, or a thiophene ring, more preferably a benzene ring, a pyridine ring, or a pyrazole ring, and even more preferably a benzene ring or a pyridine ring.

The aforementioned five- or six-membered ring formed by $B_1$, $Z^2$, and a carbon atom may have a substituent. [A substituent from] the aforementioned Substituent Group A can be used as a substituent on a carbon atom, and [a substituent from] the aforementioned Substituent Group B can be used as a substituent on a nitrogen atom. The substituent on a carbon atom is preferably an alkyl group, a perfluoroalkyl group, an aryl group, a heteroaryl group, a dialkylamino group, a diarylamino group, an alkoxy group, a cyano group, or a fluorine atom.

The substituent can be suitably selected for the purpose of controlling the emission wavelength or potential, but if the wavelength is to be lengthened, [the substituent is] preferably an electron-donating group or an aromatic ring group; for example, an alkyl group, a dialkylamino group, an alkoxy group, an aryl group, a heteroaryl group, or the like is selected. Furthermore, if the wavelength is to be shortened, [the substituent is] preferably an electron-withdrawing group; for example, a fluorine atom, a cyano group, a perfluoroalkyl group, or the like is selected.

A substituent on a nitrogen atom is preferably an alkyl group, an aryl group, or a heteroaryl group, and from the standpoint of the stability of the complex, an alkyl group or an aryl group is preferable. The aforementioned substituents may be linked to each other to form a condensed ring. Examples of the ring thus formed include a benzene ring, a pyridine ring, a pyrazine ring, a pyridazine ring, a pyrimidine ring, an imidazole ring, an oxazole ring, a thiazole ring, a pyrazole ring, a thiophene ring, and a furan ring. These rings thus formed may have a substituent, and examples of the substituent include the aforementioned substituent on a carbon atom and substituent on a nitrogen atom.

Moreover, a substituent for the aforementioned five- or six-membered heterocycle formed by $A_1$, $Z^1$, and a nitrogen atom and a substituent for the aforementioned five- or six-membered ring formed by $B_1$, $Z^2$, and a carbon atom may be linked together to form a condensed ring similar to the one described above.

Various ligands are known as ligands expressed by (X—Y) used in metal complexes in known prior art, examples of which include the ligands described in "Photochemistry and Photophysics of Coordination Compounds," by H. Yersin, Springer-Verlag Co. (1987) and in "Yuuki Kinzoku Kagaku—Kiso to Ouyou [*Organometallic Chemistry—Fundamentals and Applications*]," by Akio Yamamoto, Shokabo Publishing Co. (1982) (for example, halogen ligands, (preferably a chlorine ligand), nitrogen-containing heteroaryl ligands (such as bipyridyl and phenanthroline), and diketone ligands (such as acetylacetone)).

A ligand expressed by (X—Y) is preferably [any of compounds expressed by] General Formulas I-1 to I-13 below, but the present invention is not limited to or by these:

[Nineteenth Chemical Formula]

(1-1)
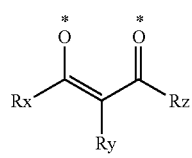

(1-2)
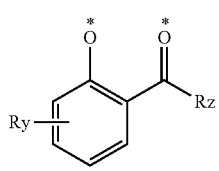

(1-3)
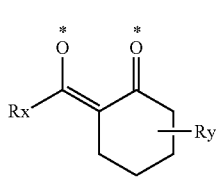

(1-4)
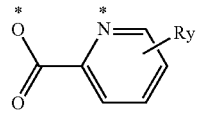

(1-5)
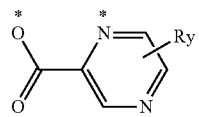

(1-6)
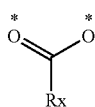

(1-7)
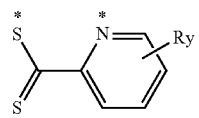

(1-8)
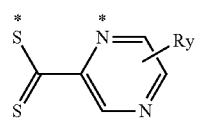

(1-9)
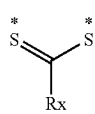

(1-10)
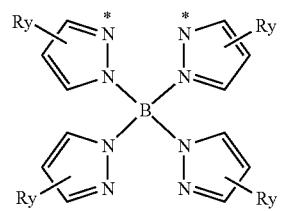

(1-11)
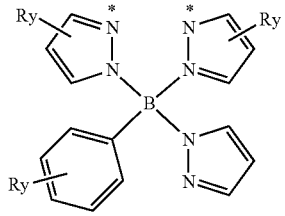

(1-12)
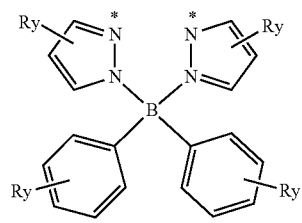

-continued (1-13)

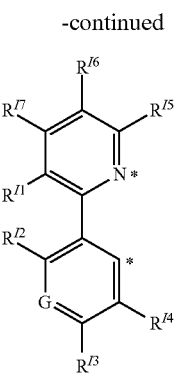

The asterisk indicates the coordination position to iridium (Ir) in General Formula E-1. Rx, Ry, and Rz represent each independently a hydrogen atom or a substituent. G represents C—R or a nitrogen atom. R represents a hydrogen atom or a substituent.

When Rx, Ry, and Rz represent a substituent, substituents selected from the aforementioned Substituent Group A can be cited as this substituent. Preferably, Rx and Rz are each independently an alkyl group, a perfluoroalkyl group, a fluorine atom, or an aryl group, more preferably a $C_1$ to $C_4$ alkyl group, a $C_1$ to $C_4$ perfluoroalkyl group, a fluorine atom, or a phenyl group which may be substituted, and most preferably a methyl group, an ethyl group, a trifluoromethyl group, a fluorine atom, or a phenyl group. Ry is preferably a hydrogen atom, an alkyl group, a perfluoroalkyl group, a fluorine atom, or an aryl group, more preferably a hydrogen atom, a $C_1$ to $C_4$ alkyl group, or a phenyl group which may be substituted, and most preferably a hydrogen atom or a methyl group. It is conceivable that these ligands will not be a site where charges are transported in an element or where electrons are concentrated by excitation, so it is sufficient if Rx, Ry, and Rz are a chemically stable substituent, and there is no influence on the effect of the present invention.

$R^{J1}$ to $R^{J7}$ in General Formula I-13 preferably represent substituents selected from Substituent Group A and may further have a substituent A.

G represents C—R or a nitrogen atom. If R represents a substituent, examples of this substituent include substituents selected from the aforementioned Substituent Group A.

Any two of the R [groups] when $R^{J1}$ to $R^{J7}$ and G represent C—R may bond together to form a condensed four- to seven-membered ring. This condensed four- to seven-membered ring may be a cycloalkyl, aryl, or heteroaryl, and this condensed four- to seven-membered ring may further have a substituent.

The preferred ranges of $R^{J1}$ to $R^{J7}$ are the same as the preferred ranges of $R^{T1}$ to $R^{T7}$ in General Formula E-3 (described later).

G is preferably C—R, and R is preferably a hydrogen atom or an aryl group, more preferably a hydrogen atom or a $C_6$-$C_{30}$ substituted or unsubstituted aryl group (such as a phenyl group, a tolyl group, or a naphthyl group), and especially preferably a hydrogen atom or a phenyl group.

(X—Y) is more preferably I-1, I-4, or I-13, with I-1 and I-13 being especially favorable. Complexes having these ligands can be synthesized in the same manner as in known synthesis examples by using a corresponding ligand precursor. For example, they can be similarly synthesized by the method described on page 46 of International Laid-Open Patent Application 2009-073245.

A preferred mode of the iridium (Ir) complex expressed by General Formula E-1 is an iridium (Ir) complex expressed by General Formula E-2.

[Twentieth Chemical Formula]

(E-2)

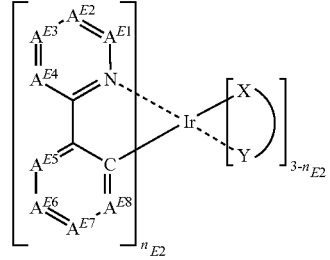

In General Formula E-2, $A^{E1}$ to $A^{E8}$ represent each independently a nitrogen atom or C—$R^E$.

$R^E$ represents a hydrogen atom or a substituent.

(X—Y) represents a monoanionic bidentate ligand.

$n_{E2}$ represents an integer from 1 to 3.

$A^{E1}$ to $A^{E8}$ represent each independently a nitrogen atom or C—$R^E$. $R^E$ represents a hydrogen atom or a substituent, and the $R^E$ [groups] may be linked to each other to form a ring. Examples of a ring thus formed include those that are the same as for the condensed ring described in relation to General Formula E-1 above. As a substituent expressed by $R^E$, those listed as examples of the aforementioned Substituent Group A can be used.

$A^{E1}$ to $A^{E4}$ are preferably C—$R^E$, and if $A^{E1}$ to $A^{E4}$ are C—$R^E$, the $R^E$ [groups] of $A^{E3}$ are preferably a hydrogen atom, an alkyl group, an aryl group, an amino group, an alkoxy group, an aryloxy group, a fluorine atom, or a cyano group, more preferably a hydrogen atom, an alkyl group, an amino group, an alkoxy group, an aryloxy group, or a fluorine atom, and especially preferably a hydrogen atom or a fluorine atom. The $R^E$ [groups] of $A^{E1}$, $A^{E2}$, $A^{E4}$ are preferably a hydrogen atom, an alkyl group, an aryl group, an amino group, an alkoxy group, an aryloxy group, a fluorine atom, or a cyano group, more preferably a hydrogen atom, an alkyl group, an amino group, an alkoxy group, an aryloxy group, or a fluorine atom, and especially preferably a hydrogen atom.

$A^{E5}$ to $A^{E8}$ are preferably C—$R^E$, and if $A^{E5}$ to $A^{E8}$ are C—$R^E$, $R^E$ is preferably a hydrogen atom, an alkyl group, a perfluoroalkyl group, an aryl group, a heteroaryl group, a dialkylamino group, a diarylamino group, an alkyloxy group, a cyano group, or a fluorine atom, more preferably a hydrogen atom, an alkyl group, a perfluoroalkyl group, an aryl group, a dialkylamino group, a cyano group, or a fluorine atom, and even more preferably a hydrogen atom, an alkyl group, a trifluoromethyl group, or a fluorine atom. In addition, if possible, the substituents may be linked to each other to form a condensed ring structure. When the emission wavelength is shifted to the short wavelength side, it is preferable for $A^{E6}$ to be a nitrogen atom.

(X—Y) and $n_{E2}$ are defined the same as (X—Y) and $n_{E1}$ in General Formula E-1, and the preferred ranges are also the same.

A more preferred form of the compound expressed by General Formula E-2 above is a compound expressed by General Formula E-3 below:

[Twenty-First Chemical Formula]

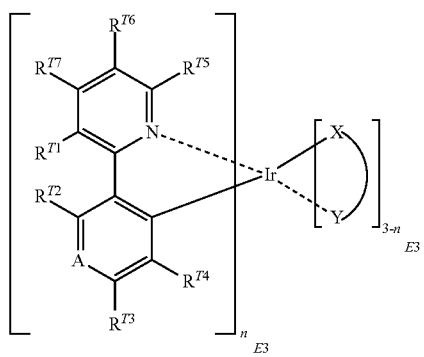

(E-3)

In General Formula E-3, $R^{T1}$, $R^{T2}$, $R^{T3}$, $R^{T4}$, $R^{T5}$, $R^{T6}$ and $R^{T7}$ represent each independently a hydrogen atom, an alkyl group, a cycloalkyl group, an alkenyl group, an alkynyl group, —CN, a perfluoroalkyl group, a trifluorovinyl group, —$CO_2R$, —C(O)R, —$NR_2$, —$NO_2$, —OR, a halogen atom, an aryl group, or a heteroaryl group, and may further have a substituent. The R [groups] represent each independently a hydrogen atom, an alkyl group, a perhaloalkyl group, an alkenyl group, an alkynyl group, a heteroalkyl group, an aryl group, or a heteroaryl group.

A represents CR' or a nitrogen atom, and R' represents a hydrogen atom, an alkyl group, a cycloalkyl group, an alkenyl group, an alkynyl group, —CN, a perfluoroalkyl group, a trifluorovinyl group, —$CO_2R$, —C(O)R, —$NR_2$, —$NO_2$, —OR, a halogen atom, an aryl group, or a heteroaryl group, and may further have a substituent. The R [groups] represent each independently a hydrogen atom, an alkyl group, a perhaloalkyl group, an alkenyl group, an alkynyl group, a heteroalkyl group, an aryl group, or a heteroaryl group.

Any two of $R^{T1}$ to $R^{T7}$ and R' may bind together to form a condensed four- to seven-membered ring, this condensed four- to seven-membered ring is a cycloalkyl, aryl, or heteroaryl, and this condensed four- to seven-membered ring may further have a substituent. Of these, it is preferable for $R^{T1}$ and $R^{T7}$ or for $R^{T5}$ and $R^{T6}$ to form a benzene ring by annulation, and it is especially preferable for $R^{T5}$ and $R^{T6}$ to form a benzene ring by annulation.

(X—Y) represents a monoanionic bidentate ligand. $n_{E3}$ represents an integer from 1 to 3.

The alkyl group may have a substituent and may be either saturated or unsaturated, and examples of groups that may be substituted include the aforementioned substituents A. The alkyl groups expressed by $R^{T1}$ to $R^{T7}$ and R' are preferably alkyl groups with a total number of carbon atoms of 1 to 8 and more preferably alkyl groups with a total number of carbon atoms of 1 to 6, examples of which include a methyl group, ethyl group, i-propyl group, cyclohexyl group, and t-butyl group, with a methyl group being especially preferable.

The cycloalkyl group may have a substituent and may be either saturated or unsaturated, and examples of groups that may be substituted include the aforementioned substituents A. The cycloalkyl groups expressed by $R^{T1}$ to $R^{T7}$ and R' are preferably cycloalkyl groups with 4 to 7 ring members and more preferably cycloalkyl groups with a total number of carbon atoms[3] of 5 or 6, examples of which include a cyclopentyl group and a cyclohexyl group.

[3] Translator's note: In the Japanese original document, the term for "ring members" and the term for "total number of carbon atoms" are used in the same phrase to specify the conditions being preferred, where only one or the other would be expected. Our translation faithfully reflects the Japanese source text.

The alkenyl group expressed by $R^{T1}$ to $R^{T7}$ and R' preferably has a carbon number of 2 to 30, more preferably a carbon number of 2 to 20, and especially preferably a carbon number of 2 to 10, examples including a vinyl, aryl, 1-propenyl, 1-isopropenyl, 1-butenyl, 2-butenyl, and 3-pentenyl.

The alkynyl group expressed by $R^{T1}$ to $R^{T7}$ and R' preferably has a carbon number of 2 to 30, more preferably a carbon number of 2 to 20, and especially preferably a carbon number of 2 to 10, examples including an ethynyl, propargyl, 1-propynyl, and 3-pentynyl.

Examples of the perfluoroalkyl group expressed by $R^{T1}$ to $R^{T7}$ and R' include the aforementioned alkyl groups in which all of the hydrogen atoms are substituted with fluorine atoms.

The aryl group expressed by $R^{T1}$ to $R^{T7}$ and R' is preferably a $C_6$-$C_{30}$ substituted or unsubstituted aryl group, examples including a phenyl group, tolyl group, and naphthyl group, with a phenyl group being especially favorable.

The heteroaryl group expressed by $R^{T1}$ to $R^{T7}$ and R' is preferably a $C_5$-$C_8$ heteroaryl group and more preferably a substituted or unsubstituted heteroaryl group with 5 or 6 members, examples including a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, and a 7-pyridoindolyl group. Preferable examples are a pyridyl group, a pyrimidinyl group, an imidazolyl group, and a thienyl group, and more preferable are a pyridyl group and a pyrimidinyl group.

$R^{T1}$ to $R^{T7}$ and R' are preferably a hydrogen atom, an alkyl group, a cyano group, a trifluoromethyl group, a perfluoroalkyl group, a dialkylamino group, a fluoro group, an aryl group, or a heteroaryl group, more preferably a hydrogen atom, an alkyl group, a cyano group, a trifluoromethyl group, a fluoro group, or an aryl group, and even more preferably a hydrogen atom, an alkyl group, or an aryl group.

Any two of $R^{T1}$ to $R^{T7}$ and R' may bind together to form a condensed four- to seven-membered ring, this condensed four- to seven-membered ring is a cycloalkyl, aryl, or heteroaryl, and this condensed four- to seven-membered ring may further have a substituent. The definitions and preferred ranges for the cycloalkyl, aryl, or heteroaryl thus formed are the same as for the cycloalkyl group, aryl group, and heteroaryl group defined by $R^{T1}$ to $R^{T7}$ and R'.

Furthermore, it is especially preferable when A represents CR', and also zero to two of the $R^{T1}$ to $R^{T7}$ and R' [groups] are an alkyl group or a phenyl group, while all of the remaining are hydrogen atoms. It is especially [more] preferable for zero to two of the $R^{T1}$ to $R^{T7}$ and R' [groups] to be an alkyl group and for all of the remaining to be hydrogen atoms. It is most preferable for zero to two of the $R^{T1}$ to $R^{T7}$ and R' [groups] to be a methyl group and for all of the remaining to be hydrogen atoms.

$n_{E3}$ is preferably 2 or 3. The ligand in the complex is preferably constituted by one or two types and more preferably by one type. When a reactive group is introduced into the complex molecule, it is also preferable for the ligand to be composed of two types from the standpoint of ease of synthesis.

(X—Y) is defined the same as (X—Y) in General Formula E-1, and the preferred ranges are also the same.

One of the preferred forms of the compound expressed by General Formula E-3 above is a compound expressed by General Formula E-4 below:

[Twenty-Second Chemical Formula]

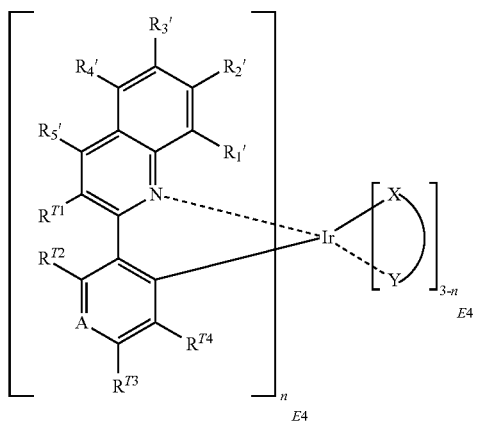

(E-4)

$R^{T1}$ to $R^{T4}$, A, (X—Y), and $n_{E4}$ in General Formula E-4 are defined the same as $R^{T1}$ to $R^{T4}$, A, (X—Y) and $n_{E3}$ in General Formula E-3, and the preferred ranges are also the same. $R_1'$ to $R_5'$ represent each independently a hydrogen atom, an alkyl group, a cycloalkyl group, an alkenyl group, an alkynyl group, a cyano group, a perfluoroalkyl group, a trifluorovinyl group, —$CO_2R$, —C(O)R, —$NR_2$, —$NO_2$, —OR, a halogen atom, an aryl group, or a heteroaryl group, and may further have a substituent. The R [groups] represent each independently a hydrogen atom, an alkyl group, a perhaloalkyl group, an alkenyl group, an alkynyl group, a heteroalkyl group, an aryl group, or a heteroaryl group.

Any two of $R_1'$ to $R_5'$ may bind together to form a condensed four- to seven-membered ring, this condensed four- to seven-membered ring is a cycloalkyl, aryl, or heteroaryl, and this condensed four- to seven-membered ring may further have a substituent.

Moreover, the preferred ranges for $R_1'$ to $R_5'$ are the same as those for $R^{T1}$ to $R^{T7}$ and R' in General Formula E-3. In addition, it is especially preferable when A represents CR', and also zero to two of the $R^{T1}$ to $R^{T4}$, R', and $R_1'$ to $R_5'$ [groups] are an alkyl group or a phenyl group, while all of the remaining are hydrogen atoms, and more preferable is when zero to two of the $R^{T1}$ to $R^{T4}$, R', and $R_1'$ to $R_5'$ [groups] are an alkyl group, while all of the remaining are hydrogen atoms.

Another preferred form of the compound expressed by General Formula E-3 above is a compound expressed by General Formula E-5 below:

[Twenty-Third Chemical Formula]

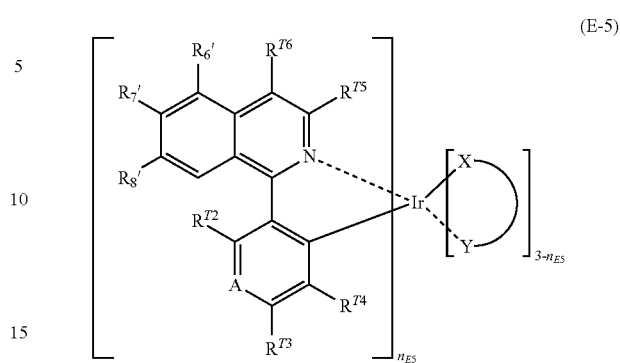

(E-5)

$R^{T2}$ to $R^{T6}$, A, (X—Y), and $n_{E5}$ in General Formula E-5 are defined the same as $R^{T2}$ to $R^{T6}$, A, (X—Y), and $n_{E3}$ in General Formula E-3, and the preferred ranges are also the same. $R_6'$ to $R_8'$ represent each independently a hydrogen atom, an alkyl group, a cycloalkyl group, an alkenyl group, an alkynyl group, a cyano group, a perfluoroalkyl group, a trifluorovinyl group, —$CO_2R$, —C(O)R, —$NR_2$, —$NO_2$, —OR, a halogen atom, an aryl group, or a heteroaryl group, and may further have a substituent. The R [groups] represent each independently a hydrogen atom, an alkyl group, a perhaloalkyl group, an alkenyl group, an alkynyl group, a heteroalkyl group, an aryl group, or a heteroaryl group.

Any two of $R^{T5}$, $R^{T6}$, and $R_6'$ to $R_8'$ may bind together to form a condensed four- to seven-membered ring, this condensed four- to seven-membered ring is a cycloalkyl, aryl, or heteroaryl, and this condensed four- to seven-membered ring may further have a substituent.

In addition, the preferred ranges for $R_6'$ to $R_8'$ are the same as those for $R^{T1}$ to $R^{T7}$ and R' in General Formula E-3. Furthermore, it is especially preferable when A represents CR', and also zero to two of the $R^{T2}$ to $R^{T6}$, R', and $R_6'$ to $R_8'$ [groups] are an alkyl group or a phenyl group, while all of the remaining are hydrogen atoms, and more preferable is when zero to two of the $R^{T2}$ to $R^{T6}$, R', and $R_6'$ to $R_8'$ [groups] are an alkyl group, while all of the remaining are hydrogen atoms.

When a phosphorescent material expressed by General Formula E-4 or E-5 is used, the compound expressed by General Formula 1 is preferably included in the light-emitting layer or hole blocking layer and more preferably included in the light-emitting layer.

Another preferred form of the compound expressed by General Formula E-1 is a compound expressed by General Formula E-6 below:

[Twenty-Fourth Chemical Formula]

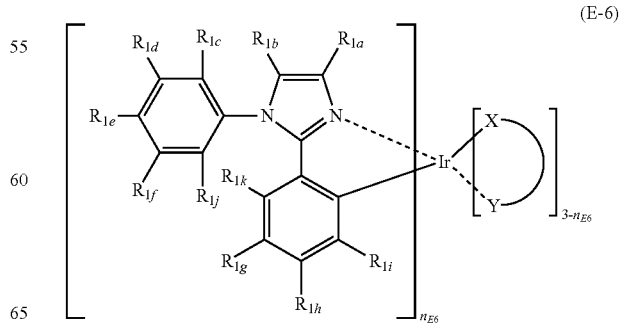

(E-6)

In General Formula E-6, $R_{1a}$ to $R_{1k}$ represent each independently a hydrogen atom, an alkyl group, a cycloalkyl group, an alkenyl group, an alkynyl group, a cyano group, a perfluoroalkyl group, a trifluorovinyl group, $-CO_2R$, $-C(O)R$, $-NR_2$, $-NO_2$, $-OR$, a halogen atom, an aryl group, or a heteroaryl group, and may further have a substituent. The R [groups] represent each independently a hydrogen atom, an alkyl group, a perhaloalkyl group, an alkenyl group, an alkynyl group, a heteroalkyl group, an aryl group, or a heteroaryl group.

Any two of $R_{1a}$ to $R_{1k}$ may bind together to form a condensed four- to seven-membered ring, this condensed four- to seven-membered ring is a cycloalkyl, aryl, or heteroaryl, and this condensed four- to seven-membered ring may further have a substituent.

(X—Y) represents a monoanionic bidentate ligand.

$n_{E6}$ represents an integer from 1 to 3.

The preferred ranges for $R_{1a}$ to $R_{1k}$ in General Formula E-6 are the same as those for $R^{T1}$ to $R^{T7}$ and R' in General Formula E-3. Furthermore, it is especially preferable for zero to two of the $R_{1a}$ to $R_{1k}$ [groups] to be an alkyl group or a phenyl group and for all of the remaining to be hydrogen atoms, and it is more preferable for zero to two of the $R_{1a}$ to $R_{1k}$ [groups] to be an alkyl group and for all of the remaining to be hydrogen atoms.

It is especially preferable when $R_{1j}$ and $R_{1k}$ are linked together to form a single bond.

The preferred ranges for (X—Y) and $n_{E6}$ are the same as those for (X—Y) and $n_{E3}$ in General Formula E-3.

A more preferred form of the compound expressed by General Formula E-6 is when [the compound] is expressed by General Formula E-7 below:

[Twenty-Fifth Chemical Formula]

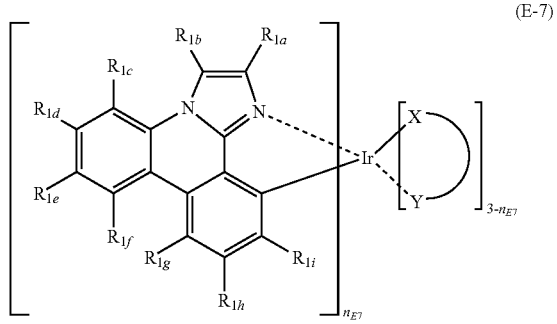

(E-7)

In General Formula E-7, $R_{1a}$ to $R_{1i}$ represent each independently a hydrogen atom, an alkyl group, a cycloalkyl group, an alkenyl group, an alkynyl group, a cyano group, a perfluoroalkyl group, a trifluorovinyl group, $-CO_2R$, $-C(O)R$, $-NR_2$, $-NO_2$, $-OR$, a halogen atom, an aryl group, or a heteroaryl group, and may further have a substituent. The R [groups] represent each independently a hydrogen atom, an alkyl group, a perhaloalkyl group, an alkenyl group, an alkynyl group, a heteroalkyl group, an aryl group, or a heteroaryl group.

Any two of $R_{1a}$ to $R_{1k}$ [sic][4] may bind together to form a condensed four- to seven-membered ring, this condensed four- to seven-membered ring is a cycloalkyl group, an aryl group, or a heteroaryl group, and this condensed four- to seven-membered ring may further have a substituent.

[4] Translator's note: apparent error in the original; "$R_{1a}$ to $R_{1k}$" should be "$R_{1a}$ to $R_{1i}$."

(X—Y) represents a monoanionic bidentate ligand.

$n_{E7}$ represents an integer from 1 to 3.

The definitions and preferred ranges for $R_{1a}$ to $R_{1i}$ in General Formula E-7 are the same as those for $R_{1a}$ to $R_{1i}$ in General Formula E-6. Furthermore, it is especially preferable for zero to two of the $R_{1a}$ to $R_{1i}$ [groups] to be an alkyl group or an aryl group and for all of the remaining to be hydrogen atoms. The definitions and preferred ranges for (X—Y) and $n_{E7}$ are the same as those for (X—Y) and $n_{E3}$ in General Formula E-3.

When a phosphorescent material expressed by General Formula E-6 or E-7 is used, the compound expressed by General Formula 1 is preferably included in the light-emitting layer or hole blocking layer.

One of the preferred forms of the compound expressed by General Formula E-3 above is a compound expressed by General Formula E-8 below:

[Twenty-Sixth Chemical Formula]

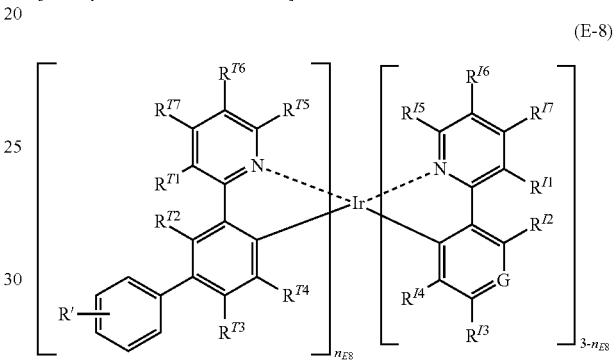

(E-8)

$R^{T1}$ to $R^{T7}$ in General Formula E-8 are defined the same as those in General Formula E-3, and the preferred ranges are also the same. $R^{I1}$ to $R^{I7}$ and G are defined the same as those in the ligand (I-13), and the preferred ranges are also the same. R' represents a hydrogen atom or a substituent selected from Substituent Group A. R' is preferably a hydrogen atom, an alkyl group, a cyano group, a trifluoromethyl group, a perfluoroalkyl group, a dialkylamino group, a fluorine atom, an aryl group, or a heteroaryl group, more preferably a hydrogen atom, an alkyl group, a fluorine atom, or an aryl group, and even more preferably a hydrogen atom. $n_{E8}$ represents an integer from 1 to 3 and is preferably 2 or 1.

One of the preferred forms of the compound expressed by General Formula E-3 above is a compound expressed by General Formula E-9 below:

[Twenty-Seventh Chemical Formula]

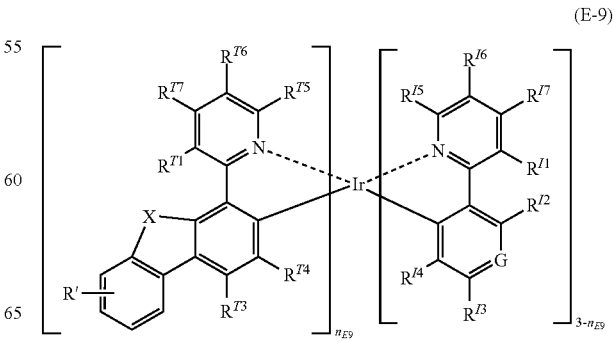

(E-9)

$R^{T1}$ and $R^{T3}$ to $R^{T7}$ in General Formula E-9 are defined the same as those in General Formula E-3, and the preferred ranges are also the same. $R^{J1}$ to $R^{J7}$ and G are defined the same as those in the ligand (I-13), and the preferred ranges are also the same. R' represents a hydrogen atom or a substituent selected from Substituent Group A. R' is preferably a hydrogen atom, an alkyl group, a cyano group, a trifluoromethyl group, a perfluoroalkyl group, a dialkylamino group, a fluorine atom, an aryl group, or a heteroaryl group, more preferably a hydrogen atom, an alkyl group, a fluorine atom, or an aryl group, and even more preferably a hydrogen atom. $n_{E9}$ represents an integer from 1 to 3 and is preferably 2 or 1. X represents an oxygen atom or a sulfur atom.

Preferred concrete examples of the compound expressed by General Formula E-1 are listed below, but [the compound] is in no way limited to these:

[Twenty-Eighth Chemical Formula]

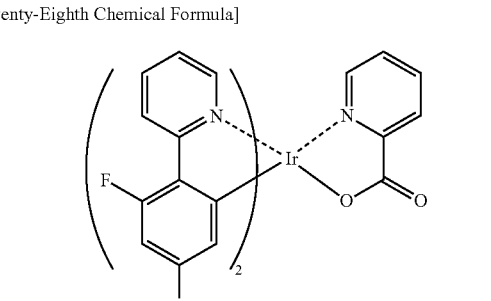

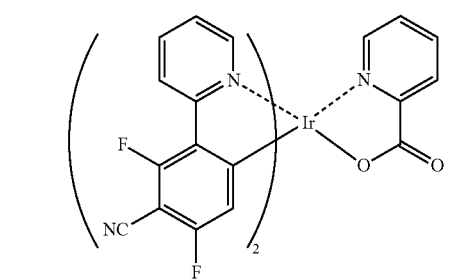

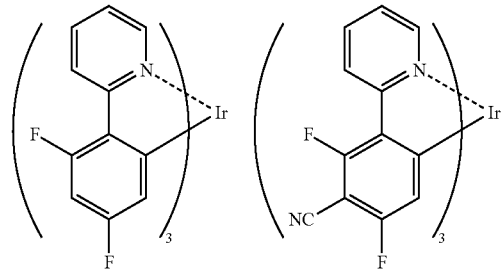

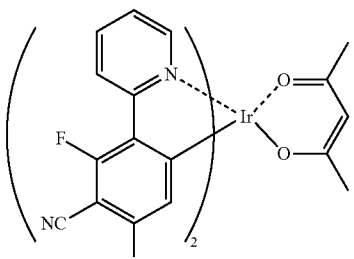

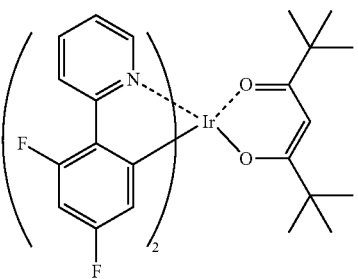

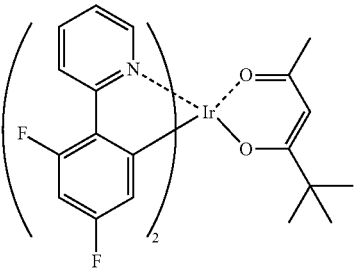

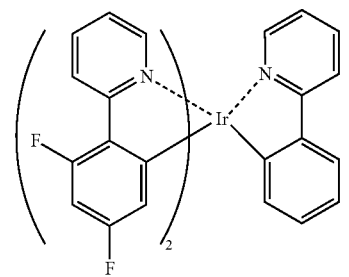

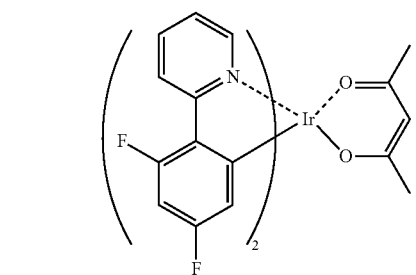

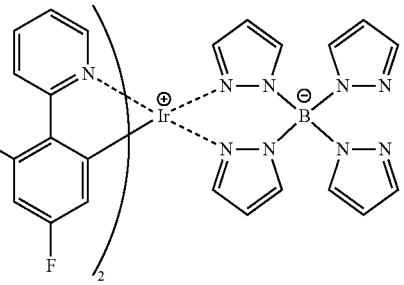

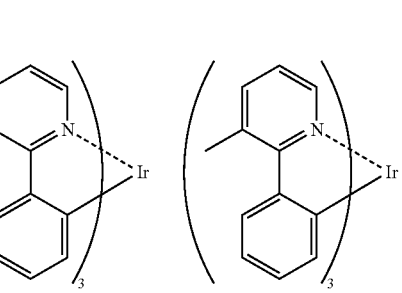

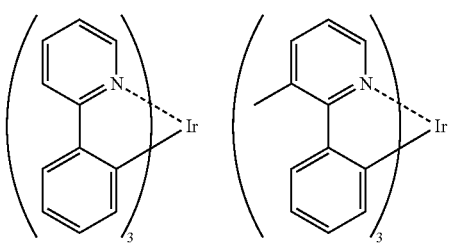

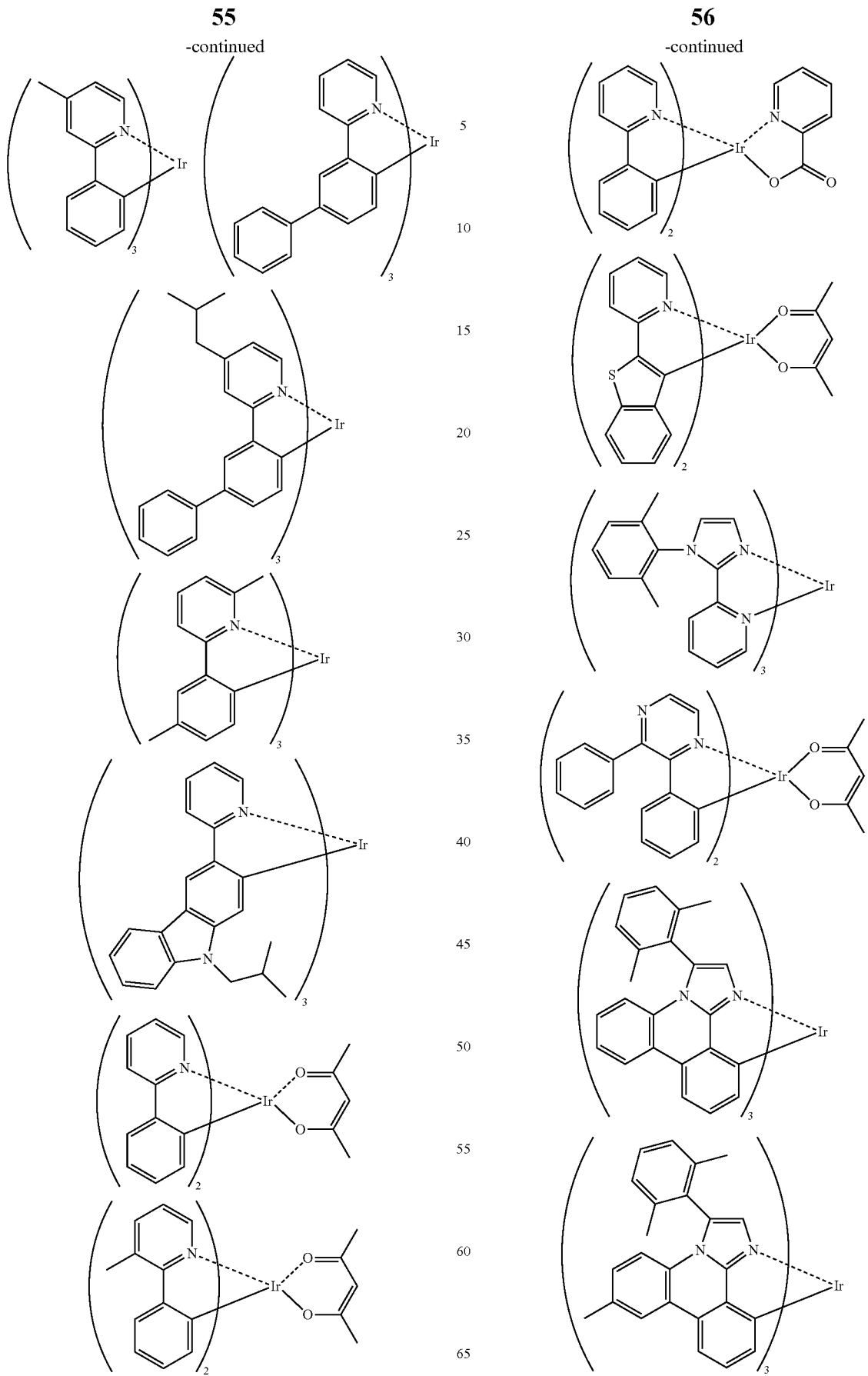

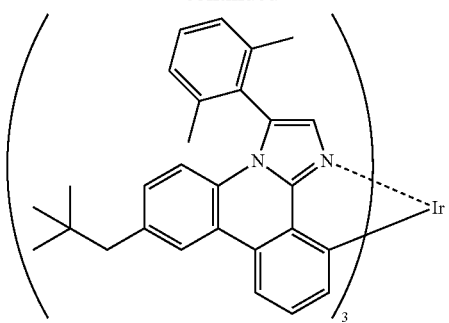
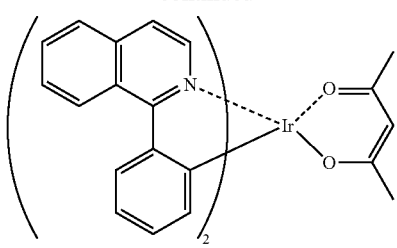
[Twenty-Ninth Chemical Formula]
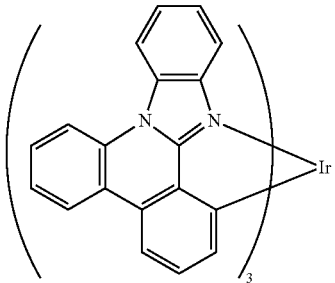
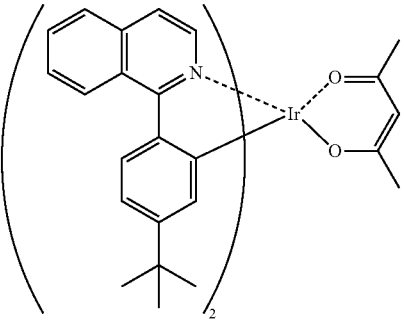
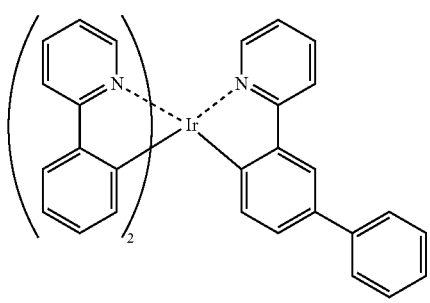
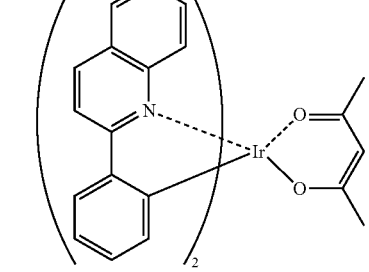
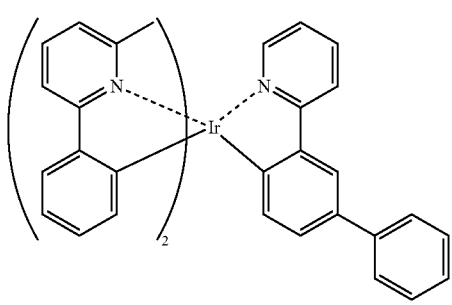
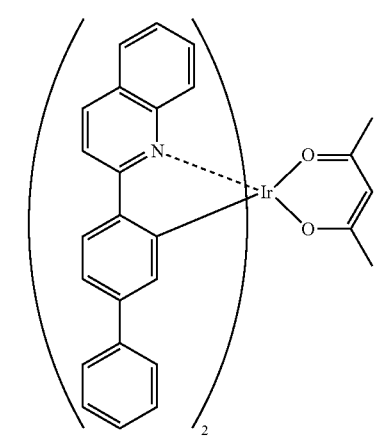
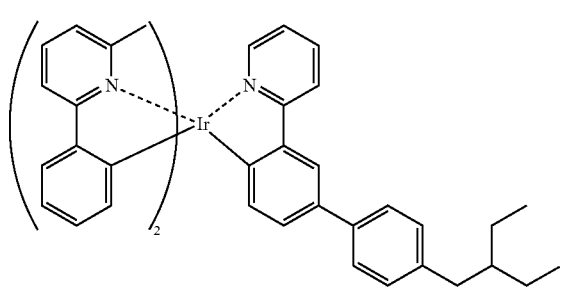
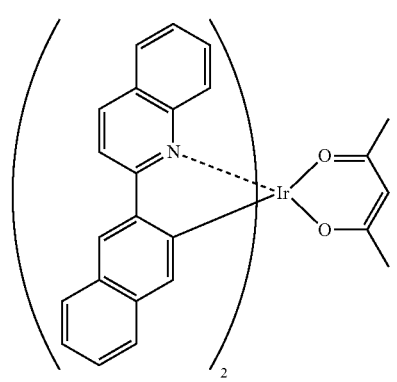

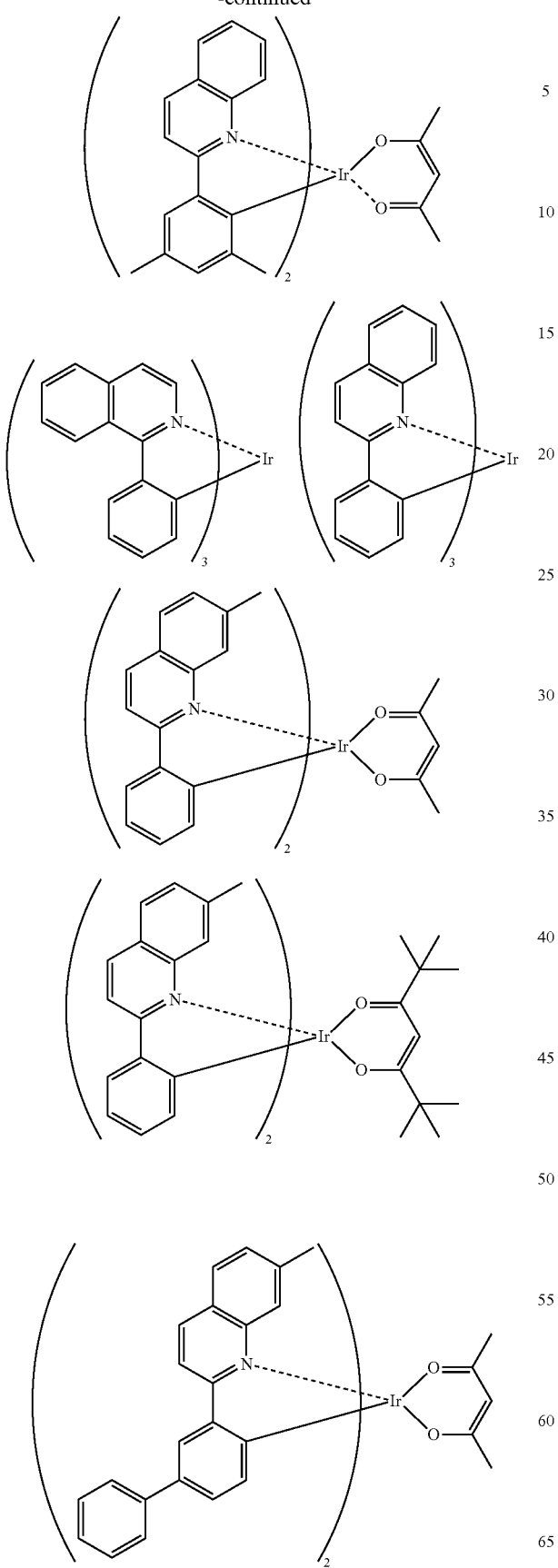

[Thirtieth Chemical Formula]
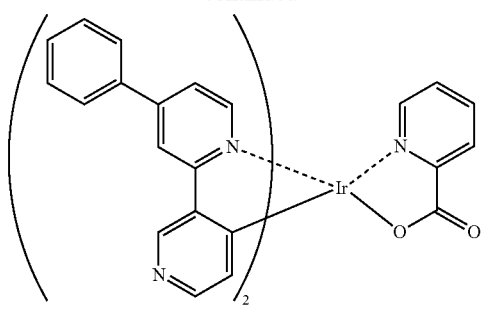
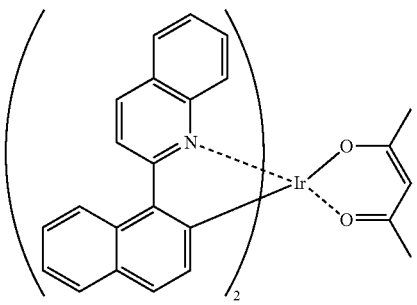
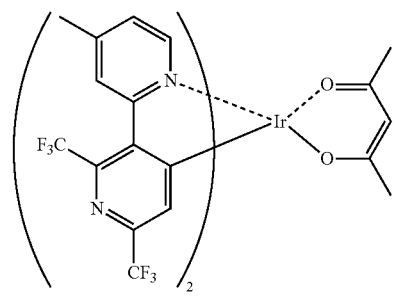
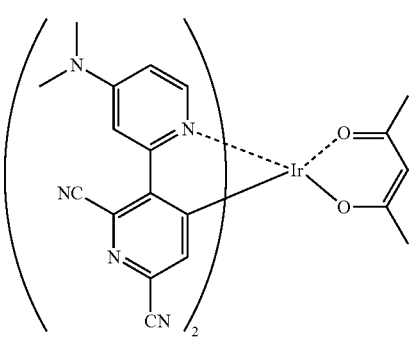
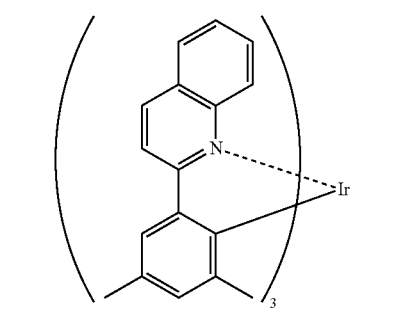
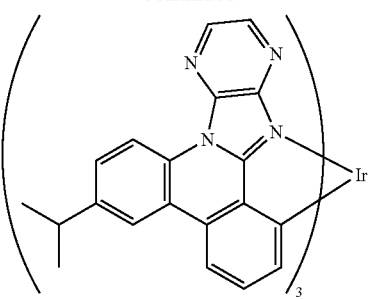
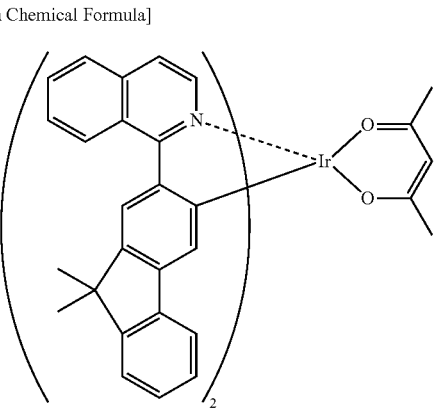
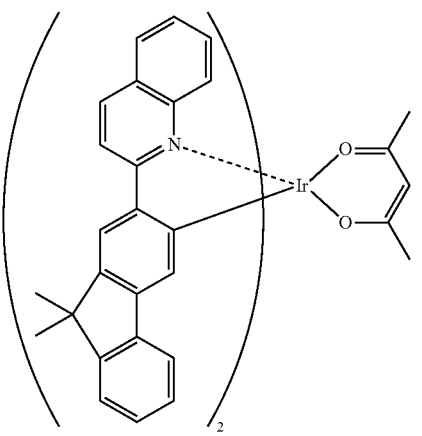
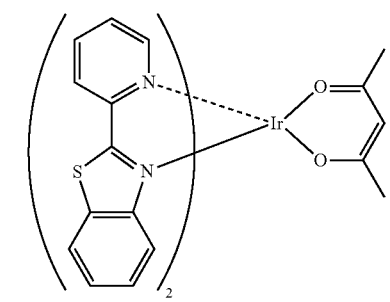

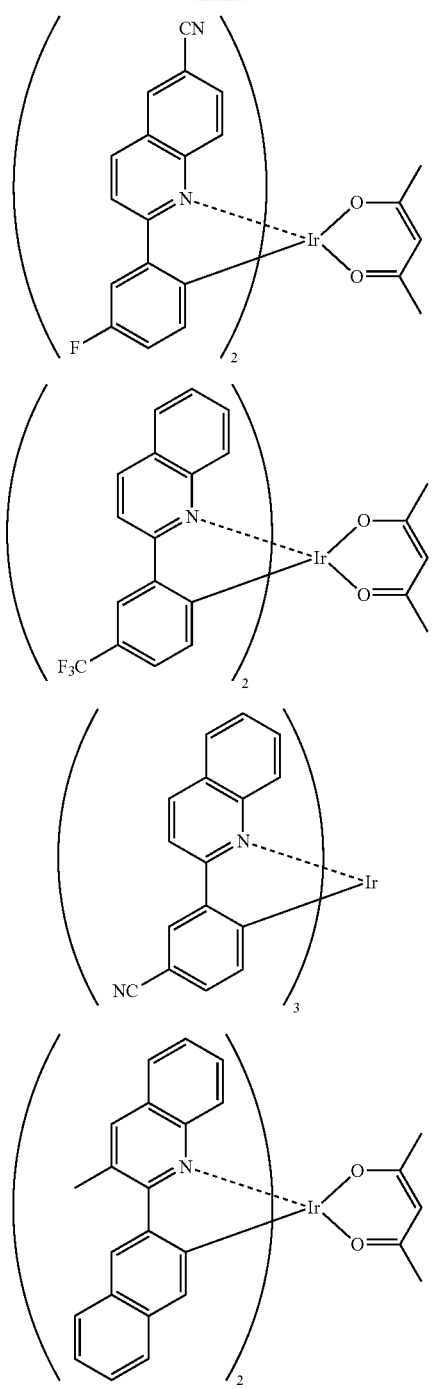
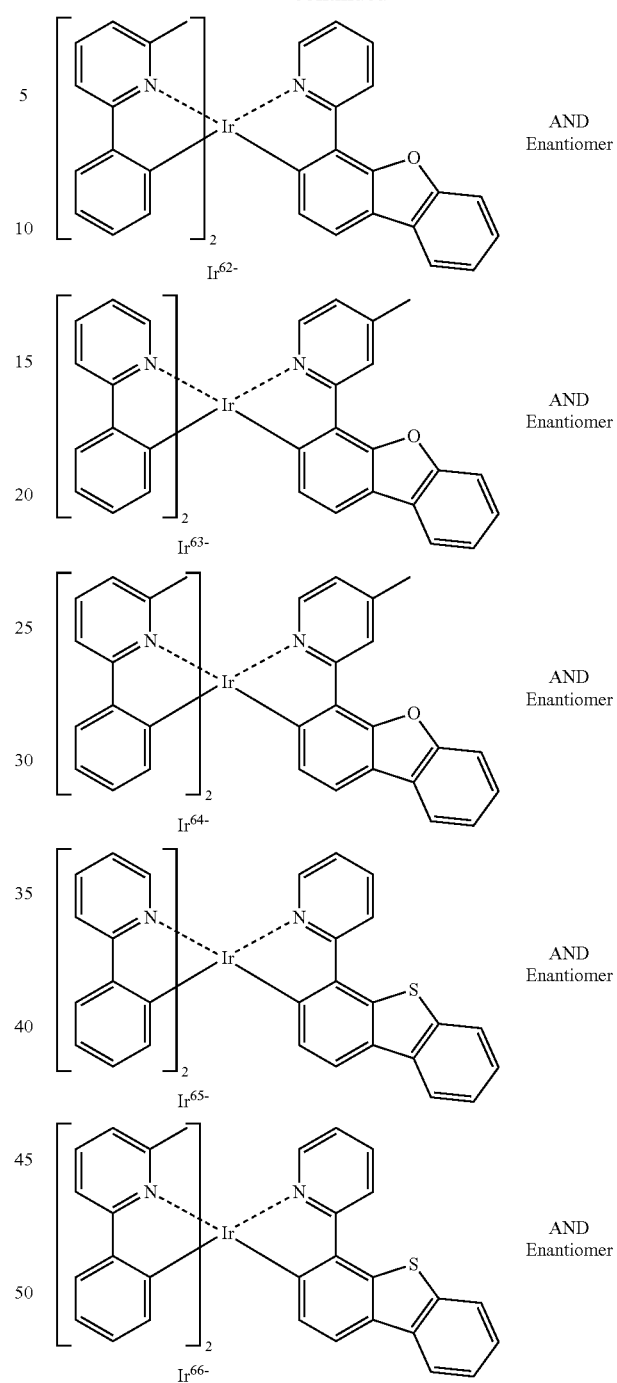
[Thirty-First Chemical Formula]
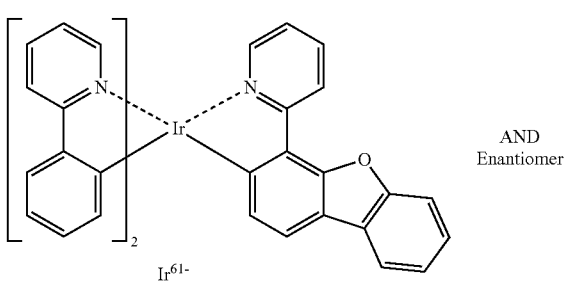
[Thirty-Second Chemical Formula]
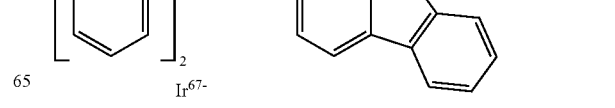

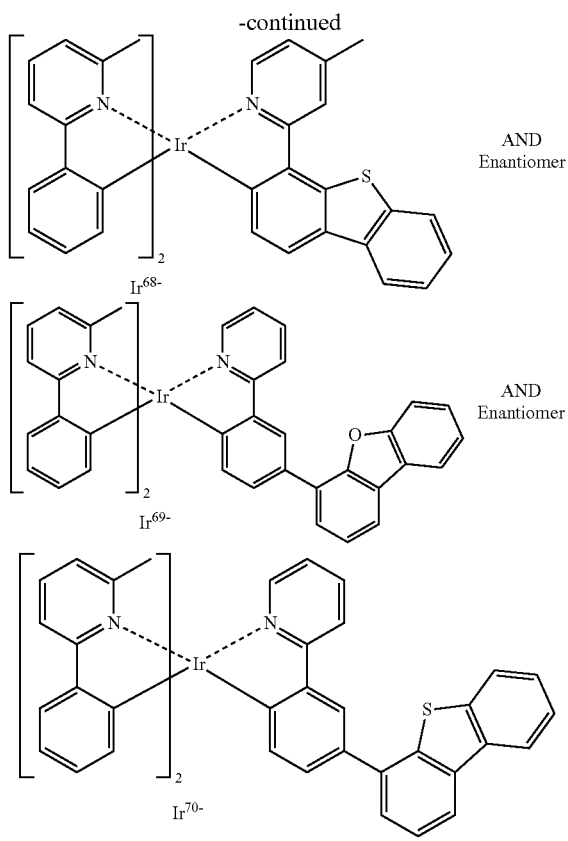

The compounds given as examples of the compound expressed by General Formula E-1 above can be synthesized by the method described in Japanese Laid-Open Patent Application 2009-99783 or by the various methods described in U.S. Pat. No. 7,279,232 and the like. After synthesis, it is preferable for purification by column chromatography, recrystallization, or the like to be performed, followed by sublimation purification. Sublimation purification not only allows organic impurities to be separated, but also allows inorganic salts, residual solvents, and the like to be effectively removed.

The compound expressed by General Formula E-1 is preferably contained in the light-emitting layer, but its application is not limited [to this], and [the compound] may be further contained in any of the organic layers.

The compound expressed by General Formula E-1 in the light-emitting layer is generally contained in the light-emitting layer in an amount of 0.1 to 50 wt % with respect to the total weight of the compounds which form the light-emitting layer, and from the standpoints of durability and external quantum efficiency, [the material] is preferably contained in an amount of 1 to 50 wt % and more preferably contained in an amount of 2 to 40 wt %.

In the present invention, it is especially preferable to combine a compound expressed by any of General Formulas 1 to 3 and 6 and a compound expressed by any of General Formulas E-1 to E-9 in the light-emitting layer and to use [this mixture].

The platinum (Pt) complex that can be used as the phosphorescent material is preferably a platinum (Pt) complex expressed by General Formula C-1 below:

[Thirty-Third Chemical Formula]

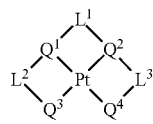

(C-1)

(In the formula, $Q^1$, $Q^2$, $Q^3$, and $Q^4$ represent each independently a ligand coordinated to platinum (Pt). $L^1$, $L^2$, and $L^3$ represent each independently a single bond or a divalent linking group.)

General Formula C-1 will now be described. $Q^1$, $Q^2$, $Q^3$, and $Q^4$ represent each independently a ligand coordinated to platinum (Pt). The bonds between the platinum (Pt) and $Q^1$, $Q^2$, $Q^3$, and $Q^4$ here may be covalent bonds, ion bonds, coordination bonds, or the like. The atom in $Q^1$, $Q^2$, $Q^3$, and $Q^4$ that is bound to the platinum (Pt) is preferably a carbon atom, a nitrogen atom, an oxygen atom, a sulfur atom, or a phosphorus atom. Of the atoms in $Q^1$, $Q^2$, $Q^3$, and $Q^4$ that are bound to the platinum (Pt), at least one is preferably a carbon atom, more preferably two are carbon atoms, and it is especially preferable if two are carbon atoms and two are nitrogen atoms.

$Q^1$, $Q^2$, $Q^3$, and $Q^4$ bound to platinum (Pt) by a carbon atom may be either an anionic ligand or a neutral ligand. Examples of anionic ligands include a vinyl ligand, an aromatic hydrocarbon ring ligand (such as a benzene ligand, a naphthalene ligand, an anthracene ligand, and a phenanthrene ligand), a heterocyclic ligand (such as a furan ligand, a thiophene ligand, a pyridine ligand, a pyrazine ligand, a pyrimidine ligand, a pyridazine ligand, a triazine ligand, a thiazole ligand, an oxazole ligand, a pyrrole ligand, an imidazole ligand, a pyrazole ligand, and a triazole ligand, as well as condensed rings containing these [ligands] (such as a quinoline ligand or a benzothiazole ligand)). Examples of neutral ligands include a carbene ligand.

The groups represented by $Q^1$, $Q^2$, $Q^3$, and $Q^4$ may have a substituent, and those listed as the aforementioned Substituent Group A can be used as the substituent as needed. Furthermore, the substituents may also be linked to each other (if $Q^3$ and $Q^4$ are linked, the result is a platinum (Pt) complex of a cyclic tetradentate ligand).

The groups expressed by $Q^1$, $Q^2$, $Q^3$, and $Q^4$ are preferably an aromatic hydrocarbon ring ligand bound to platinum (Pt) by a carbon atom, an aromatic heterocyclic ligand bound to platinum (Pt) by a carbon atom, a nitrogen-containing aromatic heterocyclic ligand bound to platinum (Pt) by a nitrogen atom, an acyloxy ligand, an alkyloxy ligand, an aryloxy ligand, a heteroaryloxy ligand, or a silyloxy ligand, more preferably an aromatic hydrocarbon ring ligand bound to platinum (Pt) by a carbon atom, an aromatic heterocyclic ligand bound to platinum (Pt) by a carbon atom, a nitrogen-containing aromatic heterocyclic ligand bound to platinum (Pt) by a nitrogen atom, an acyloxy ligand, or an aryloxy ligand, and even more preferably an aromatic hydrocarbon ring ligand bound to platinum (Pt) by a carbon atom, an aromatic heterocyclic ligand bound to platinum (Pt) by a carbon atom, a nitrogen-containing aromatic heterocyclic ligand bound to platinum (Pt) by a nitrogen atom, or an acyloxy ligand.

$L^1$, $L^2$, and $L^3$ represent a single bond or a divalent linking group. Examples of the divalent linking group represented by $L^1$, $L^2$, and $L^3$ include alkylene groups (such as methylene, ethylene, and propylene), arylene groups (phenylene and naphthalenediyl), heteroarylene groups (such as pyridinediyl and thiophenediyl), imino groups (—NR—) (such as a phenylimino group), an oxy group (—O—), a thio group (—S—), phosphinidene groups (—PR—) (such as a phenylphosphinidene group), and silylene groups (—SiRR'—) (such as a dimethylsilylene group and diphenylsilylene group), as well as combinations of these. Here, examples of R and R' include each independently an alkyl group and an aryl group. These linking groups may further have a substituent.

From the standpoints of the stability of the complex and luminescent quantum yield, $L^1$, $L^2$, and $L^3$ are preferably a single bond, an alkylene group, an arylene group, a heteroarylene group, an imino group, an oxy group, a thio group, or a silylene group, more preferably a single bond, an alkylene group, an arylene group, or an imino group, even more preferably a single bond, an alkylene group, or an arylene group, still more preferably a single bond, a methylene group, or a phenylene group, still more preferably a single bond or a di-substituted methylene group, and still more preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group.

$L^1$ is especially preferably a dimethylmethylene group, a diphenylmethylene group, or a cyclohexanediyl group, with a dimethylmethylene group being most preferable.

A single bond is most preferable as $L^2$ and $L^3$.

Of the platinum (Pt) complexes expressed by General Formula C-1, a platinum (Pt) complex expressed by General Formula C-2 below is more preferable:

[Thirty-Fourth Chemical Formula]

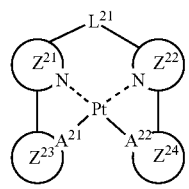

General Formula C-2

(In the formula, $L^{21}$ represents a single bond or a divalent linking group. $A^{21}$ and $A^{22}$ represent each independently a carbon atom or a nitrogen atom. $Z^{21}$ and $Z^{22}$ represent each independently a nitrogen-containing aromatic heterocycle. $Z^{23}$ and $Z^{24}$ represent each independently a benzene ring or an aromatic heterocycle.)

General Formula C-2 will now be described. $L^{21}$ is defined the same as $L^1$ in General Formula C-1 above, and the preferred ranges are also the same.

$A^{21}$ and $A^{22}$ represent each independently a carbon atom or a nitrogen atom. At least one of $A^{21}$ and $A^{22}$ is preferably a carbon atom. From the standpoint of the stability of the complex and the standpoint of luminescent quantum yield of the complex, it is preferable if $A^{21}$ and $A^{22}$ are both a carbon atom.

$Z^{21}$ and $Z^{22}$ represent each independently a nitrogen-containing aromatic heterocycle. Examples of the nitrogen-containing aromatic heterocycle represented by $Z^{21}$ and $Z^{22}$ include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring. From the standpoints of the stability of the complex, control of emission wavelength, and luminescent quantum yield, the ring expressed by $Z^{21}$ and $Z^{22}$ is preferably a pyridine ring, a pyrazine ring, an imidazole ring, or a pyrazole ring, more preferably a pyridine ring, an imidazole ring, or a pyrazole ring, even more preferably a pyridine ring or a pyrazole ring, and especially preferably a pyridine ring.

$Z^{23}$ and $Z^{24}$ represent each independently a benzene ring or an aromatic heterocycle. Examples of the nitrogen-containing aromatic heterocycle represented by $Z^{23}$ and $Z^{24}$ include a pyridine ring, a pyrimidine ring, a pyrazine ring, a pyridazine ring, a triazine ring, an imidazole ring, a pyrazole ring, an oxazole ring, a thiazole ring, a triazole ring, an oxadiazole ring, a thiadiazole ring, a thiophene ring, and a furan ring. From the standpoints of the stability of the complex, control of emission wavelength, and luminescent quantum yield, the ring represented by $Z^{23}$ and $Z^{24}$ is preferably a benzene ring, a pyridine ring, a pyrazine ring, an imidazole ring, a pyrazole ring, or a thiophene ring, more preferably a benzene ring, a pyridine ring, or a pyrazole ring, and even more preferably a benzene ring or a pyridine ring.

One of the preferred modes of the platinum (Pt) complex expressed by General Formula C-2 is a platinum (Pt) complex expressed by General Formula C-4 below:

[Thirty-Fifth Chemical Formula]

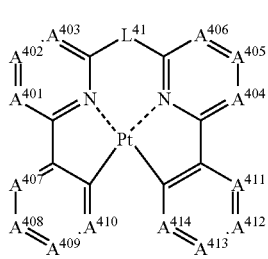

General Formula C-4

(In General Formula C-4, $A^{401}$ to $A^{414}$ represent each independently C—R or a nitrogen atom. R represents a hydrogen atom or a substituent. $L^{41}$ represents a single bond or a divalent linking group.)

General Formula C-4 will now be described.

$A^{401}$ to $A^{414}$ represent each independently C—R or a nitrogen atom. R represents a hydrogen atom or a substituent.

Substituents listed as the aforementioned Substituent Group A can be used as the substituent expressed by R.

$A^{401}$ to $A^{406}$ are preferably C—R, and the R [groups] may be linked to each other to form a ring. If $A^{401}$ to $A^{406}$ are C—R, the R [groups] of $A^{402}$ and $A^{405}$ are preferably a hydrogen atom, an alkyl group, an aryl group, an amino group, an alkoxy group, an aryloxy group, a fluorine atom, or a cyano group, more preferably a hydrogen atom, an amino group, an alkoxy group, an aryloxy group, or a fluorine atom, and especially preferably a hydrogen atom or a fluorine atom. The R [groups] of $A^{401}$, $A^{403}$, $A^{404}$ and $A^{406}$ are preferably a hydrogen atom, an alkyl group, an aryl group, an amino group, an alkoxy group, an aryloxy group, a fluorine atom, or a cyano group, more preferably a hydrogen atom, an amino group, an alkoxy group, an aryloxy group, or a fluorine atom, and especially preferably a hydrogen atom.

$L^{41}$ is defined the same as $L^1$ in General Formula C-1 above, and the preferred ranges are also the same.

For $A^{407}$ to $A^{414}$, the number of nitrogen atoms in $A^{407}$ to $A^{410}$ and in $A^{411}$ to $A^{414}$ is each preferably 0 to 2 and more preferably 0 or 1. When the emission wavelength is shifted to the short wavelength side, either $A^{408}$ or $A^{412}$ is preferably a nitrogen atom, and it is more preferable if $A^{408}$ and $A^{412}$ are both a nitrogen atom.

One of more preferred modes of the platinum (Pt) complex expressed by General Formula C-2 is a platinum (Pt) complex expressed by General Formula C-5 below:

[Thirty-Sixth Chemical Formula]

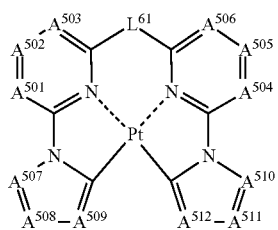

(C-5)

(In General Formula C-5, $A^{501}$ to $A^{512}$ represent each independently C—R or a nitrogen atom. R represents a hydrogen atom or a substituent. $L^{51}$ represents a single bond or a divalent linking group.)

General Formula C-5 will now be described. $A^{501}$ to $A^{506}$ and $L^{51}$ are defined the same as $A^{401}$ to $A^{406}$ and $L^{41}$ in General Formula C-4 above, and the preferred ranges are also the same.

$A^{507}$, $A^{508}$, $A^{509}$, $A^{510}$, $A^{511}$ and $A^{512}$ represent each independently C—R or a nitrogen atom. R represents a hydrogen atom or a substituent. Substituents listed as the aforementioned Substituent Group A can be used as the substituent expressed by R.

Another preferred mode of the platinum (Pt) complex expressed by General Formula C-1 is a platinum (Pt) complex expressed by General Formula C-6 below:

[Thirty-Seventh Chemical Formula]

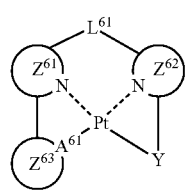

General Formula C-6

(In the formula, $L^{61}$ represents a single bond or a divalent linking group. The $A^{61}$ [groups] represent each independently a carbon atom or a nitrogen atom. $Z^{61}$ and $Z^{62}$ represent each independently a nitrogen-containing aromatic heterocycle. The $Z^{63}$ [groups] represent each independently a benzene ring or an aromatic heterocycle. Y is an anionic acyclic ligand bound to platinum (Pt).)

General Formula C-6 will now be described. $L^{61}$ is defined the same as $L^1$ in General Formula C-1 above, and the preferred ranges are also the same.

$A^{61}$ represents a carbon atom or a nitrogen atom. From the standpoint of the stability of the complex and the standpoint of luminescent quantum yield of the complex, $A^{61}$ is preferably a carbon atom.

$Z^{61}$ and $Z^{62}$ are respectively defined the same as $Z^{21}$ and $Z^{22}$ in General Formula C-2 above, and the preferred ranges are also the same. $Z^{63}$ is defined the same as $Z^{23}$ in General Formula C-2 above, and the preferred ranges are also the same.

Y is an anionic acyclic ligand bound to platinum (Pt). An acyclic ligand is one in which the atom bound to platinum (Pt) does not form a ring in a ligand state. The atom in Y that is bound to platinum (Pt) is preferably a carbon atom, a nitrogen atom, an oxygen atom, or a sulfur atom, more preferably a nitrogen atom or an oxygen atom, and most preferably an oxygen atom.

A vinyl ligand is an example of Y that is bound to platinum (Pt) by a carbon atom. Examples of Y bound to platinum (Pt) by a nitrogen atom include an amino ligand and an imino ligand. Examples of Y bound to platinum (Pt) by an oxygen atom include an alkoxy ligand, an aryloxy ligand, a heteroaryloxy ligand, an acyloxy ligand, a silyloxy ligand, a carboxyl ligand, a phosphate ligand, and a sulfonate ligand. Examples of Y bound to platinum (Pt) by a sulfur atom include an alkylmercapto ligand, an arylmercapto ligand, a heteroarylmercapto ligand, and a thiocarboxylate ligand.

The ligand expressed by Y may have a substituent. Those listed as the aforementioned Substituent Group A can be suitably used as the substituent. In addition, the substituents may also be linked to each other.

The ligand expressed by Y is preferably a ligand bound to platinum (Pt) by an oxygen atom, more preferably an acyloxy ligand, an alkyloxy ligand, an aryloxy ligand, a heteroaryloxy ligand, or a silyloxy ligand, and even more preferably an acyloxy ligand.

One of the more preferred modes of the platinum (Pt) complex expressed by General Formula C-6 is a platinum (Pt) complex expressed by General Formula C-7 below:

[Thirty-Eighth Chemical Formula]

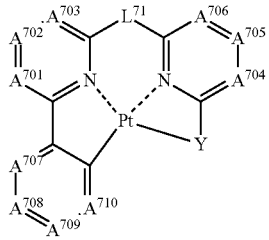

General Formula C-7

(In the formula, $A^{701}$ to $A^{710}$ represent each independently C—R or a nitrogen atom. R represents a hydrogen atom or a substituent. $L^{71}$ represents a single bond or a divalent linking group. Y is an anionic acyclic ligand bound to platinum (Pt).)

General Formula C-7 will now be described. $L^{71}$ is defined the same as $L^{61}$ in General Formula C-6 above, and the preferred ranges are also the same. $A^{701}$ to $A^{710}$ are defined the same as $A^{401}$ to $A^{410}$ in General Formula C-4, and the preferred ranges are also the same. Y is defined the same as Y in General Formula C-6, and the preferred ranges are also the same.

Concrete examples of the platinum (Pt) complex expressed by General Formula C-1 include the compounds described in [0143] to [0152], [0157], [0158], and [0162] to [0168] in Japanese Laid-Open Patent Application 2005-310733, the compounds described in [0065] to [0083] in Japanese Laid-Open Patent Application 2006-256999, the compounds described in [0065] to [0090] in Japanese Laid-Open Patent Application 2006-93542, the compounds described in [0063] to [0071] in Japanese Laid-Open Patent Application 2007-73891, the compounds described in [0079] to [0083] in Japanese Laid-Open Patent Application 2007-324309, the compounds described in [0065] to [0090] in Japanese Laid-Open Patent Application 2006-93542, the compounds described in [0055] to [0071] in Japanese Laid-Open Patent Application 2007-96255, and [the compounds described in] [0043] to [0046] in Japanese Laid-Open Patent Application 2006-313796. Other examples include the platinum (Pt) complexes listed below:

[Thirty-Ninth Chemical Formula]

1-1

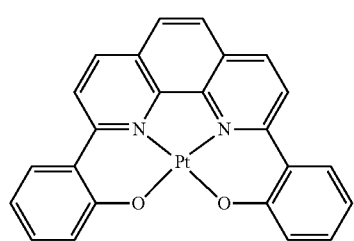

1-2

1-3

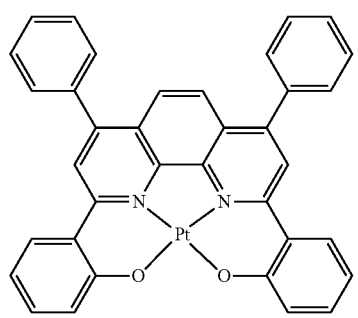

2-0

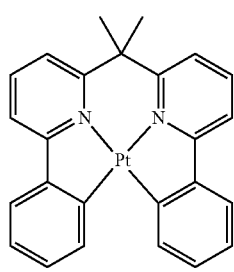

2-1

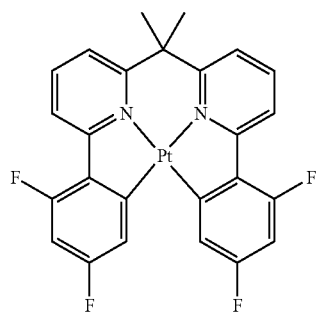

2-2

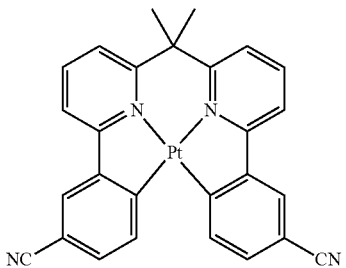

2-3

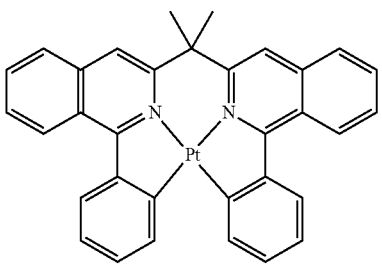

2-4

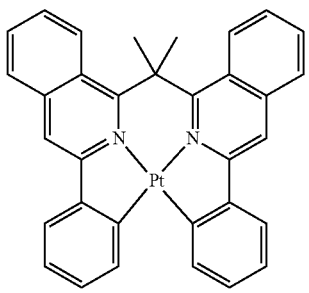

2-5

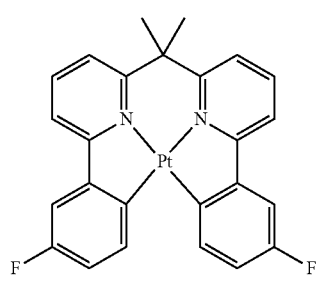

-continued
2-6
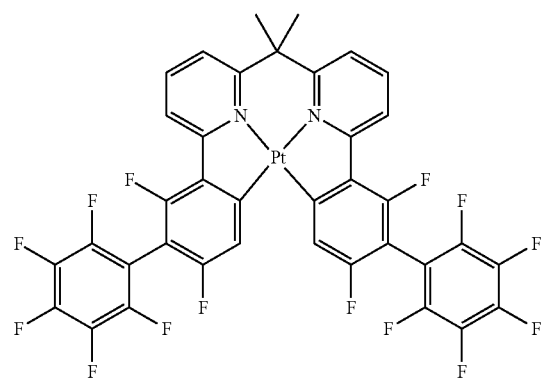
2-7
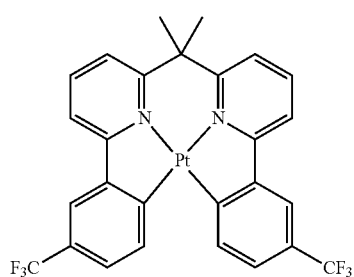
2-8
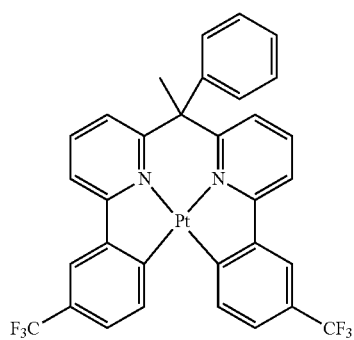
2-9
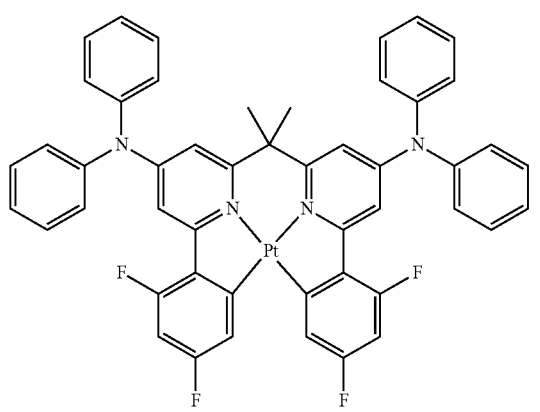
-continued
2-10
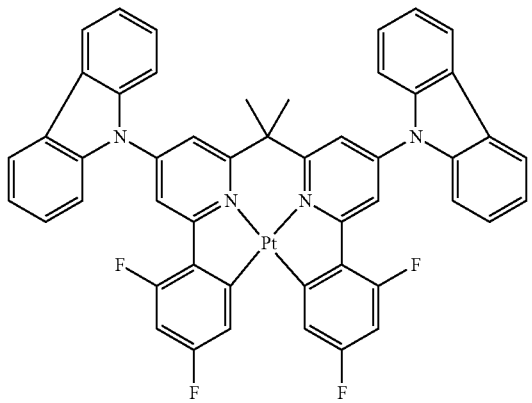
2-11
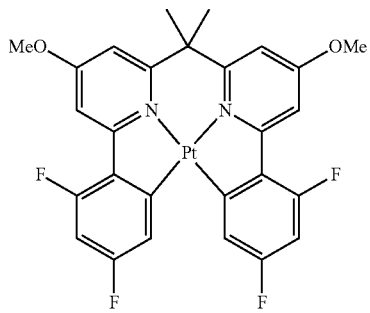
2-12
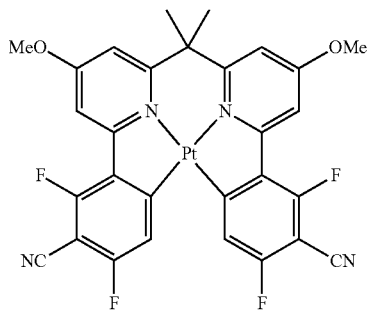
3-1
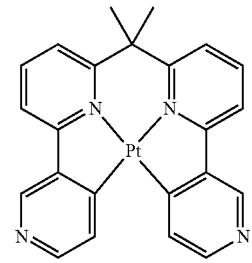
3-2
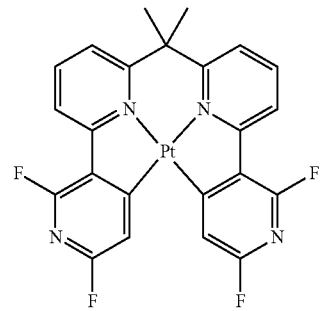

-continued
3-3
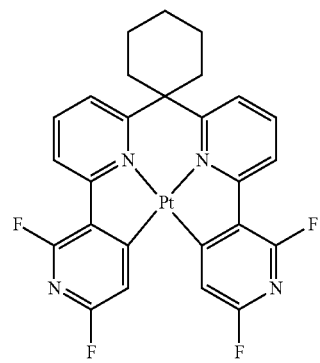
3-4
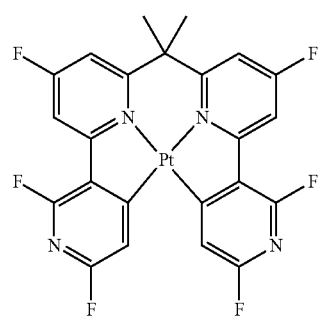
3-5
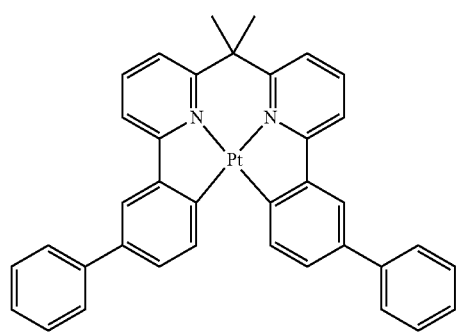
[Fortieth Chemical Formula]
4-1
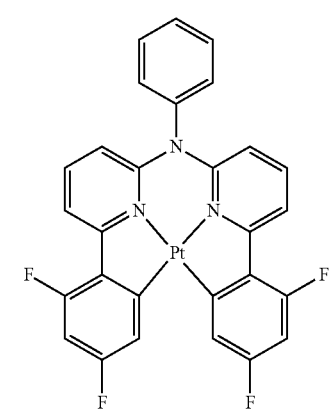
-continued
4-2
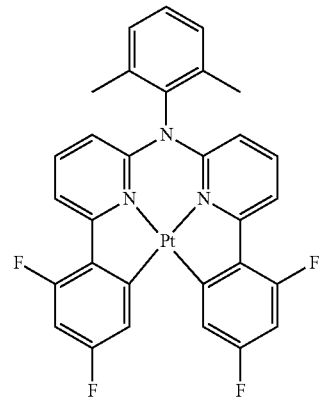
4-3
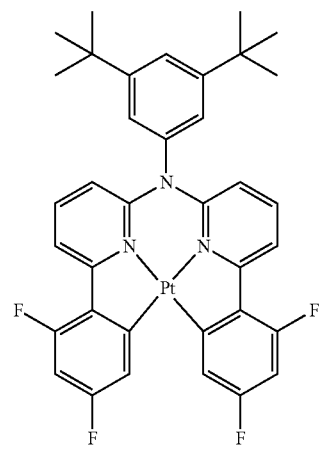
4-4
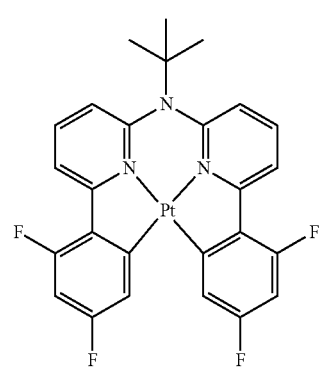
4-5
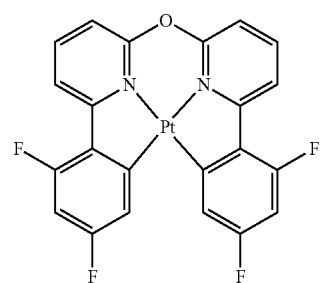

5-1
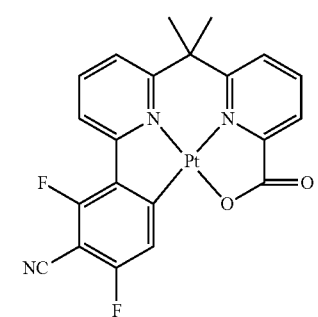
5-2
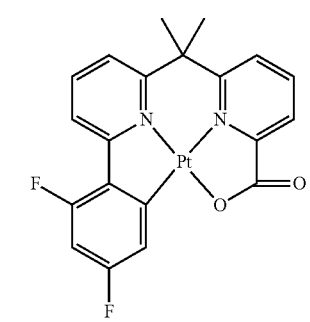
5-3
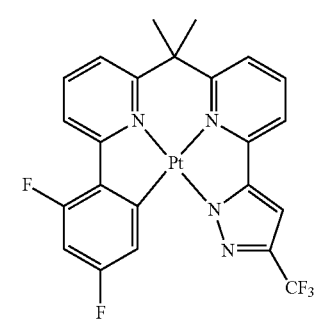
5-5
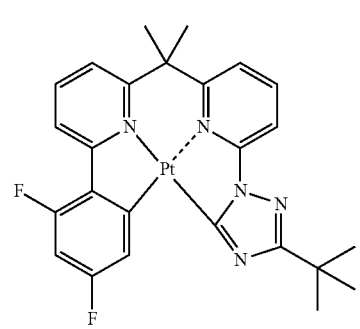
6-1
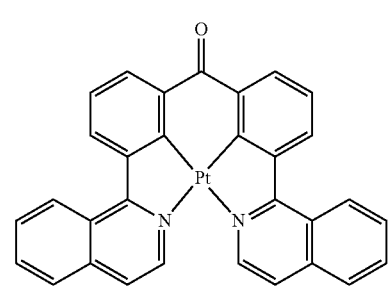
6-2
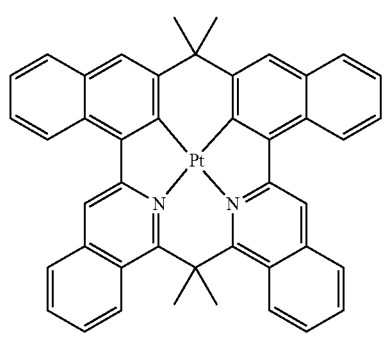
6-3
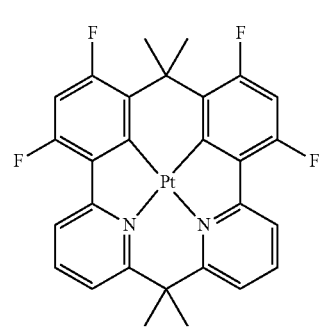
6-4
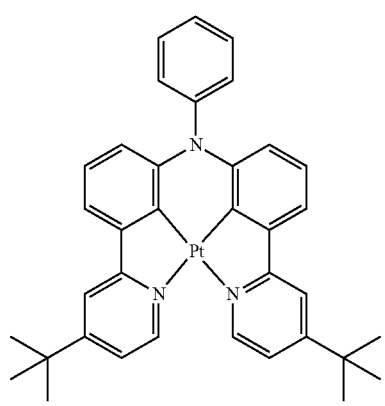
6-5
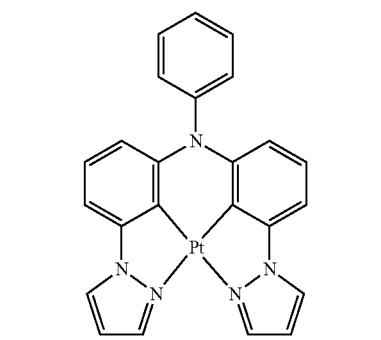

-continued
7-1
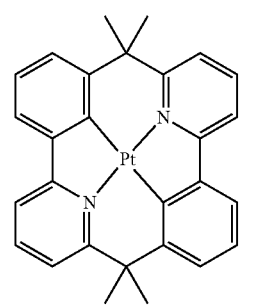
7-2
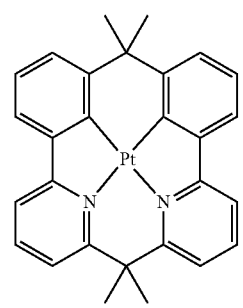
7-3
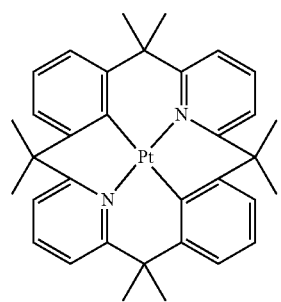
7-4
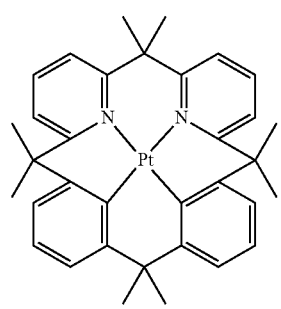
7-5
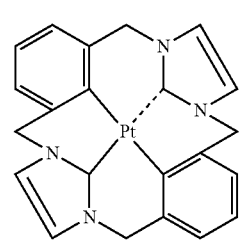
-continued
8-1
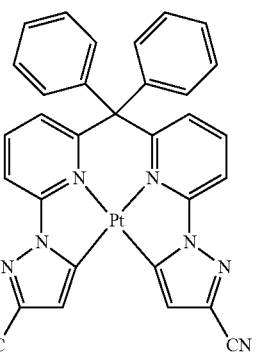
8-2
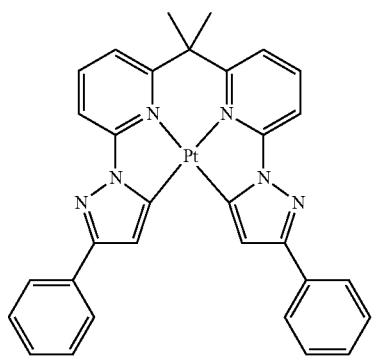
8-3
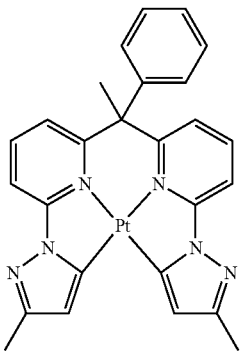
8-4
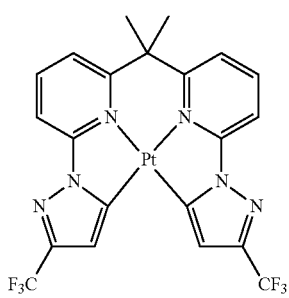

-continued
8-5
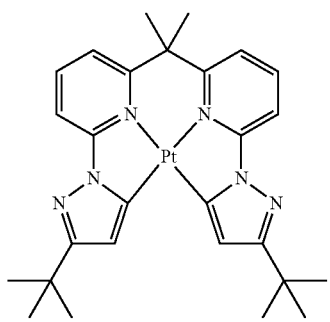
[Forty-First Chemical Formula]
8-6
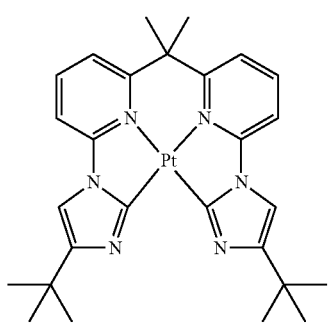
8-8
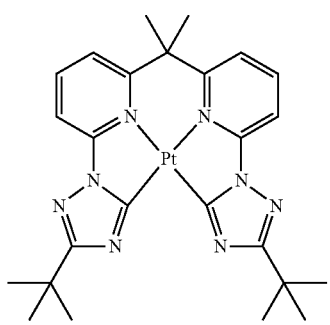
8-9
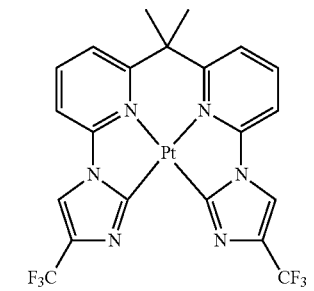
8-10
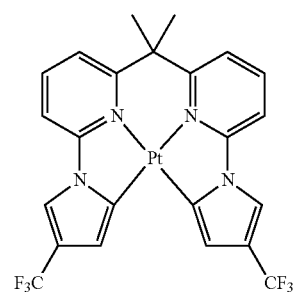
-continued
8-11
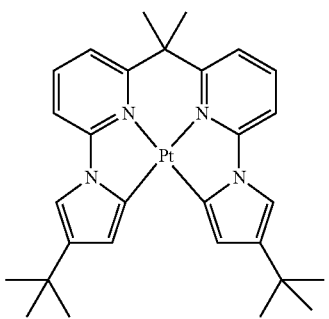
9-1
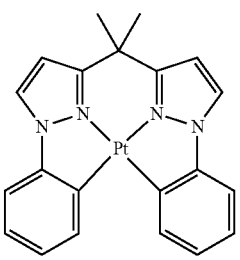
9-2
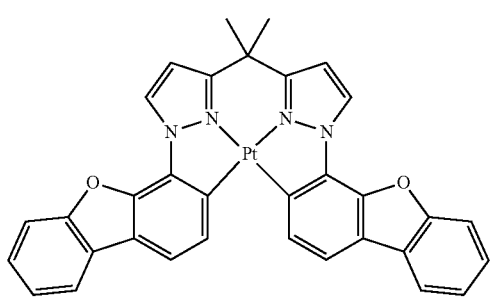
9-3
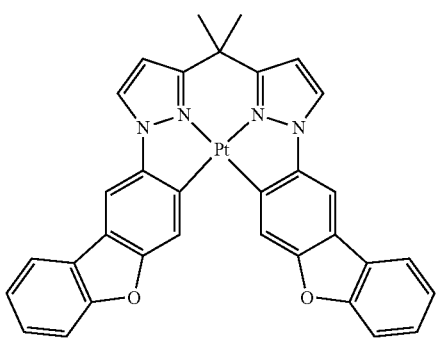
9-4
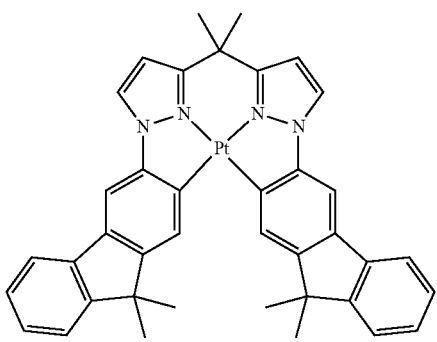

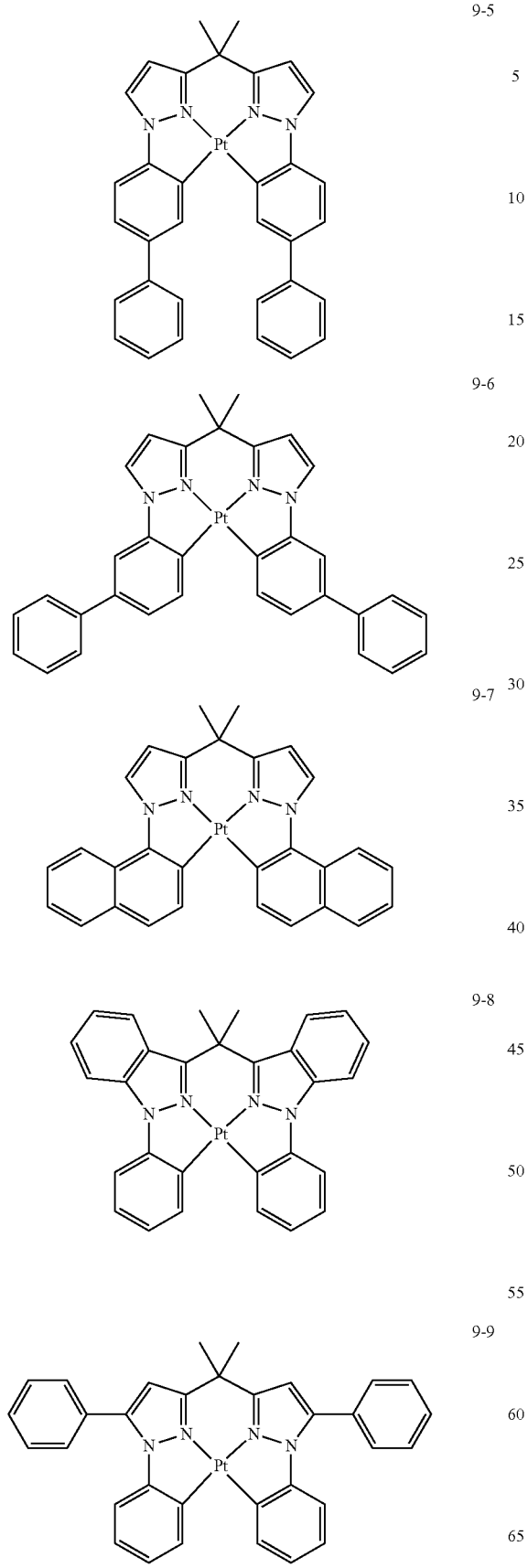
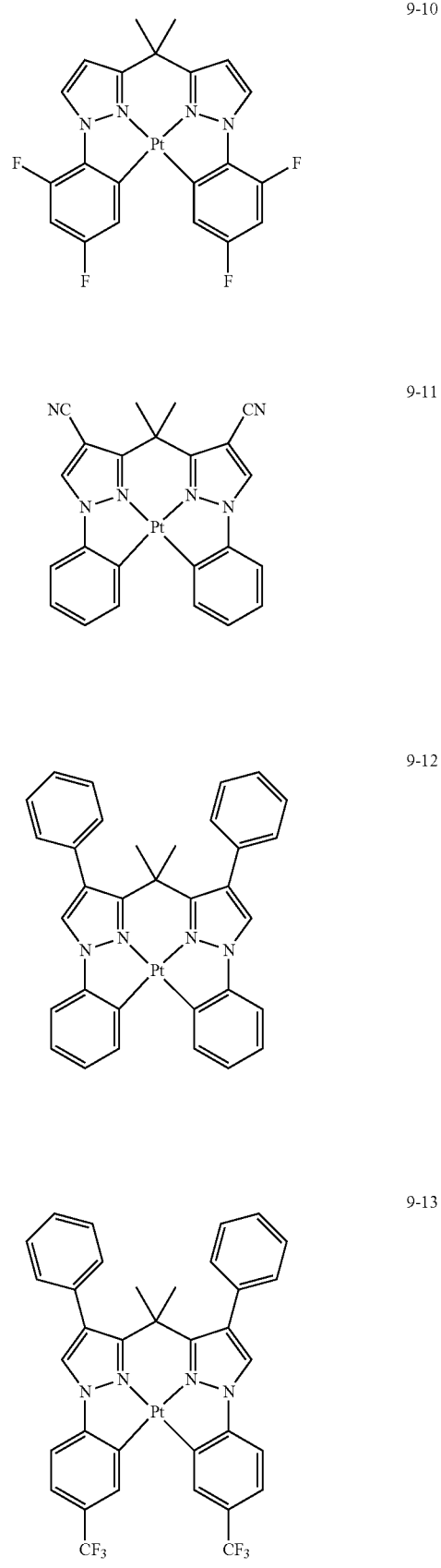

9-14

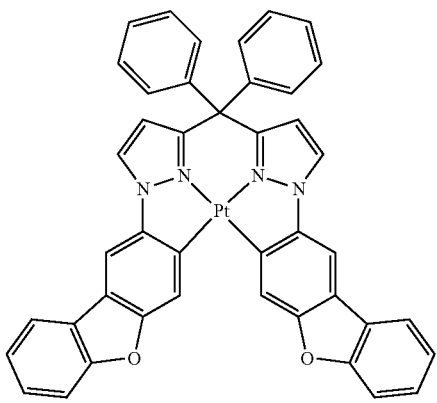

9-15

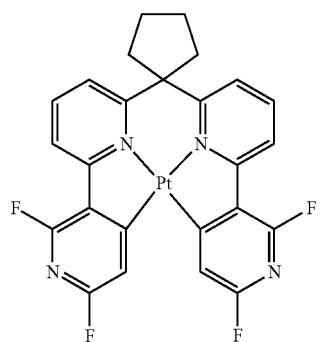

9-16

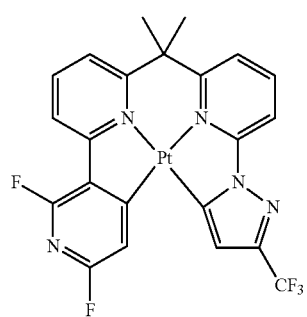

9-17

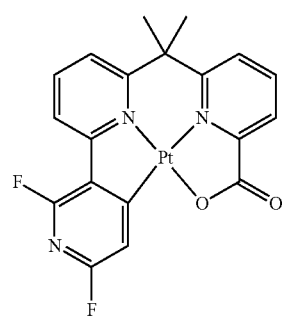

9-18

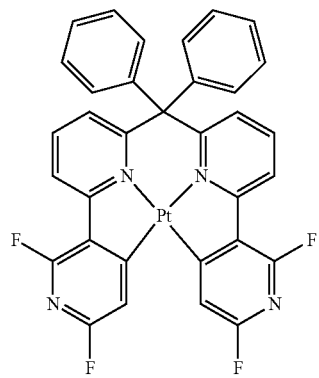

9-19

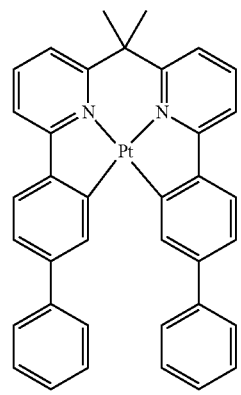

The platinum (Pt) complex compound expressed by General Formula C-1 can be synthesized by various methods such as the method described in line 53 of the left-hand column to line 7 of the right-hand column on page 789, the method described in lines 18 to 38 of the left-hand column on page 790, or the method described in lines 19 to 30 of the right-hand column on page 790, in *Journal of Organic Chemistry* 53, 786, (1988), G. R. Newkome et al., or by a combination of these [methods], as well as by the method described in lines 26 to 35 of page 2752 in *Chemische Berichte* [*Chemical Reports*] 113, 2749 (1980), H. Lexy et al.

For example, [the platinum complex compound] can be obtained by treating a ligand or a dissociate thereof and a metal compound in the presence or absence of a solvent (such as a halogen-based solvent, an alcohol-based solvent, an ether-based solvent, an ester-based solvent, a ketone-based solvent, a nitrile-based solvent, an amide-based solvent, a sulfone-based solvent, a sulfoxide-based solvent, or water) and in the presence or absence of a base (various inorganic or organic bases such as sodium methoxide, t-butoxy potassium, triethylamine, and potassium carbonate) at room temperature or below or under heating (in addition to normal heating, a method involving heating by microwaves is also effective).

The amount in which the compound expressed by General Formula C-1 is contained in the aforementioned light-emitting layer of the organic electroluminescent element of the present invention is preferably 1 to 30 wt %, more preferably 3 to 25 wt %, and even more preferably 5 to 20 wt % in the light-emitting layer.

There are no particular restrictions on the type of fluorescent material, but examples include benzoxazole, benzimidazole, benzothiazole, styryl benzene, polyphenyl, diphenyl butadiene, tetraphenyl butadiene, naphthalimide, coumarin, pyran, perinone, oxadiazole, aldazine, pyralizine, cyclopentadiene, bis-styryl anthracene, quinacridone, pyrrolopyridine, thiadiazolopyridine, cyclopentadiene, styrylamine, condensed polycyclic aromatic compounds (such as anthracene, phenanthrene, pyrene, perylene, fluoranthene, rubrene, chrysene, and pentacene), a variety of metal complexes typified by metal complexes of 8-quinolinol, pyromethene complexes, and rare earth complexes, polymer compounds such as polythiophene, polyphenylene, and polyphenylene vinylene, organosilanes, and derivatives of these.

Concrete examples of the fluorescent material will be shown below, but the present invention is in no way limited to or by these:

[Forty-Second Chemical Formula]

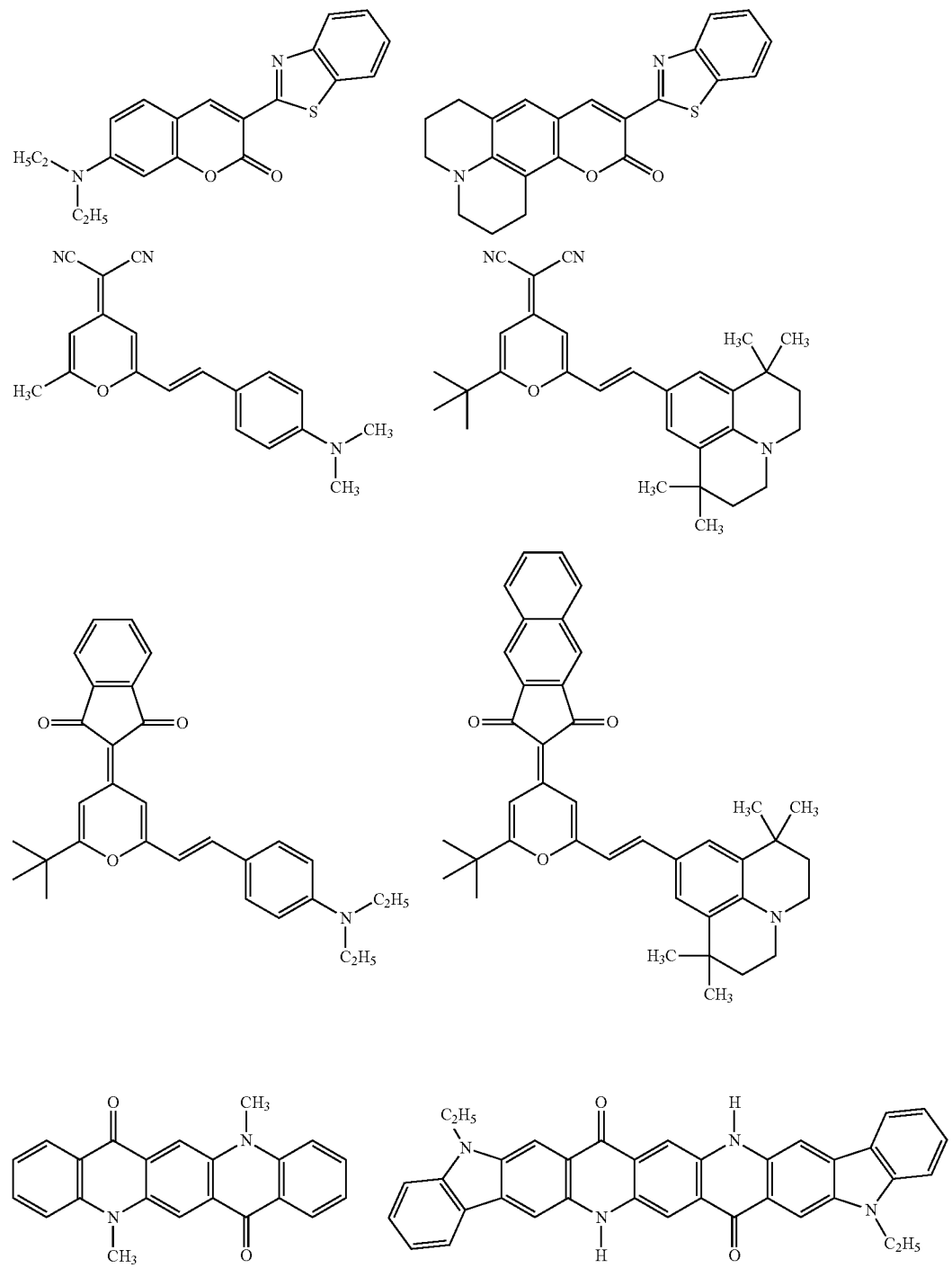

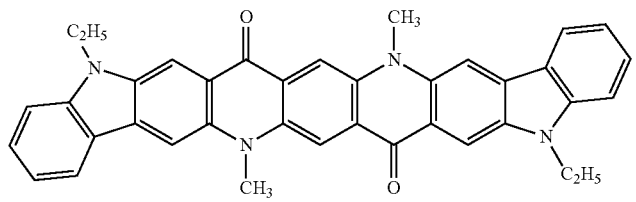
[Forty-Third Chemical Formula]
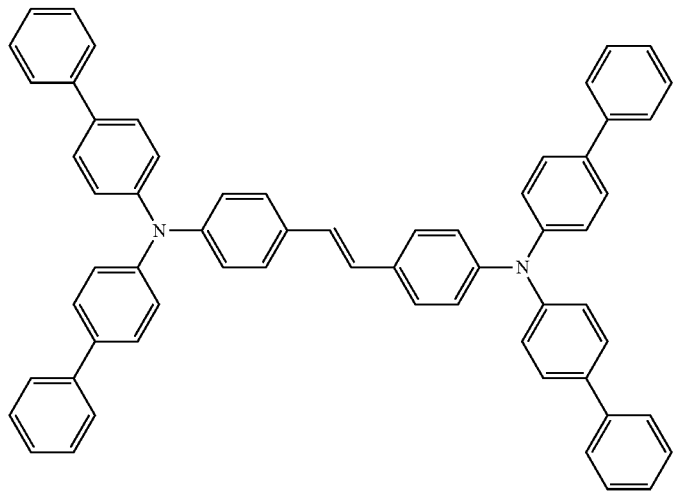
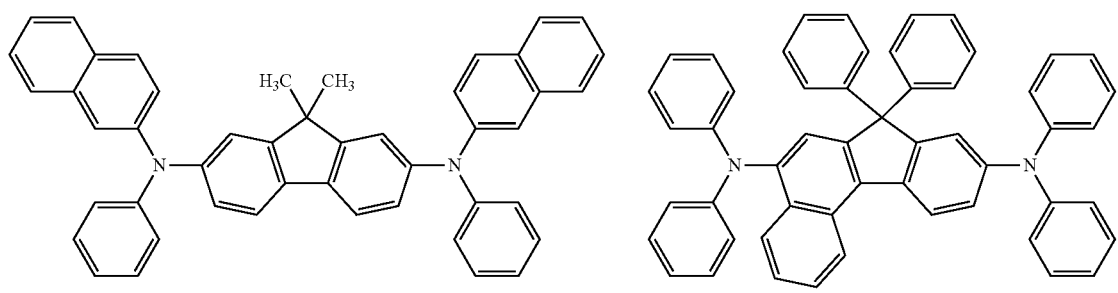
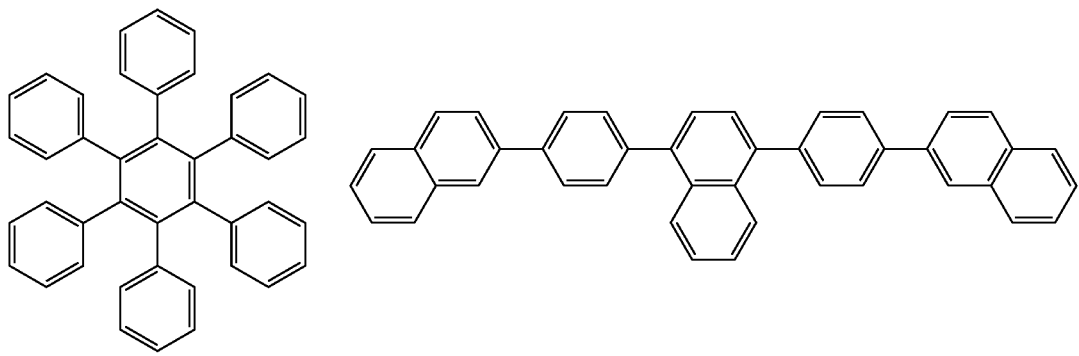

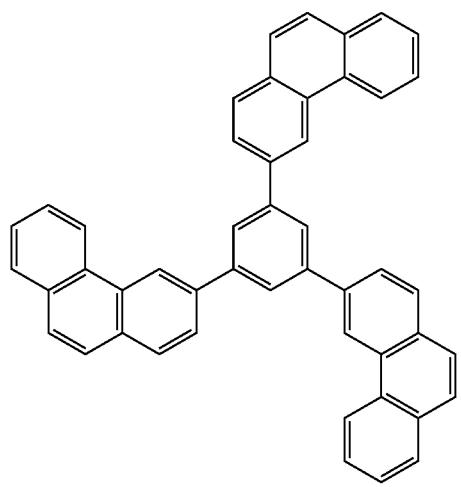
[Forty-Fourth Chemical Formula]
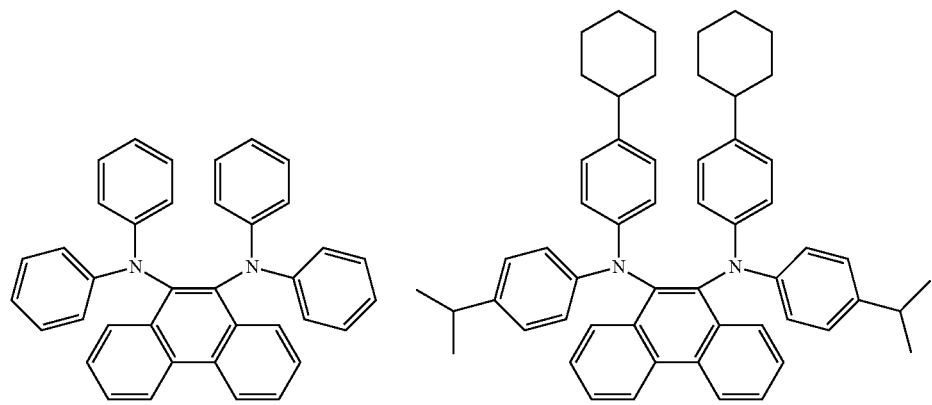
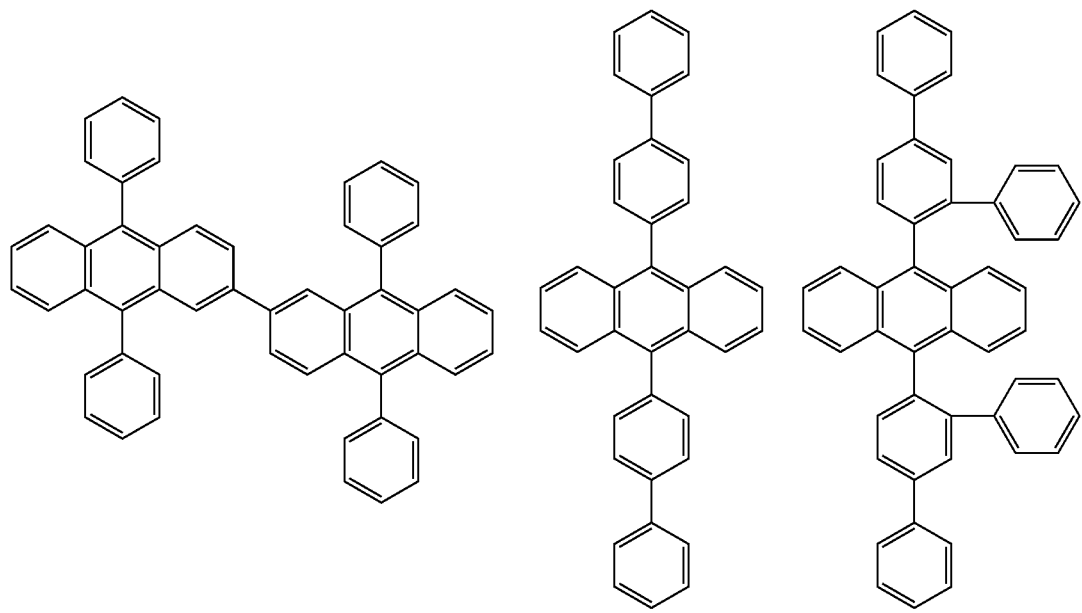

-continued
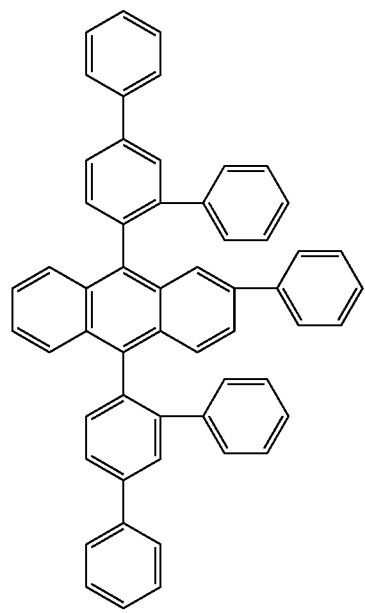
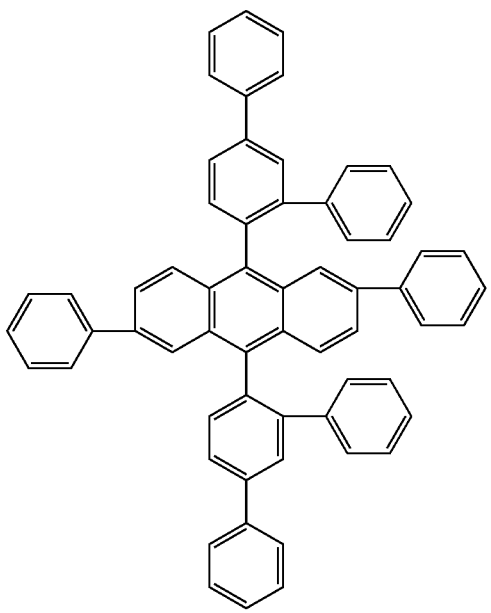
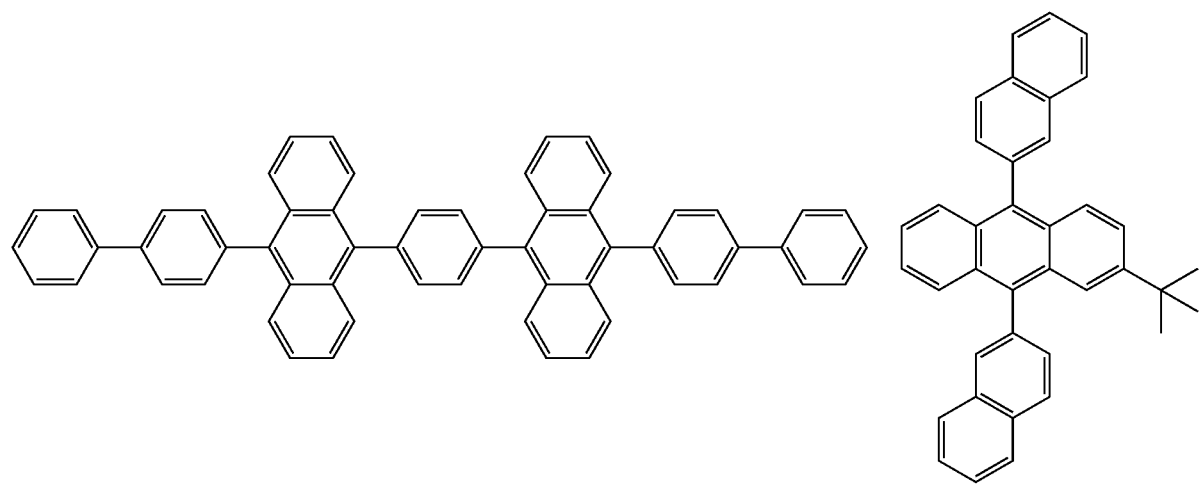

[Forty-Fifth Chemical Formula]
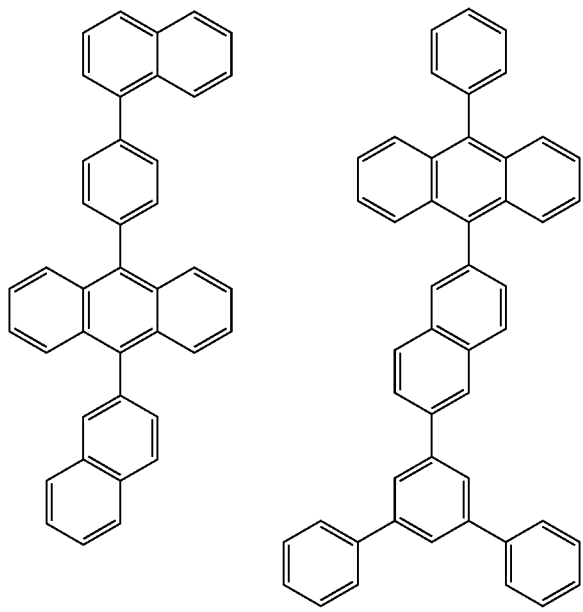
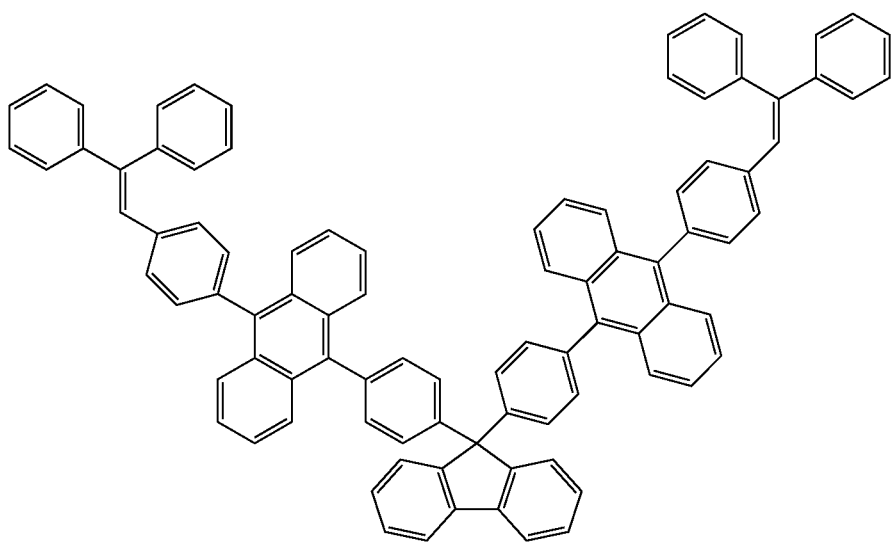

-continued
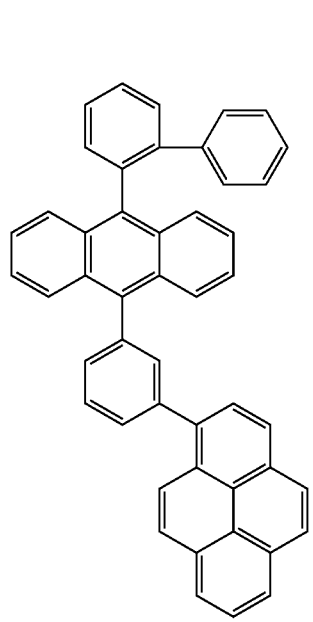
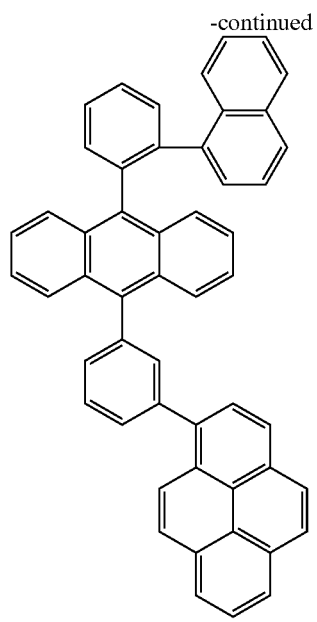
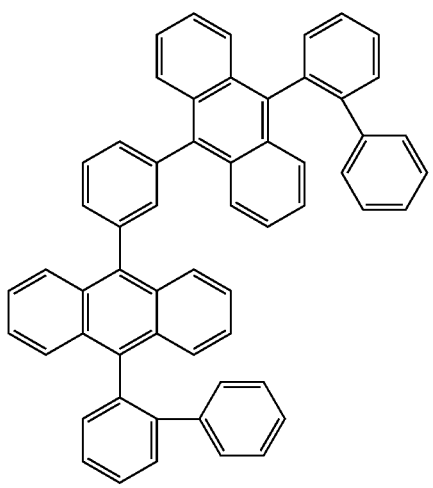
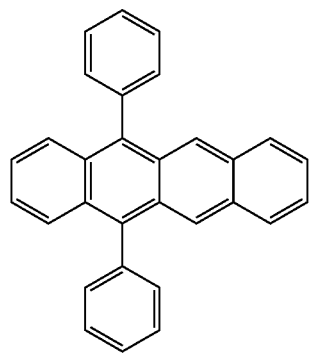
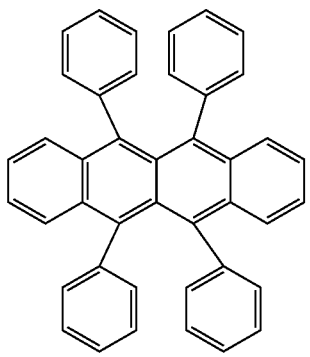
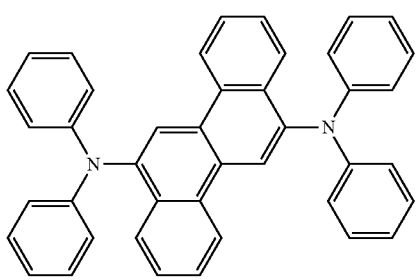
[Forty-Sixth Chemical Formula]
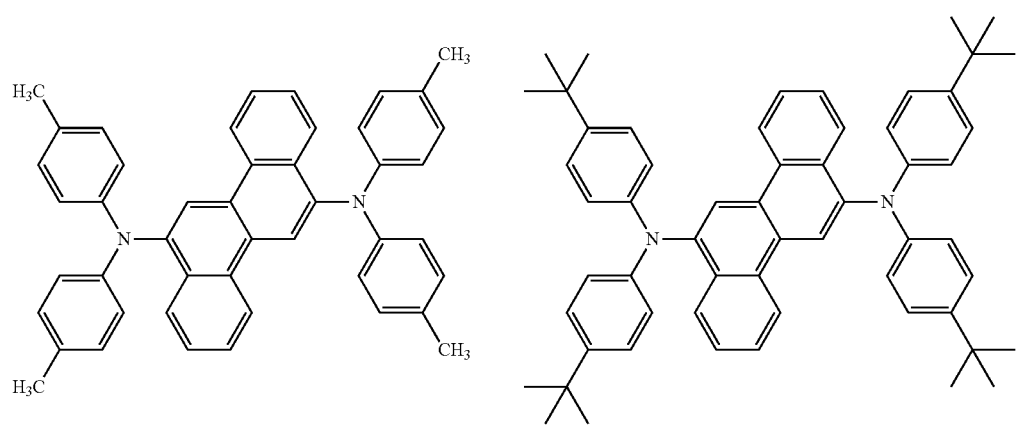

-continued
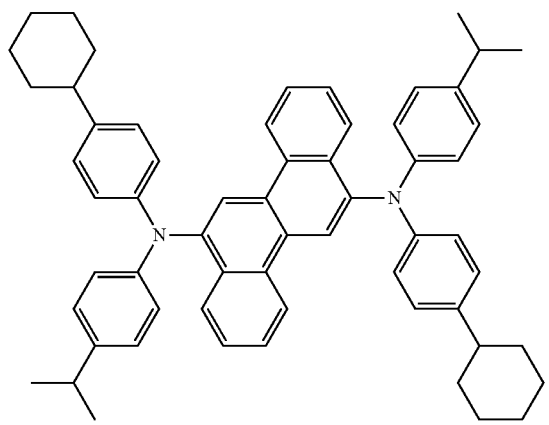
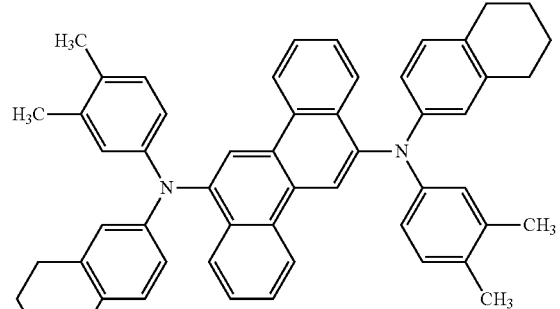
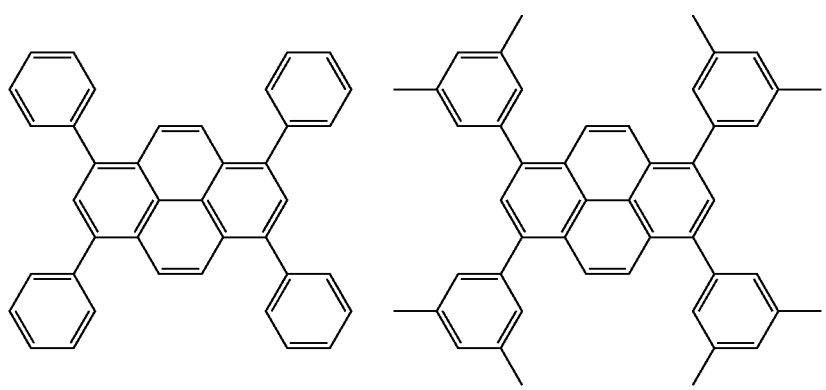
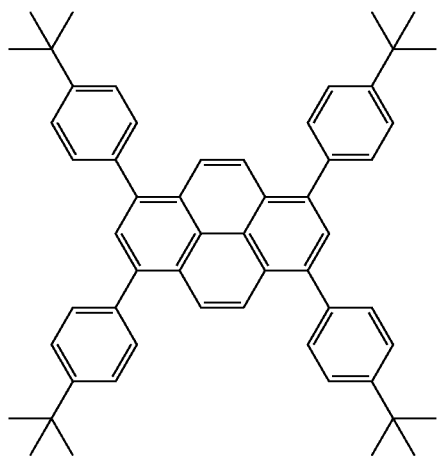
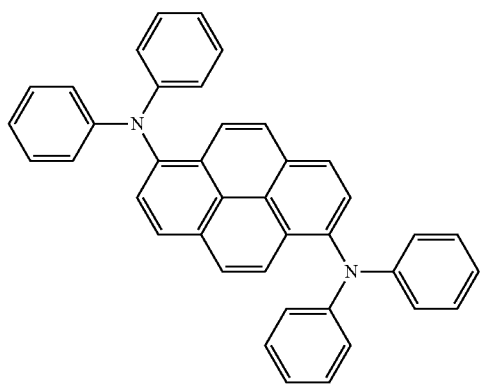
[Forty-Seventh Chemical Formula]
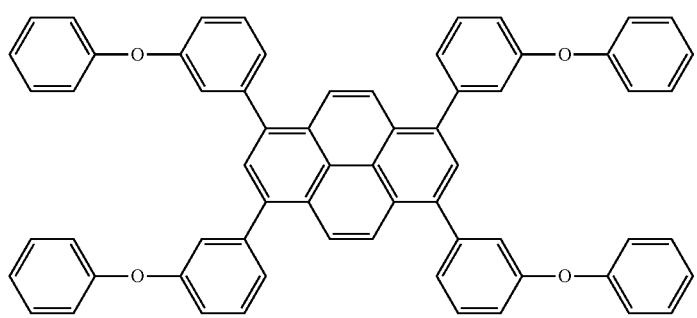

101
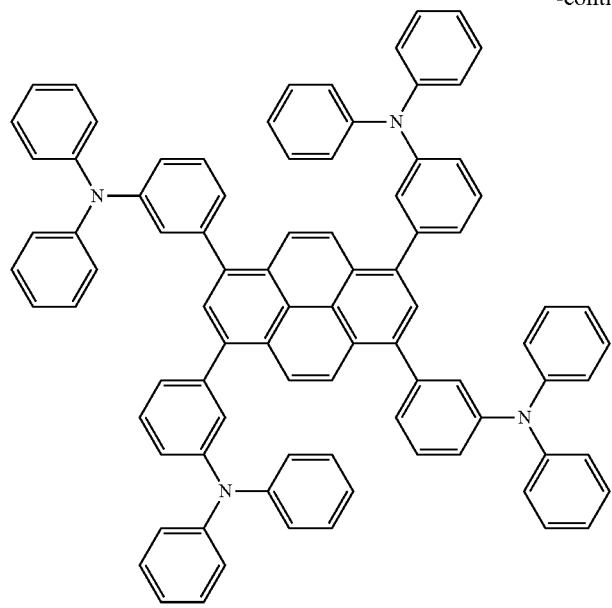
102
-continued
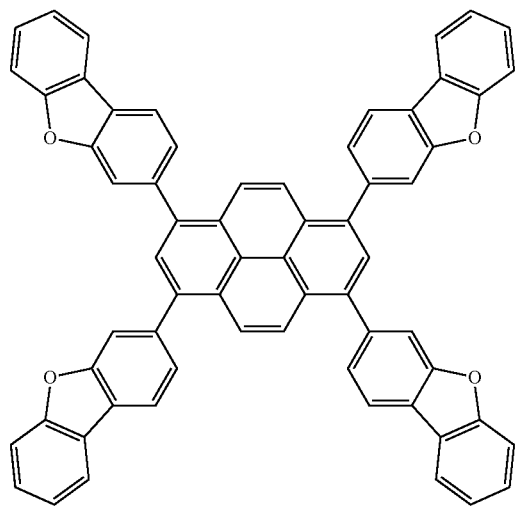
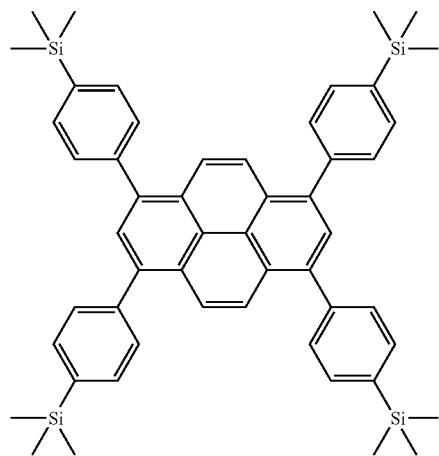
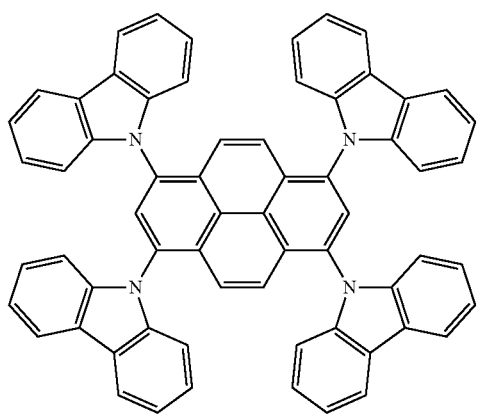
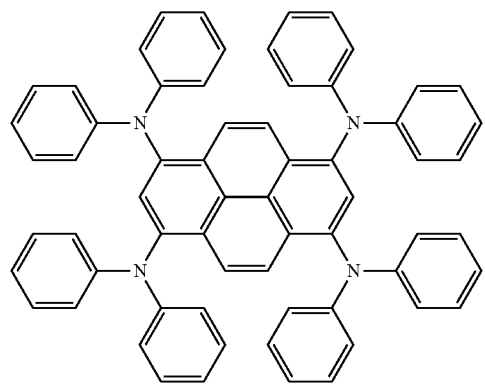

[Forty-Eighth Chemical Formula]
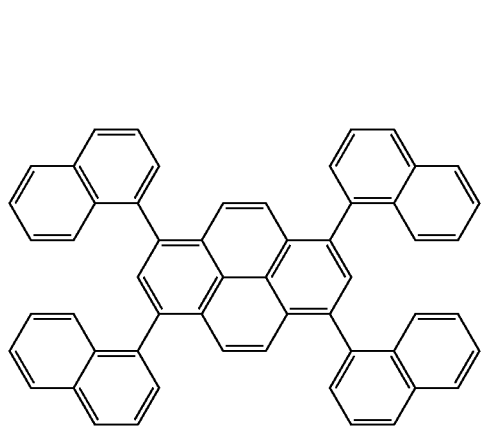

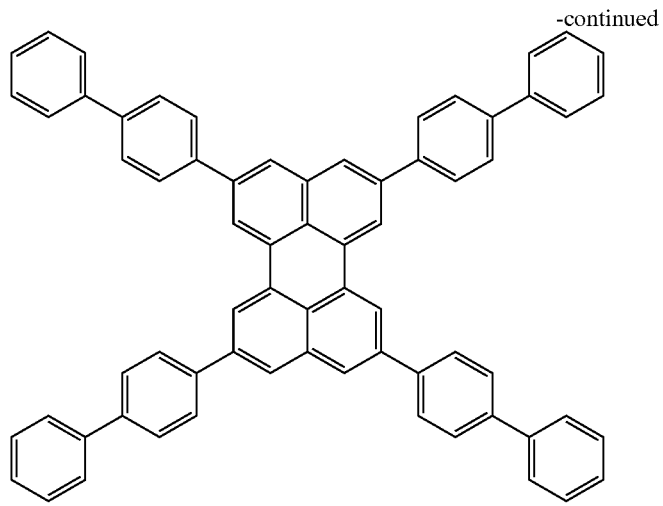

The amount of fluorescent material contained in the aforementioned light-emitting layer of the organic electroluminescent element of the present invention is preferably 1 to 30 wt %, more preferably 1 to 20 wt %, and even more preferably 1 to 10 wt % in the light-emitting layer.

In the present invention, in terms of preventing quenching with the compound expressed by General Formula 1, it is preferable for the maximum emission wavelength of the light-emitting material to be from 400 to 700 nm, more preferably from 500 to 700 nm, even more preferably from 520 to 650 nm, and most preferably from 520 to 550 nm.

The maximum emission wavelength of the phosphorescent material expressed by General Formula E-3 is in a range from about 500 to 550 nm when a plurality of $R^{T1}$ to $R^{T7}$ [groups] and R' do not form a ring together, and the maximum emission wavelength of the phosphorescent material expressed by General Formula E-4 or E-5 is in a range from about 550 to 650 nm.

There are no particular restrictions on the thickness of the light-emitting layer, but 2 to 500 nm is usually preferable, and from the standpoint of external quantum efficiency, [a thickness of] 5 to 200 nm is more preferable, and 10 to 100 nm is even more preferable.

The light-emitting layer in the organic electroluminescent element of the present invention may be constituted from only a light-emitting material or may be made up of a mixed layer of a host material and a light-emitting material. The type of the light-emitting material may be just one type or two or more types. The host material is preferably a charge transport material. There may be just one kind of host material, or two or more kinds may be used. Examples include a mixture of an electron transporting host material and a hole transporting host material. Furthermore, a material which does not have a charge transporting property and does not emit light may be included in the light-emitting layer.

Moreover, the light-emitting layer may be a single layer or a multilayer of two or more layers, and the same light-emitting material or host material may be contained in each layer, or a different material may be contained in each layer. When there are a plurality of light-emitting layers, each of the light-emitting layers may also emit light of a different color.

(Host Material)

The host material is a compound that mainly handles the injection and transport of charges in the light-emitting layer, and is also a compound that substantially does not emit light itself [The phrase] "substantially does not emit light" here means that the amount of light emitted from this compound that substantially does not emit light is preferably no more than 5% of the total amount of light emitted by the entire element, more preferably no more than 3%, and even more preferably no more than 1%.

The compound expressed by General Formula 1 can be used as the host material.

The following compounds are examples of other host materials that can be used in the organic electroluminescent element of the present invention:

These examples include pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin compounds, condensed ring aromatic hydrocarbon compounds (such as anthracene, pyrene, fluorene, naphthalene, phenanthrene, and triphenylene), polysilane compounds, poly(N-vinylcarbazole), aniline copolymers, conductive macromolecular oligomers such as thiophene oligomers and polythiophene, organosilanes, carbon films, pyridine, pyrimidine, triazine, imidazole, pyrazole, triazole, oxazole, oxadiazole [sic][5], fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic acid anhydrides such as naphthalene [and] perylene, phthalocyanine, and a variety of metal complexes typified by metal complexes of an 8-quinolinol derivative, metal phthalocyanine, and metal complexes having benzoxazole or benzothiazole as a ligand, and derivatives of these (which may have a substituent or a condensed ring).

[5] Translator's note: "imidazole," "pyrazole," "triazole," "oxazole," and "oxadiazole" are repeated in the original in this list.

Of these, carbazole, dibenzothiophene, dibenzofuran, arylamine, condensed ring aromatic hydrocarbon compounds, and metal complexes are especially preferable.

The host material that can be used together in the light-emitting layer of the organic electroluminescent element of the present invention may be a hole transporting host material or an electron transporting host material.

In the light-emitting layer, from the standpoints of color purity, luminous efficiency, and drive durability, it is preferable for the lowest excited triplet energy ($T_1$ energy) of the aforementioned host material in a film state to be higher than the $T_1$ energy of the aforementioned phosphorescent material. The $T_1$ of the host material is preferably higher than the $T_1$ of the phosphorescent material by at least 0.1 eV, more preferably higher by at least 0.2 eV, and even more preferably higher by at least 0.3 eV.

If the $T_1$ of the host material in a film state is lower than the $T_1$ of the phosphorescent material, emission of light is quenched, so the host material needs to have a higher $T_1$ than the phosphorescent material. Moreover, even when the $T_1$ of the host material is higher than that of the phosphorescent material, if the difference in the $T_1$ [values] between the two is small, reverse energy movement from the phosphorescent material to the host material will occur in places, and this can lead to lower efficiency or a decrease in durability. Accordingly, the host material needs to have a sufficiently high $T_1$ as well as good chemical stability and carrier injection and transport properties.

In addition, there are no particular restrictions on the amount in which the host compound is contained in the light-emitting layer of the organic electroluminescent element of the present invention, but from the standpoints of luminous efficiency and drive voltage, it is preferably at least 15 wt % and no more than 95 wt % with respect to the weight of all the compounds forming the light-emitting layer. If the light-emitting layer includes a plurality of kinds of host compound including a compound expressed by General Formula 1, then the compound expressed by General Formula 1 is preferably contained in the total host compound in an amount of at least 50 wt % and no more than 99 wt %.

(Other Layers)

The organic electroluminescent element of the present invention may have other layers besides the aforementioned light-emitting layer.

Examples of other organic layers other than the aforementioned light-emitting layer that may be included in the aforementioned organic layers include a hole injection layer, a hole transport layer, a blocking layer (hole blocking layer, exciton blocking layer, etc.), and an electron transport layer. The following are concrete examples of the layer configuration, but the present invention is in no way limited to these configurations:

anode/hole transport layer/light-emitting layer/electron transport layer/cathode anode/hole transport layer/light-emitting layer/blocking layer/electron transport layer/cathode anode/hole transport layer/light-emitting layer/blocking layer/electron transport layer/electron injection layer/cathode anode/hole injection layer/hole transport layer/light-emitting layer/blocking layer/electron transport layer/cathode anode/hole injection layer/hole transport layer/light-emitting layer/electron transport layer/electron injection layer/cathode anode/hole injection layer/hole transport layer/light-emitting layer/blocking layer/electron transport layer/electron injection layer/cathode anode/hole injection layer/hole transport layer/blocking layer/light-emitting layer/blocking layer/electron transport layer/electron injection layer/cathode The organic electroluminescent element of the present invention preferably includes at least one organic layer preferably disposed between the aforementioned anode and the aforementioned light-emitting layer (A). From the anode side, a hole injection layer, a hole transport layer, and an electron blocking layer can be cited as examples of organic layers preferably disposed between the aforementioned anode and the aforementioned light-emitting layer of (A) above.

The organic electroluminescent element of the present invention preferably includes at least one organic layer preferably disposed between the aforementioned cathode and the aforementioned light-emitting layer (B). From the cathode side, an electron injection layer, an electron transport layer, and a hole blocking layer can be cited as examples of organic layers preferably disposed between the aforementioned cathode and the aforementioned light-emitting layer of (B) above.

In concrete terms, one example of a preferred mode of the organic electroluminescent element of the present invention is the mode described in FIG. 1, being a mode in which a hole injection layer 4, a hole transport layer 5, a light-emitting layer 6, a hole blocking layer 7, and an electron transport layer 8 are laminated in this order from the side of the anode 3 as the aforementioned organic layers.

These layers other than the light-emitting layer that may be included in the organic electroluminescent element of the present invention will be described below.

(A) Organic Layers Preferably Disposed between the Anode and the Aforementioned Light-Emitting Layer First, (A) organic layers preferably disposed between the aforementioned anode and the aforementioned light-emitting layer will be described.

(A-1) Hole Injection Layer and Hole Transport Layer

The hole injection layer and the hole transport layer are layers having the function of accepting holes from the anode or the anode side and transporting them to the cathode side.

Regarding the hole injection layer and the hole transport layer, what is stated in paragraph numbers [0165] to [0167] in Japanese Laid-Open Patent Application 2008-270736 can be applied to the present invention.

The hole injection layer preferably contains an electron-accepting dopant. The effects of having the hole injection layer contain an electron-accepting dopant are that hole injection is enhanced, drive voltage decreases, efficiency is higher, and so forth. The electron-accepting dopant may be either an organic material or inorganic material as long as it is a material capable of pulling electrons from the doped material and generating radical cations, but examples include tetracyanoquinodimethane (TCNQ), tetrafluorotetracyanoquinodimethane ($F_4$-TCNQ), and molybdenum oxide.

The electron-accepting dopant in the hole injection layer is preferably contained in an amount of 0.01 to 50 wt %, more preferably 0.1 to 40 wt %, and even more preferably 0.2 to 30 wt %, with respect to the weight of all the compounds forming the hole injection layer.

(A-2) Electron Blocking Layer

The electron blocking layer is a layer having the function of preventing the electrons transported from the cathode side to the light-emitting layer from escaping to the anode side. In the present invention, an electron blocking layer can be provided as an organic layer that is adjacent to the light-emitting layer on the anode side.

As examples of organic compounds that constitute an electron blocking layer, those listed above as examples of hole transport materials can be used.

The thickness of the electron blocking layer is preferably 1 to 500 nm, more preferably 3 to 100 nm, and even more preferably 5 to 50 nm.

The electron blocking layer may have a single-layer structure composed of one or more types of the aforementioned materials, or may have a multilayer structure composed of a plurality of layers of the same composition or different compositions.

From the standpoints of color purity, luminous efficiency, and drive durability, the material used in the electron blocking layer preferably has [a $T_1$ energy] higher than the $T_1$ energy of the aforementioned phosphorescent material. The $T_1$ in a film state of the material used in the electron blocking layer is preferably at least 0.1 eV higher than the $T_1$ of the phosphorescent material, more preferably at least 0.2 eV higher, and even more preferably at least 0.3 eV higher.

(B) Organic Layers Preferably Disposed between the Cathode and the Aforementioned Light-Emitting Layer Next, (B) organic layers preferably disposed between the cathode and the aforementioned light-emitting layer will be described.

(B-1) Electron Injection Layer and Electron Transport Layer

The electron injection layer and the electron transport layer are layers having the function of accepting electrons from the cathode or the cathode side and transporting them to the anode side. The electron injection material and electron transport material used for these layers may be compounds with either a low or a high molecular weight.

The compounds expressed by General Formula 1 above can be used as electron transport materials. Other electron transport materials are preferably selected from among a pyridine derivative, a quinoline derivative, a pyrimidine derivative, a pyrazine derivative, a phthalazine derivative, a phenanthroline derivative, a triazine derivative, a triazole derivative, an oxazole derivative, an oxadiazole derivative, an imidazole derivative, a benzimidazole derivative, an imidazopyridine derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic tetracarboxylic acid anhydride such as naphthalene and perylene, a phthalocyanine derivative, various metal complexes typified by metal complexes of an 8-quinolinol derivative, metal phthalocyanine, and metal complexes having benzoxazole or benzothiazole as a ligand, an organic silane derivative typified by silole, and condensed ring hydrocarbon compounds (such as naphthalene, anthracene, phenanthrene, triphenylene, and pyrene), and the like, with a pyridine derivative, a benzimidazole derivative, an imidazopyridine derivative, a metal complex, or a condensed ring hydrocarbon compound being more preferable.

From the standpoint of lowering the drive voltage, the thickness of the electron injection layer and electron transport layer is preferably no more than 500 nm for each.

The thickness of the electron transport layer is preferably 1 to 500 nm, more preferably 5 to 200 nm, and even more preferably 10 to 100 nm. In addition, the thickness of the electron injection layer is preferably 0.1 to 200 nm, more preferably 0.2 to 100 nm, and even more preferably 0.5 to 50 nm.

The electron injection layer and the electron transport layer may have a single-layer structure composed of one or more types of the aforementioned materials, or a multilayer structure composed of a plurality of layers of the same composition or different compositions.

The electron injection layer preferably contains an electron-donating dopant. The effects of having the electron injection layer contain an electron-donating dopant are that electron injection is enhanced, drive voltage decreases, efficiency is higher, and so forth. The electron-donating dopant may be either an organic material or inorganic material as long as it is a material capable of giving electrons to the doped material and generating radical anions, but examples include tetrathiafulvalene (TTF), tetrathianaphthacene (TTT) [sic][6], bis-[1,3-diethyl-2-methyl-1,2-dihydrobenzimidazolyl] and other such dihydroimidazole compounds, lithium, and cesium.

[6] Translator's note: The abbreviation of "tetrathianaphthacene" should be "TTN," and "TTT" is "tetrathiatetracene," so this abbreviation "TTT" here seems to be an error in the original for "TTN."

The electron-donating dopant in the electron injection layer is preferably contained in an amount of 0.01 to 50 wt %, more preferably 0.1 to 40 wt %, and [even] more preferably 0.5 to 30 wt %, with respect to the weight of all the compounds forming the electron injection layer.

(B-2) Hole Blocking Layer

The hole blocking layer is a layer having the function of preventing the holes transported from the anode side to the light-emitting layer from escaping to the cathode side. In the present invention, a hole blocking layer can be provided as an organic layer that is adjacent to the light-emitting layer on the cathode side.

The $T_1$ energy in a film state of the organic compound constituting the hole blocking layer is preferably higher than the $T_1$ energy of the light-emitting material for the purpose of preventing energy movement of excitons generated in the light-emitting layer, thus preventing a decrease in luminous efficiency.

The compounds expressed by General Formula 1 above can be used as examples of organic compounds that constitute a hole blocking layer.

Examples of other organic compounds that constitute a hole blocking layer other than the compounds expressed by General Formula 1 above include aluminum(III) bis(2-methyl-8-quinolinato) 4-phenylphenolate (abbreviated as BAlq) and other such aluminum complexes, triazole derivatives, and phenanthroline derivatives such as 2,9-dimethyl-4,7-diphenyl-1,10-phenanthroline (abbreviated as BCP).

The thickness of the hole blocking layer is preferably 1 to 500 nm, more preferably 3 to 100 nm, and even more preferably 5 to 50 nm.

The hole blocking layer may have a single-layer structure composed of one or more types of the aforementioned materials, or may have a multilayer structure composed of a plurality of layers of the same composition or different compositions.

From the standpoints of color purity, luminous efficiency, and drive durability, the material used in the hole blocking layer preferably has [a $T_1$ energy] higher than the $T_1$ energy of the aforementioned phosphorescent material. The $T_1$ in a film state of the material used in the hole blocking layer is preferably at least 0.1 eV higher than the $T_1$ of the phosphorescent material, more preferably at least 0.2 eV higher, and even more preferably at least 0.3 eV higher.

(B-3) Materials Especially Preferably Used in the Organic Layers Preferably Disposed between the Cathode and the Aforementioned Light-Emitting Layer In the organic electroluminescent element of the present invention, examples of materials especially preferably used as the materials of (B) the organic layers preferably disposed between the cathode and the aforementioned light-emitting layer include a compound expressed by General Formula 1 above, a compound expressed by General Formula P-1 below, and a compound expressed by General Formula O-1 below:

The organic electroluminescent element of the present invention preferably includes at least one organic layer between the light-emitting layer and the cathode, and from the standpoints of the drive voltage and efficiency of the element, this organic layer preferably contains at least one type of compound expressed by General Formula O-1 below. General Formula O-1 will be described below:

[Forty-Ninth Chemical Formula]

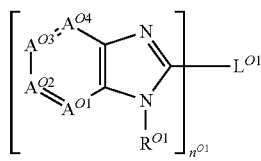

(O-1)

(In General Formula O-1, $R^{O1}$ represents an alkyl group, an aryl group, or a heteroaryl group. $A^{O1}$ to $A^{O4}$ represent each independently C—$R^A$ or a nitrogen atom. $R^A$ represents a hydrogen atom, an alkyl group, an aryl group, or a heteroaryl group, and the plurality of $R^A$ [groups] may be the same or different. $L^{O1}$ represents a divalent to hexavalent linking group composed of an aryl ring or a heteroaryl ring. $n^{O1}$ represents an integer from 2 to 6.)

$R^{O1}$ represents an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $R^{O1}$ is preferably an aryl group or a heteroaryl group and more preferably an aryl group. Substituents that are preferable when the aryl group of $R^{O1}$ has a substituent include an alkyl group, an aryl group, and a cyano group, with an alkyl group or aryl group being more preferable, and an aryl group being even more preferable. If the aryl group of $R^{O1}$ has a plurality of substituents, the plurality of substituents may be bound to each other to form a five- or six-membered ring. The aryl group of $R^{O1}$ is preferably a phenyl group that may have a substituent selected from Substituent Group A, more preferably a phenyl group that may be substituted with an alkyl group or an aryl group, and even more preferably an unsubstituted phenyl group or a 2-phenylphenyl group.

$A^{O1}$ to $A^{O4}$ represent each independently C—$R^A$ or a nitrogen atom. It is preferable for zero to two of $A^{O1}$ to $A^{O4}$ to be a nitrogen atom, and it is more preferable for zero or one to be a nitrogen atom. Preferably all of $A^{O1}$ to $A^{O4}$ are C—$R^A$, or $A^{O1}$ is a nitrogen atom and $A^{O2}$ to $A^{O4}$ are C—$R^A$, more preferably $A^{O1}$ is a nitrogen atom and $A^{O2}$ to $A^{O4}$ are C—$R^A$, and even more preferably $A^{O1}$ is a nitrogen atom, $A^{O2}$ to $A^{O4}$ are C—$R^A$, and all of the $R^A$ [groups] are hydrogen atoms.

$R^A$ represents a hydrogen atom, an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. Furthermore, the plurality of $R^A$ [groups] may be the same or different. $R^A$ is preferably a hydrogen atom or an alkyl group and more preferably a hydrogen atom.

$L^{O1}$ represents a divalent to hexavalent linking group composed of an aryl ring (preferably $C_6$ to $C_{30}$) or a heteroaryl ring (preferably $C_4$ to $C_{12}$). $L^{O1}$ is preferably an arylene group, a heteroarylene group, an aryltolyl group, or a heteroaryltolyl group, more preferably a phenylene group, a biphenylene group, or a benzenetriyl group, and even more preferably a biphenylene group or a benzenetriyl group. $L^{O1}$ may have a substituent selected from the aforementioned Substituent Group A, and if there is a substituent, the substituent is preferably an alkyl group, an aryl group, or a cyano group. Concrete examples of $L^{O1}$ are listed below:

[Fiftieth Chemical Formula]

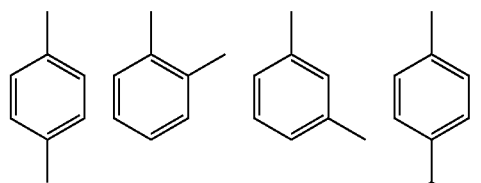
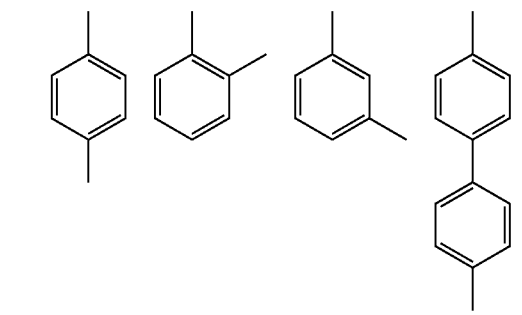
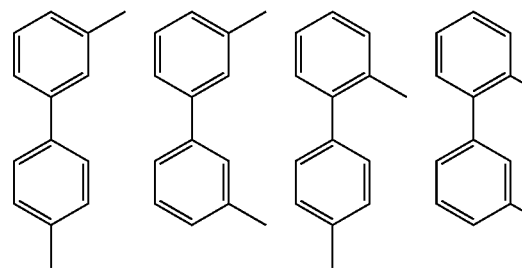
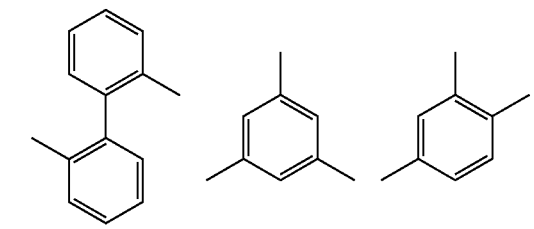
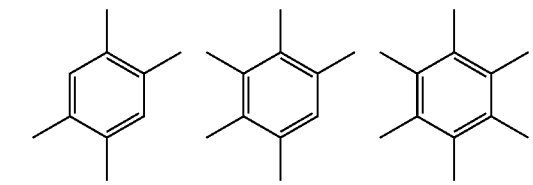
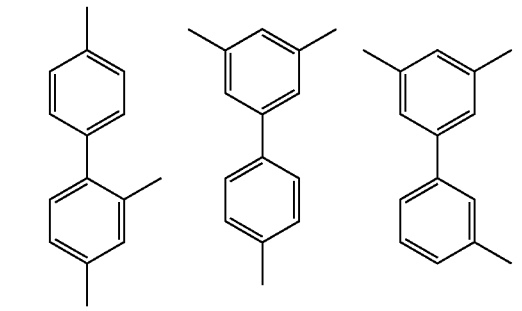

-continued

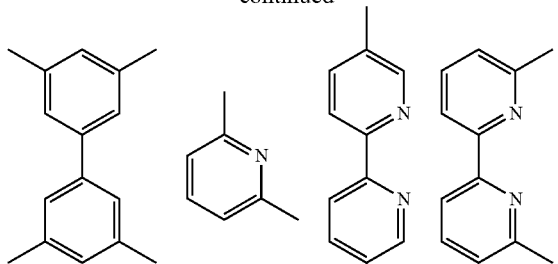
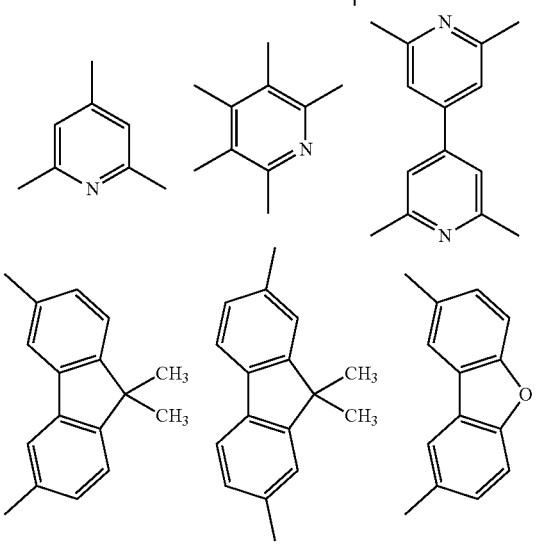
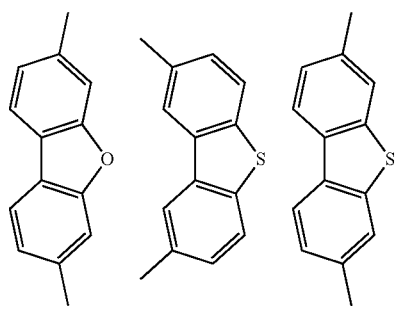
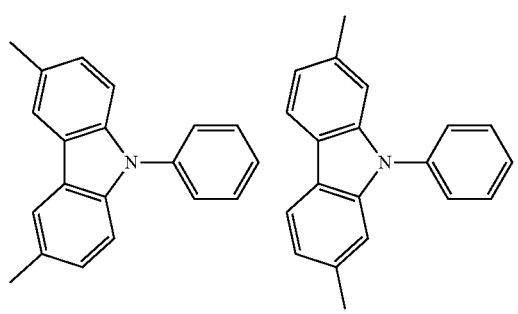

$n^{O1}$ represents an integer from 2 to 6, preferably an integer from 2 to 4, and more preferably 2 or 3. From the standpoint of efficiency of the element, $n^{O1}$ is most preferably 3, and from the standpoint of durability of the element, 2 is most preferable.

The compound expressed by General Formula O-1 is more preferably a compound expressed by General Formula O-2 below:

[Fify-First Chemical Formula]

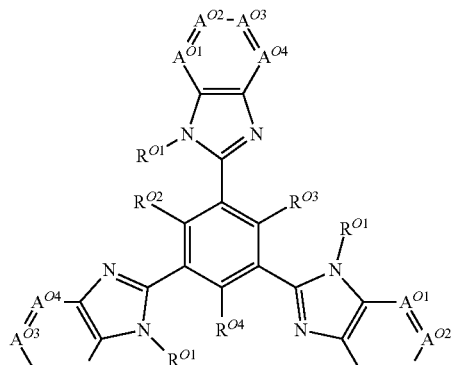

(O-2)

(In General Formula O-2, $R^{O1}$ represents an alkyl group, an aryl group, or a heteroaryl group. $R^{O2}$ to $R^{O4}$ represent each independently a hydrogen atom, an alkyl group, an aryl group, or a heteroaryl group. $A^{O1}$ to $A^{O4}$ represent each independently C—$R^A$ or a nitrogen atom. $R^A$ represents a hydrogen atom, an alkyl group, an aryl group, or a heteroaryl group, and the plurality of $R^A$ [groups] may be the same or different.)

$R^{O1}$ and $A^{O1}$ to $A^{O4}$ are defined the same as $R^{O1}$ and $A^{O1}$ to $A^{O4}$ in General Formula O-1 above, and the preferred ranges thereof are also the same.

$R^{O2}$ to $R^{O4}$ represent each independently a hydrogen atom, an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $R^{O2}$ to $R^{O4}$ are preferably a hydrogen atom, an alkyl group, or an aryl group, more preferably a hydrogen atom or an aryl group, and most preferably a hydrogen atom.

From the standpoints of stability during high-temperature storage and stable operation with respect to heat emission during high-temperature drive and during drive [sic], the glass transition temperature (Tg) of the compound expressed by General Formula O-1 above is preferably from 100° C. to 300° C., more preferably from 120° C. to 300° C., even more preferably from 120° C. to 300° C. [sic][7], and even still more preferably from 140° C. to 300° C.

[7] Translator's note: The phrase "from 120° C. to 300° C." is erroneously repeated in the original to describe even more preferable conditions.

Concrete examples of the compound expressed by General Formula O-1 are given below, but the present invention is not limited to or by these:

[Fifty-Second Chemical Formula]
OM-1
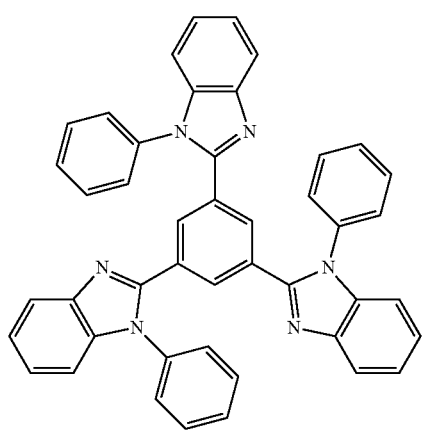
OM-2
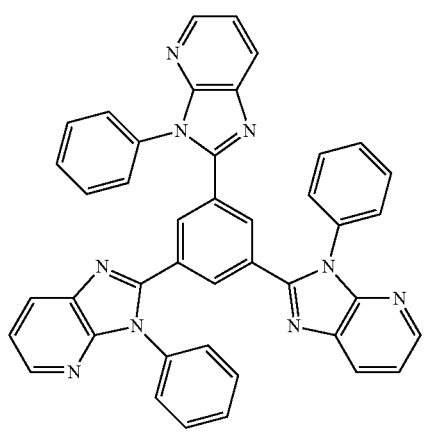
OM-3
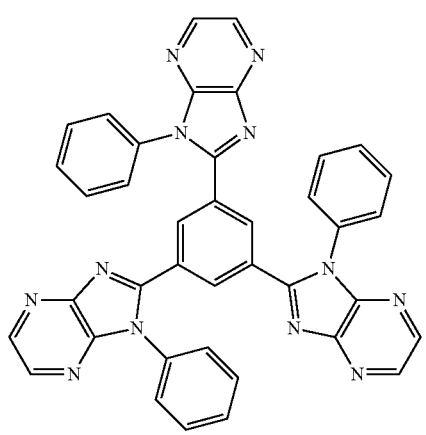
OM-4
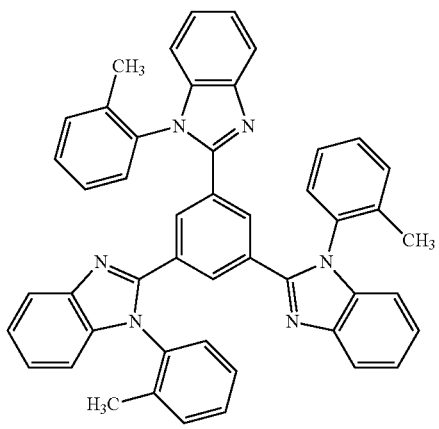
OM-5
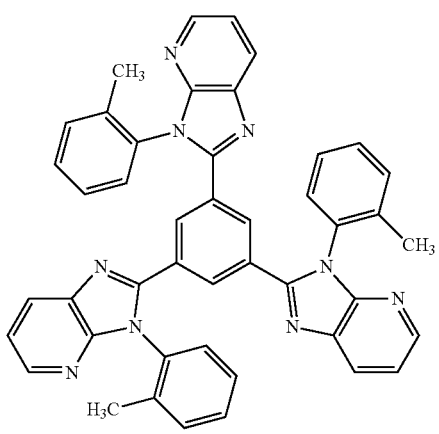
OM-6
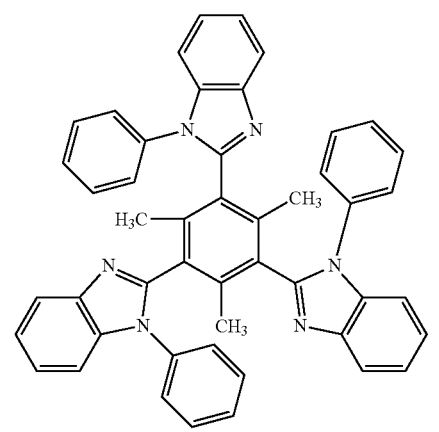

OM-7
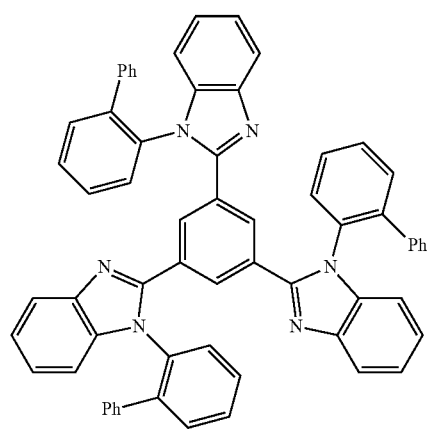
OM-8
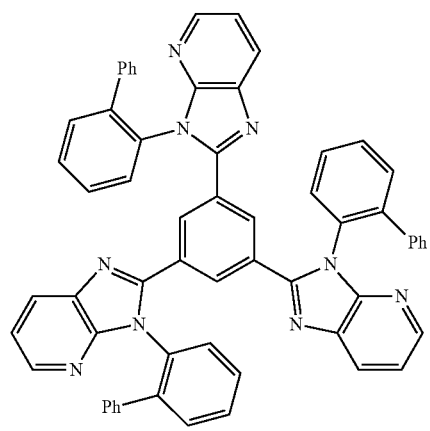
OM-9
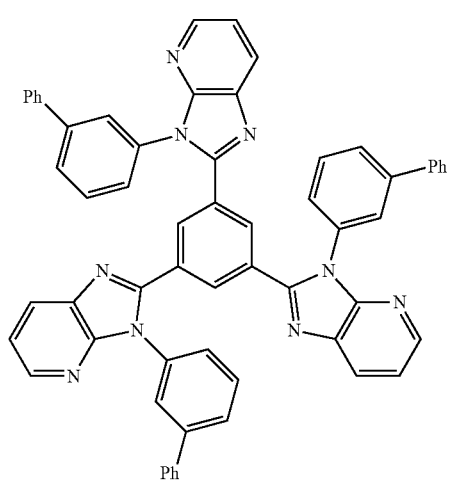
[Fifty-Third Chemical Formula]
OM-10
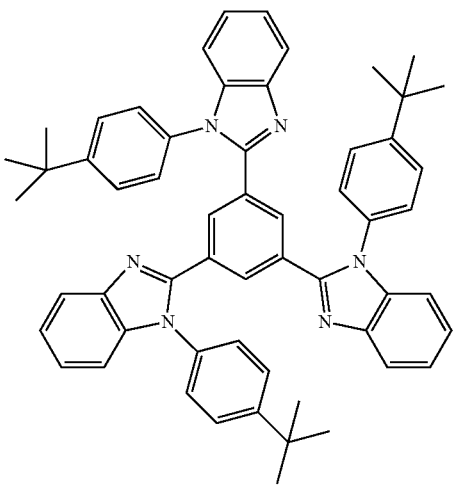
OM-11
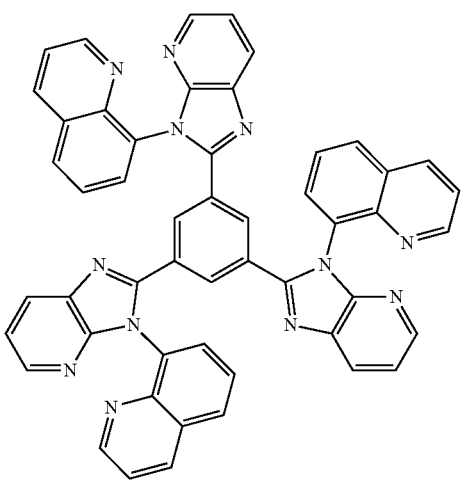
OM-12
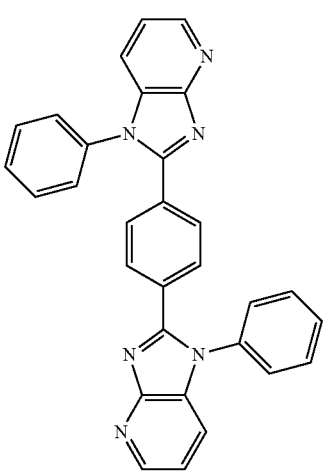

OM-13

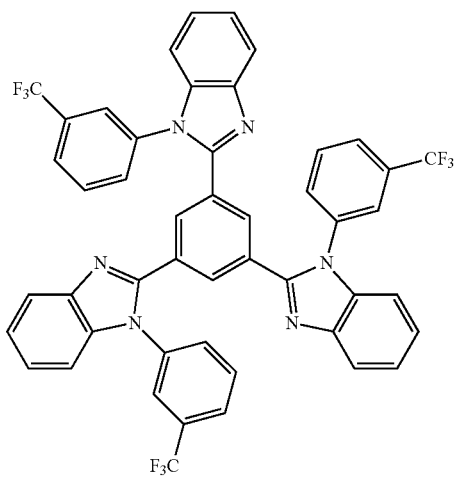

OM-14

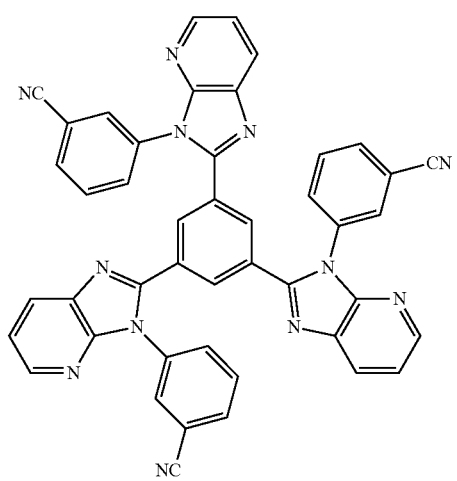

OM-15

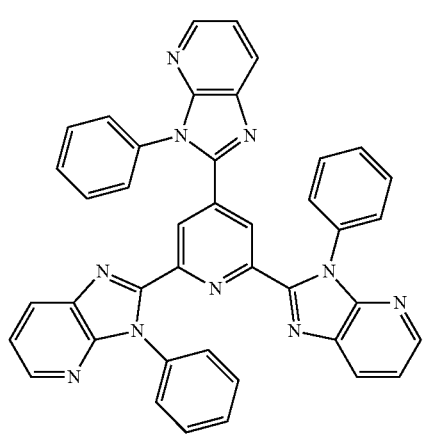

OM-16

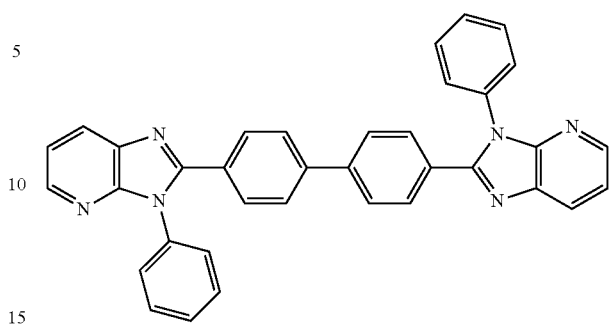

The compound expressed by General Formula O-1 above can be synthesized by the method described in Japanese Laid-Open Patent Application 2001-335776. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescent element of the present invention, the compound expressed by General Formula O-1 is preferably contained in an organic layer between the light-emitting layer and the cathode, but is more preferably contained in the layer adjacent to the light-emitting layer on the cathode side.

The compound expressed by General Formula O-1 is preferably contained in an amount of 70 to 100 wt % and more preferably 85 to 100 wt % with respect to the total weight of the organic layer to which [this compound is] added.

The organic electroluminescent element of the present invention preferably includes at least one organic layer between the light-emitting layer and the cathode, and from the standpoints of the drive voltage and efficiency of the element, this organic layer preferably contains at least one type of compound expressed by General Formula P below. General Formula P will be described below:

[Fifty-Fourth Chemical Formula]

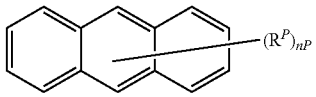

General Formula P

In General Formula P, $R^P$ represents an alkyl group (preferably $C_1$ to $C_8$), an aryl group (preferably $C_6$ to $C_{30}$), or a heteroaryl group (preferably $C_4$ to $C_{12}$), and these may have substituents selected from the aforementioned Substituent Group A. nP represents an integer from 1 to 10, and if there are a plurality of $R^P$ [groups], these may be the same or different. At least one $R^P$ is a substituent expressed by General Formulas P-1 to P-3 below:

[Fifty-Fifth Chemical Formula]

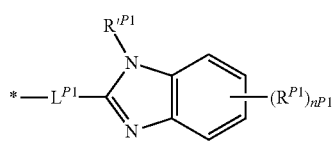

General Formula P-1

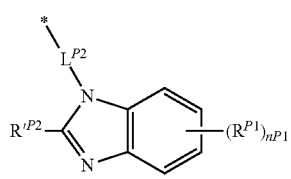

General Formula P-2

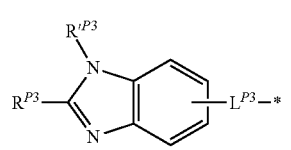

General Formula P-3

(In General Formulas P-1 to P-3, $R^{P1}$ to $R^{P3}$ and $R'^{P1}$ to $R'^{P3}$ represent each [independently] an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $n^{P1}$ and $n^{P2}$ represent an integer from 0 to 4, and if there are a plurality of $R^{P1}$ to $R^{P3}$ and $R'^{P1}$ to $R'^{P3}$ [groups], these may be the same or different. $L^{P1}$ to $L^{P3}$ represent either a single bond or a divalent linking group composed of an aryl ring or a heteroaryl ring. The asterisk indicates the bonding position with an anthracene ring in General Formula P.)

A substituent favorable as $R^P$ other than the substituents expressed by P-1 to P-3 is an aryl group, and more preferably a phenyl group, a biphenyl group, a terphenyl group, or a naphthyl group, with a naphthyl group being even more preferable.

$R^{P1}$ to $R^{P3}$ and $R'^{P1}$ to $R'^{P3}$ are preferably either an aryl group or a heteroaryl group, more preferably an aryl group, and even more preferably a phenyl group, a biphenyl group, a terphenyl group, or a naphthyl group, with a phenyl group being most preferable.

$L^{P1}$ to $L^{P3}$ are preferably either a single bond or a divalent linking group composed of an aryl ring, more preferably a single bond, phenylene, biphenylene, terphenylene, or naphthylene, and even more preferably a single bond, phenylene, or naphthylene.

Concrete examples of the compounds expressed by General Formula P are given below, but the present invention is not limited to or by these:

[Fifty-Sixth Chemical Formula]

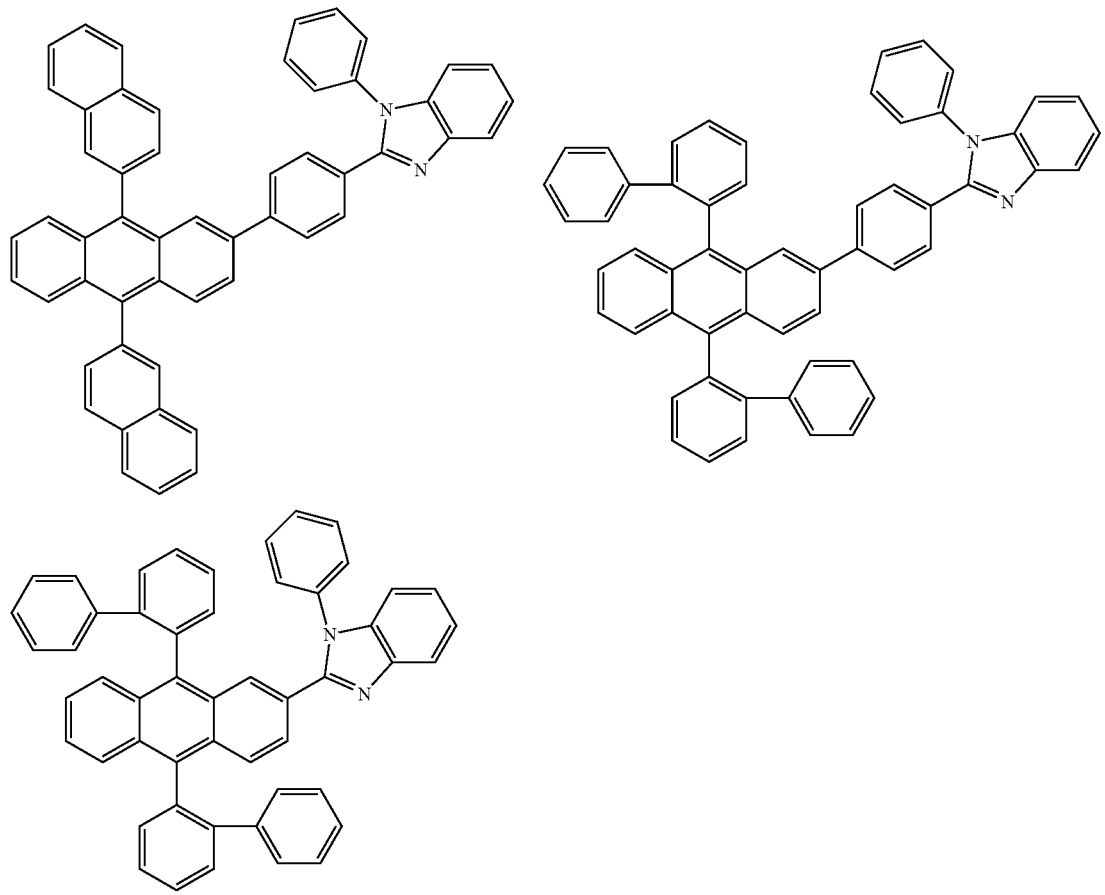

-continued
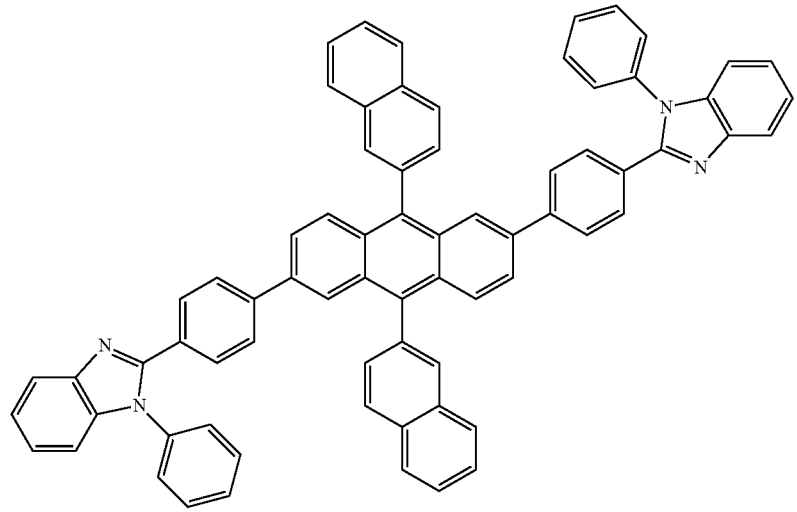
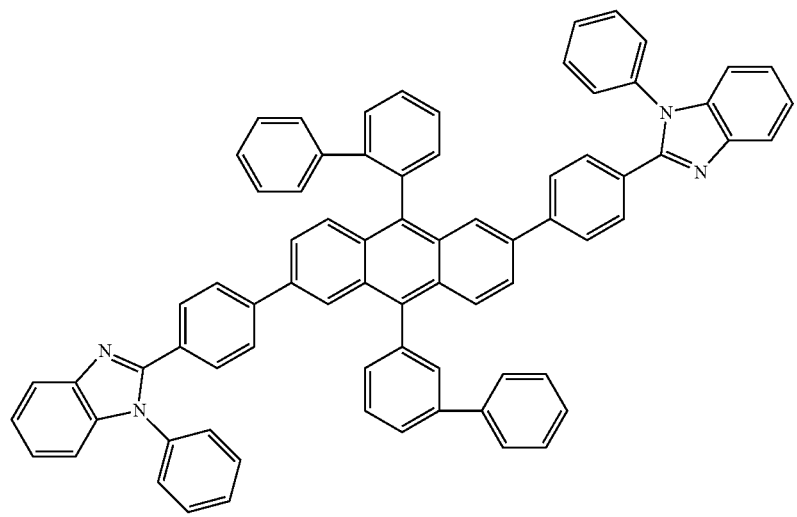
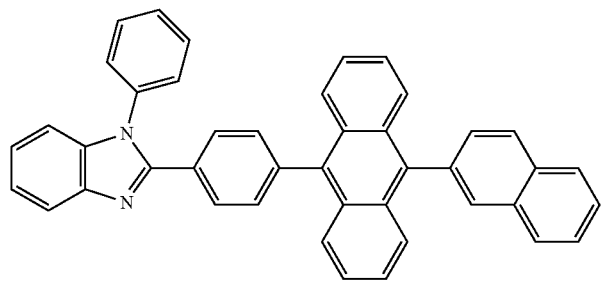
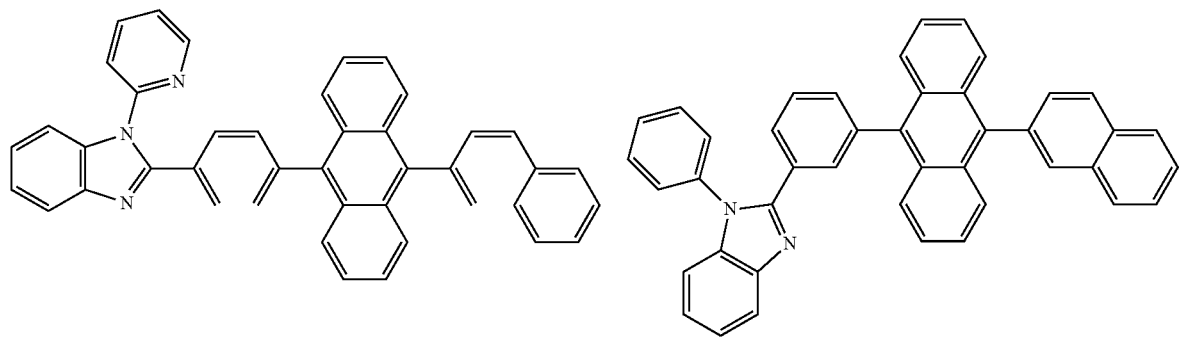

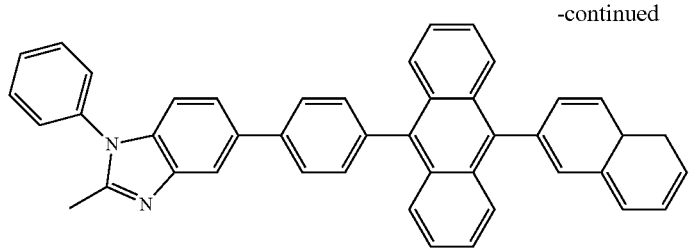

[Fifty-Seventh Chemical Formula]

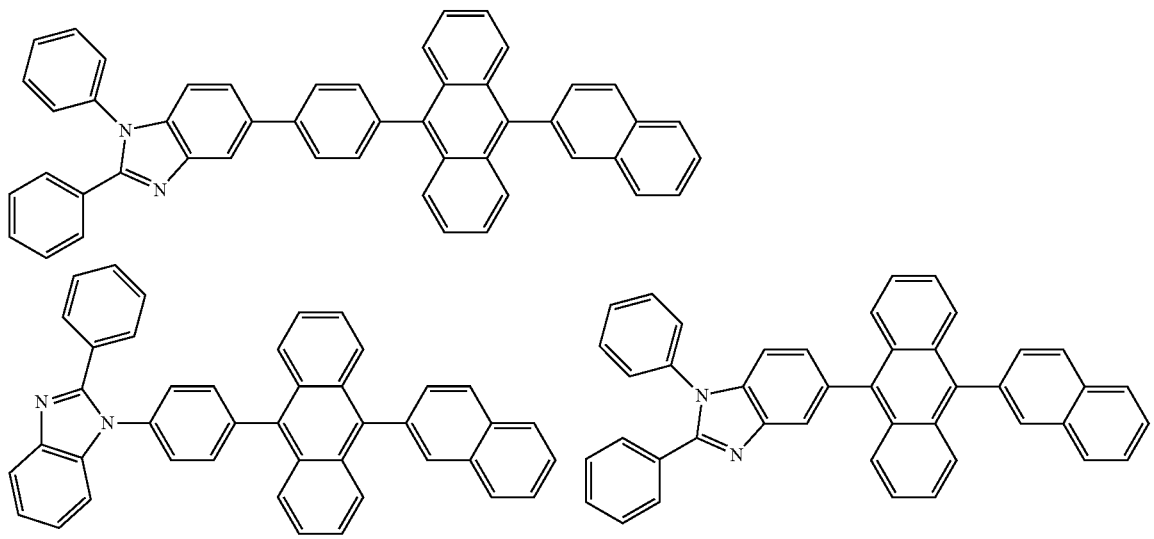

The compounds expressed by General Formula P above can be synthesized by the methods described in WO 2003/060956, WO 2004/080975, and the like. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescent element of the present invention, the compound expressed by General Formula P is preferably contained in an organic layer between the light-emitting layer and the cathode, but is more preferably contained in the layer adjacent to the cathode.

The compound expressed by General Formula P is preferably contained in an amount of 70 to 100 wt % and more preferably 85 to 100 wt % with respect to the total weight of the organic layer to which [this compound is] added.

<Protective Layer>

In the present invention, the entire organic electroluminescent element may be protected by a protective layer.

Regarding the protective layer, what is stated in paragraph numbers [0169] and [0170] in Japanese Laid-Open Patent Application 2008-270736 can be applied to the present invention. Note that the material of the protective layer may be either an inorganic material or organic material.

<Sealing Container>

The organic electroluminescent element of the present invention may be entirely sealed by using a sealing container.

Regarding the sealing container, what is stated in paragraph number [0171] in Japanese Laid-Open Patent Application 2008-270736 can be applied to the present invention.

<Drive Method>

The organic electroluminescent element of the present invention can emit light by applying direct current (may include an alternating current component as needed) voltage (usually 2 to 15 volts) or DC current between the anode and the cathode.

For the method for driving the organic electroluminescent element of the present invention, it is possible to apply the drive methods described in the respective Specifications or the like of Japanese Laid-Open Patent Applications H2-148687, H6-301355, H5-29080, H7-134558, H8-234685, and H8-241047, Japanese Patent 2,784,615, and U.S. Pat. Nos. 5,828,429 and 6,023,308.

The external quantum efficiency of the organic electroluminescent element of the present invention is preferably at least 7%, more preferably at least 10%, and even more preferably at least 12%. The numerical value of the external quantum efficiency that can be used is the maximum value for external quantum efficiency when the element is driven at 20° C., or the value for external quantum efficiency near 300 to 400 cd/m$^2$ when the element is driven at 20° C.

The internal quantum efficiency of the organic electroluminescent element of the present invention is preferably at least 30%, more preferably at least 50%, and [even] more preferably at least 70%. The internal quantum efficiency of the element is calculated by dividing the external quantum efficiency by the light extraction efficiency. The light extraction efficiency is approximately 20% with an ordinary organic EL element, but the light extraction efficiency can be raised to over 20% by modifying the shape of the substrate, the shape of the electrodes, the thickness of the organic layers, the thickness of the inorganic layers, the refractive index of the organic layers, the refractive index of the inorganic layers, and so forth.

<Emission Wavelength>

There are no particular restrictions on the emission wavelength of the organic electroluminescent element of the present invention. For example, of the three primary colors of light, it may be used for emission of red light, for emission of green light, or for emission of blue light. Of these, the organic electroluminescent element of the present invention preferably has an emission wavelength of 500 to 700 nm from the standpoint of the lowest excited triplet ($T_1$) energy of the compound expressed by General Formula 1 above.

In concrete terms, when a compound expressed by General Formula 1 above is used as the host material of the light-emitting layer in the organic electroluminescent element of the present invention, the emission wavelength is preferably from 500 to 700 nm, more preferably from 520 to 650 nm, and especially preferably from 520 to 550 nm.

Meanwhile, when a compound expressed by General Formula 1 above is used as the charge transport material of the hole blocking layer in the organic electroluminescent element of the present invention, the emission wavelength is preferably from 400 to 700 nm, more preferably from 450 to 650 nm, and especially preferably from 500 to 650 nm.

<Applications of the Organic Electroluminescent Element of the Present Invention>

The organic electroluminescent element of the present invention can be utilized favorably in display elements, displays, backlights, electronic photography, illumination light sources, recording light sources, exposure light sources, reading light sources, road signs, trade signs, interior decorating, optical communications, and so forth. [This element] can be especially favorably used in devices that are driven in areas of high light emission brightness, such as in light-emitting devices, illumination devices, and display devices.

Light-Emitting Device

The light-emitting device of the present invention is characterized by including the organic electroluminescent element of the present invention.

Next, the light-emitting device of the present invention will be described with reference to FIG. 2.

The light-emitting device of the present invention makes use of the aforementioned organic electroluminescent element.

Figure 2:
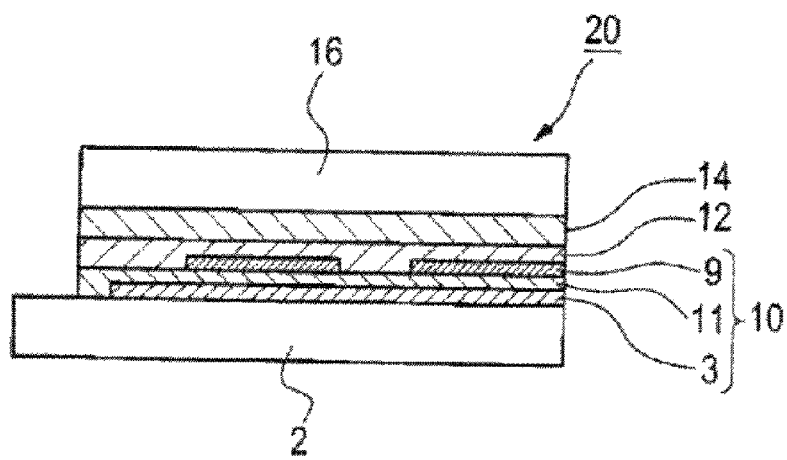
FIG. 2 is a schematic diagram illustrating one example of the light-emitting device according to the present invention.

FIG. 2 is a sectional view schematically showing one example of the light-emitting device of the present invention. The light-emitting device 20 in FIG. 2 is made up of a transparent substrate (supporting substrate) 2, an organic electroluminescent element 10, a sealing container 16, and the like.

The organic electroluminescent element 10 is configured such that an anode (first electrode) 3, an organic layer 11, and a cathode (second electrode) 9 are sequentially laminated over the substrate 2. Furthermore, a protective layer 12 is laminated over the cathode 9, and in addition, the sealing container 16 is provided on the protective layer 12 via an adhesive layer 14. Note that parts of the electrodes 3 and 9, partitions, insulating layers, and so forth are not depicted.

Here, an epoxy resin or other such photosetting adhesive or thermosetting adhesive can be used as the adhesive layer 14. For example, a thermosetting adhesive sheet can also be used.

There are no particular restrictions on the applications of the light-emitting device of the present invention, but examples other than illumination devices include television sets, personal computers, portable telephones, electronic paper, and other such display devices.

Illumination Device

The illumination device of the present invention is characterized by including the organic electroluminescent element of the present invention.

Next, the illumination device of the present invention will be described with reference to FIG. 3.

Figure 3:
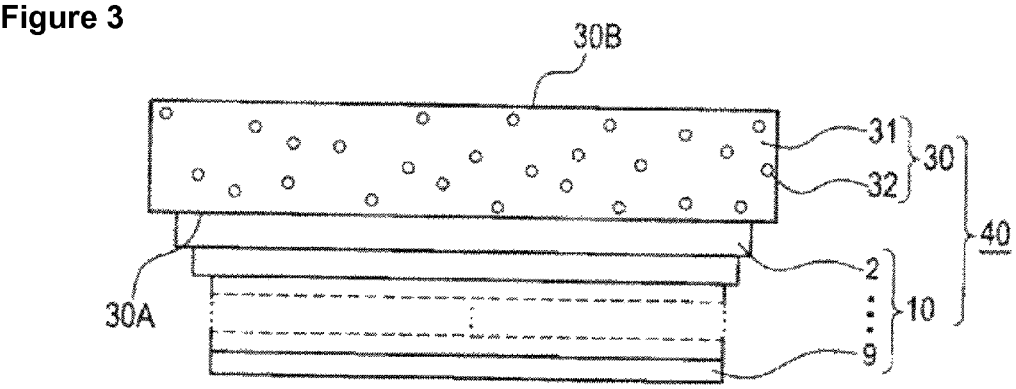
FIG. 3 is a schematic diagram illustrating one example of the illumination device according to the present invention.

FIG. 3 is a sectional view schematically showing one example of the illumination device of the present invention. As is shown in FIG. 3, the illumination device 40 of the present invention comprises the aforementioned organic EL element 10 and a light-scattering member 30. More concretely, the illumination device 40 is configured such that the substrate 2 of the organic EL element 10 is in contact with the light-scattering member 30.

There are no particular restrictions on the light-scattering member 30 as long as it is capable of scattering light, but in FIG. 3, it is a member in which microparticles 32 are dispersed in a transparent substrate 31. A glass substrate, for example, can be used favorably as the transparent substrate 31. Transparent resin microparticles can be used favorably as the microparticles 32. The glass substrate and the transparent resin microparticles can both be from prior art. This type of illumination device 40 is devised such that when light emitted from the organic electroluminescent element 10 is incident on a light incidence face 30A of the light-scattering member 30, the incident light is scattered by the light-scattering member 30, and the scattered light exits a light emission face 30B as illuminating light.

Display Device

The display device of the present invention is characterized by including the organic electroluminescent element of the present invention.

Examples of the display device of the present invention include television sets, personal computers, portable telephones, electronic paper, and other such display devices.

Working Examples

The present invention will be described below in more concrete terms by giving working examples. The materials, usage amounts, proportions, processing details and procedures, and so forth mentioned in the following working examples can be suitably modified as long as this does not depart from the gist of the present invention. Therefore, the scope of the present invention is not limited to or by the concrete examples given below.

1. Synthesis Example

The compound expressed by General Formula 1 above can be synthesized by the method described in Japanese Translation of PCT International Application 2010-535809 or by a combination of other known reactions.

(Synthesis Example 1) Synthesis of Compound 2

[Fifty-Eighth Chemical Formula]

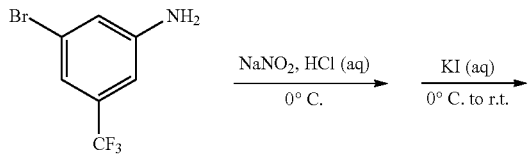

-continued

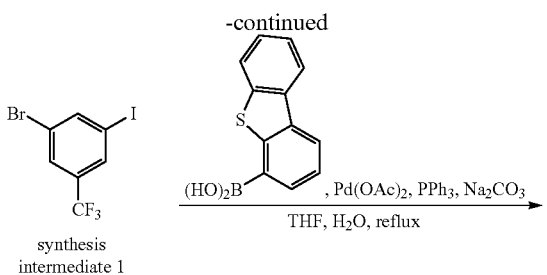

synthesis intermediate 1

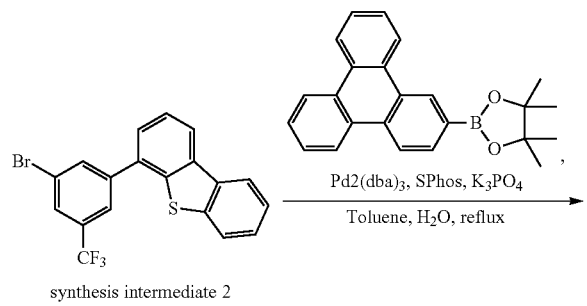

synthesis intermediate 2

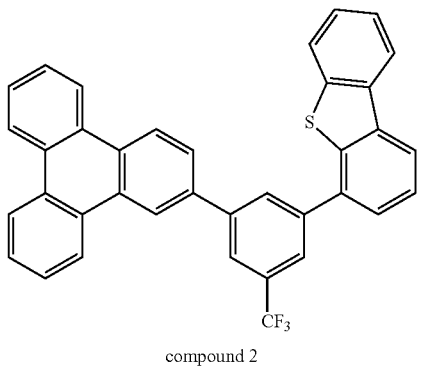

compound 2

10.0 g (41.7 mmol) of 3-amino-5-bromobenzotrifluoride, 40 mL of pure water, and 20 mL of concentrated hydrochloric acid were stirred in an ice bath. Into this was slowly dropped a solution obtained by dissolving 3.74 g (54.2 mmol) of sodium nitrite in 15 mL of pure water. [This was] stirred for one hour, after which a solution obtained by dissolving 13.8 g (83.4 mmol) of potassium iodide in 20 mL of pure water was slowly added dropwise, and [the system] was allowed to stand for one hour. After an hour, the ice bath was removed, and [the system] was stirred for additional one hour while being allowed to return naturally to room temperature. Toluene and pure water were added to the reaction solution, and the liquids were separated, after which the organic layer was washed with a sodium thiosulfate aqueous solution. The organic layer was concentrated, after which it was purified by silica gel column chromatography (developing medium: hexane/ethyl acetate (9:1)), which gave 11.0 g of an oily synthesis intermediate 1 (75% yield).

5.00 g (14.2 mmol) of the synthesis intermediate 1, 3.24 g (14.2 mmol) of dibenzothiophene-4-boronic acid, 0.16 g (0.71 mmol) of palladium acetate, 0.75 g (2.84 mmol) of triphenylphosphine, and 4.52 g (42.6 mmol) of dehydrated tetrahydrofuran were mixed, and [the mixture] was heated to reflux for 6.5 hours under a nitrogen atmosphere. After the reaction solution was returned to room temperature, toluene was added to separate the liquids, and the organic layer was purified by silica gel column chromatography (developing medium: toluene). Afterward, [the product] was washed first with methanol and then with hexane, which gave 2.80 g of synthesis intermediate 2 (48% yield).

1.40 g (3.44 mmol) of the synthesis intermediate 2, 1.46 g (4.13 mmol) of 4,4,5,5-tetramethyl-2-(triphenylen-2-yl)-1,3,2-dioxaborane, 0.094 g (0.10 mmol) of tris-(dibenzylideneacetone)dipalladium ($Pd_2(dba)_3$), 0.17 g (0.41 mmol) of 2-dicyclohexylphosphino-2',6'-dimethoxybiphenyl (SPhos), 2.92 g (13.8 mmol) of potassium phosphate, 10 mL of toluene, and 10 mL of water were mixed and heated to reflux for 5 hours under a nitrogen atmosphere. The reaction solution was returned to room temperature, and the precipitated solids were filtered off. The solid thus obtained was heated to reflux in THF and completely dissolved, after which 20 mL of toluene was added, the THF was distilled off under heating to reflux, and [the system] was returned to room temperature. The precipitated solids were filtered off and washed with toluene, which gave 1.30 g of compound 2 (68% yield).

NMR Data for Compound 2

$^1$H-NMR (400 MHz, in DMSO-$d_6$); δ (ppm)=9.27 (s, 1H), 9.15-9.12 (m, 1H), 8.98 (d, 1H), 8.91-8.84 (m, 3H), 8.66 (s, 1H), 8.53-8.44 (m, 3H), 8.25-8.22 (m, 1H), 8.15 (s, 1H), 8.09-8.07 (m, 1H), 7.88 (d, 1H), 7.77-7.72 (m, 5H), 7.60-7.54 (m, 2H) ppm.

Compound 1 and compounds 3 to 10 were also synthesized by the same synthesis method as compound 2.

2. Element Production and Evaluation

All the materials used in the production of the elements were subjected to sublimation purification, and it was confirmed by high-performance liquid chromatography (Tosoh TSK gel ODS-100Z) that the purity (absorption intensity surface area ratio at 254 nm) was 99.9% or higher. Note that comparative compounds 1 and 2 are respectively the compounds 2S and 2O described in Japanese Translation of PCT International Application 2010-535809, while comparative compound 3 is the compound 3-45 described in International Laid-Open WO 2009/074087.

Working Example 1

A glass substrate (made by Geomatec Co., surface resistance of 10 ohms/square) having an ITO film measuring 2.5 $cm^2$ and 0.5 mm thick was put into a washing vessel and ultrasonically washed in 2-propanol, after which it was subjected to treatment with UV-ozone for 30 minutes. The following organic compound layers were sequentially deposited onto this transparent anode (ITO film) by a vacuum vapor deposition method:

First layer: HAT-CN; film thickness of 10 nm
Second layer: NPD; film thickness of 30 nm
Third layer: host material listed in Table 1 and GD-1 (weight ratio of 90:10); film thickness of 30 nm
Fourth layer: HBL material listed in Table 1; film thickness of 5 nm
Fifth layer: Alq; film thickness of 45 nm Over this, lithium fluoride was vapor-deposited in a thickness of 0.1 nm, followed by metallic aluminum in a thickness of 100 nm, which gave a cathode.

The laminate thus obtained was put in a glovebox that had been replaced with nitrogen gas without coming into contact with the air, and was sealed using a glass sealing jar and a UV-setting adhesive (XNR5516HV, made by Nagase Chiba[8]), which gave elements 1-1 to 1-7 and comparative elements 1-1 to 1-5. The light-emitting portion was a square measuring 2 mm×2 mm. These elements were evaluated by the following methods for efficiency, drive voltage, durability, and efficiency after high-temperature storage, the results of which are given in Table 1.

[8] Translator's note: "Nagase Chiba" is now called "Nagase ChemteX."

firmed in six or more elements, this is indicated by "xx," by "x" if the presence of dark spots is confirmed in from two to five elements, and by "◯" if the presence of dark spots is confirmed in one or zero elements.

TABLE 1

| Element name | Host material | HBL material | Emission color | Element characteristics after high-temperature storage | | Dark spots |
|---|---|---|---|---|---|---|
| | | | | Efficiency (relative value) | Drive durability (relative value) | |
| element 1-1 | compound 1 | ET-1 | green | 1.9 | 1.4 | ◯ |
| element 1-2 | compound 4 | ET-1 | green | 1.8 | 1.6 | ◯ |
| element 1-3 | compound 7 | ET-1 | green | 2.1 | 1.9 | ◯ |
| element 1-4 | compound 8 | ET-1 | green | 1.8 | 1.4 | ◯ |
| element 1-5 | compound 9 | ET-1 | green | 2.0 | 2.1 | ◯ |
| element 1-6 | compound 1 | compound 1 | green | 1.9 | 1.7 | ◯ |
| element 1-7 | compound 4 | compound 3 | green | 1.9 | 1.8 | ◯ |
| element 1-8 | compound 7 | compound 5 | green | 2.1 | 2.0 | ◯ |
| comparative element 1-1 | comparative compound 1 | ET-1 | green | 1.0 (reference) | 1.0 (reference) | xx |
| comparative element 1-2 | comparative compound 2 | ET-1 | green | 0.9 | 0.7 | xx |
| comparative element 1-3 | comparative compound 3 | ET-1 | green | 0 (No emission) | — (Measurement added)[9] | — |

[9]Translator's note: "(Measurement added)" here may be a typological error in the original for "(Measurement impossible)," which happens to be homophonous in Japanese.

(a) Efficiency After High-Temperature Storage

Each element was stored for 100 hours in a 105° C. constant-temperature tank, after which a source measurement unit 2400 (made by the Toyo Corporation) was used to apply DC voltage to each element to make it emit light, and the brightness thereof was measured using a BM-8 brightness meter made by Topcon Corporation. Based on these [results], the external quantum efficiency ($\eta$) at a brightness of close to 1000 cd/m$^2$ was calculated by brightness conversion. The value for comparative element 1-1 in Table 1, the value for comparative element 2-1 in Table 2, the value for comparative element 3-1 in Table 3, the value for comparative element 4-1 in Table 4, the value for comparative element 5-1 in Table 5, and the value for comparative element 6-1 in Table 6 are each given as 1.0, with [the other values] in each of the tables being relative values. For efficiency, the greater the numerical value, the better.

(b) Drive Durability After High-Temperature Storage

Each element was stored for 100 hours in a 105° C. constant-temperature tank, after which DC voltage was applied to make each element emit light continuously such that the brightness would be 5000 cd/m$^2$, and the time it took for the brightness to drop to 4000 cd/m$^2$ was used as an index of durability. The value for comparative element 1-1 in Table 1, the value for comparative element 2-1 in Table 2, the value for comparative element 3-1 in Table 3, the value for comparative element 4-1 in Table 4, the value for comparative element 5-1 in Table 5, and the value for comparative element 6-1 in Table 6 are each given as 1.0, with [the other values] in each of the tables being relative values. For durability, the greater the numerical value, the better.

(c) Dark Spots

Ten elements were produced under the same conditions, and while each element was made to emit light at a brightness of 4000 cd/m$^2$, the light-emitting surface was observed under a microscope. If the presence of dark spots is con- It can be seen from Table 1 above that the organic electroluminescent elements of the respective working examples in which the compounds expressed by General Formula 1 (compounds 1, 4, and 7 to 9) were used as the host compound of the light-emitting layer all had good drive durability and efficiency after high-temperature storage, and no dark spots were noted.

On the other hand, the organic electroluminescent elements in Comparative Examples 1 and 2 used comparative compounds 1 and 2 as the host compound for the light-emitting layer, and the drive durability and efficiency after high-temperature storage were poor, and the generation of dark spots was pronounced. Furthermore, with comparative element 1-3 that used comparative compound 3, no emission of light from the light-emitting material GD-1 could be confirmed.

Note that the emission wavelength of the organic electroluminescent elements produced in Working Example 1 was from 522 to 528 nm.

Working Example 2

Elements were produced in the same manner as in Working Example 1, except that the layer configuration was changed as follows. An evaluation was carried out in the same manner as in Working Example 1, the results of which are given in Table 2.

First layer: 2-TNATA and F$_4$-TCNQ (weight ratio of 99.7:0.3); film thickness of 160 nm Second layer: NPD; film thickness of 5 nm Third layer: HT-1; film thickness of 3 nm Fourth layer: H-1 and GD-2 (weight ratio of 85:15); film thickness of 30 nm Fifth layer: HBL material listed in Table 2; film thickness of 10 nm Sixth layer: ET-2; film thickness of 20 nm

TABLE 2

| Element name | HBL material | Emission color | Element characteristics after high-temperature storage | | Dark spots |
| --- | --- | --- | --- | --- | --- |
| | | | Efficiency (relative value) | Drive durability (relative value) | |
| element 2-1 | compound 2 | green | 1.4 | 1.4 | ○ |
| element 2-2 | compound 5 | green | 1.6 | 1.3 | ○ |
| element 2-3 | compound 6 | green | 1.5 | 1.3 | ○ |
| comparative element 2-1 | comparative compound 1 | green | 1.0 (reference) | 1.0 (reference) | X |
| comparative element 2-2 | comparative compound 2 | green | 1.0 | 0.8 | X |

It can be seen from Table 2 above that the organic electroluminescent elements of the respective working examples in which the compounds expressed by General Formula 1 (compounds 2, 5, and 6) were used as the material of the hole blocking layer all had good drive durability and efficiency after high-temperature storage, and no dark spots were noted.

On the other hand, the organic electroluminescent elements in Comparative Examples 1 and 2 used comparative compounds 1 and 2 as the material for the hole blocking layer, and the drive durability and efficiency after high-temperature storage were poor, and the generation of dark spots was pronounced.

Note that the emission wavelength of the organic electroluminescent elements produced in Working Example 2 was from 503 to 507 nm.

Working Example 3

Elements were produced in the same manner as in Working Example 1, except that the layer configuration was changed as follows. An evaluation was carried out in the same manner as in Working Example 1, the results of which are given in Table 3.
First layer: CuPc; film thickness of 10 nm
Second layer: NPD; film thickness of 30 nm
Third layer: host material listed in Table 3 and RD-1 (weight ratio of 95:5); film thickness of 30 nm
Fourth layer: ET-2; film thickness of 5 nm
Fifth layer: ET-3; film thickness of 50 nm It can be seen from Table 3 above that the organic electroluminescent elements of the respective working examples in which the compounds expressed by General Formula 1 (compounds 3 to 5 and 10) were used as the host compound of the light-emitting layer all had good drive durability and efficiency after high-temperature storage, and no dark spots were noted.

On the other hand, the organic electroluminescent elements in Comparative Examples 1 and 2 used comparative compounds 1 and 2 as the host compound for the light-emitting layer, and the drive durability and efficiency after high-temperature storage were poor, and the generation of dark spots was pronounced.

Note that the emission wavelength of the organic electroluminescent elements produced in Working Example 3 was from 618 to 622 nm.

Working Example 4

Elements were produced in the same manner as in Working Example 1, except that the layer configuration was changed as follows. An evaluation was carried out in the same manner as in Working Example 1, the results of which are given in Table 4.
First layer: TCTA; film thickness of 35 nm
Second layer: HT-2; film thickness of 5 nm
Third layer: BAlq and RD-2 (weight ratio of 90:10); film thickness of 30 nm
Fourth layer: HBL material listed in Table 4; film thickness of 5 nm
Fifth layer: ET-4; film thickness of 45 nm

TABLE 3

| Element name | Host material | Emission color | Element characteristics after high-temperature storage | | Dark spots |
| --- | --- | --- | --- | --- | --- |
| | | | Efficiency (relative value) | Drive durability (relative value) | |
| element 3-1 | compound 3 | red | 1.9 | 1.3 | ○ |
| element 3-2 | compound 4 | red | 1.7 | 1.5 | ○ |
| element 3-3 | compound 5 | red | 2.0 | 1.1 | ○ |
| element 3-4 | compound 10 | red | 1.9 | 1.9 | ○ |
| comparative element 3-1 | comparative compound 1 | red | 1.0 (reference) | 1.0 (reference) | XX |
| comparative element 3-2 | comparative compound 2 | red | 1.0 | 0.8 | XX |

TABLE 4

| Element name | HBL material | Emission color | Element characteristics after high-temperature storage | | Dark spots |
| | | | Efficiency (relative value) | Drive durability (relative value) | |
| --- | --- | --- | --- | --- | --- |
| element 4-1 | compound 3 | red | 1.4 | 1.3 | ○ |
| element 4-2 | compound 7 | red | 1.3 | 1.8 | ○ |
| element 4-3 | compound 8 | red | 1.4 | 1.3 | ○ |
| comparative element 4-1 | comparative compound 1 | red | 1.0 (reference) | 1.0 (reference) | ○ |
| comparative element 4-2 | comparative compound 2 | red | 1.0 | 0.9 | ○ |

It can be seen from Table 4 above that the organic electroluminescent elements of the respective working examples in which the compounds expressed by General Formula 1 (compounds 3, 7, and 8) were used as the material of the hole blocking layer all had good drive durability and efficiency after high-temperature storage, and no dark spots were noted.

On the other hand, the organic electroluminescent elements in Comparative Examples 1 and 2 used comparative compounds 1 and 2 as the material of the hole blocking layer, and the drive durability and efficiency after high-temperature storage were poor.

Note that the emission wavelength of the organic electroluminescent elements produced in Working Example 4 was from 625 to 629 nm.

Working Example 5

Elements were produced in the same manner as in Working Example 1, except that the layer configuration was changed as follows. An evaluation was carried out in the same manner as in Working Example 1, the results of which are given in Table 5.

First layer: HAT-CN; film thickness of 10 nm
Second layer: NPD; film thickness of 115 nm
Third layer: HT-3; film thickness of 5 nm
Fourth layer: H-2 and Firpic (weight ratio of 90:10); film thickness of 30 nm
Fifth layer: HBL material listed in Table 5; film thickness of 5 nm
Sixth layer: ET-5; film thickness of 25 nm It can be seen from Table 5 above that the organic electroluminescent elements of the respective working examples in which the compounds expressed by General Formula 1 (compounds 1, 2, and 6) were used as the material of the hole blocking layer all had good drive durability and efficiency after high-temperature storage, and no dark spots were noted. On the other hand, the organic electroluminescent elements in Comparative Examples 1 and 2 used comparative compounds 1 and 2 as the material for the hole blocking layer, and the drive durability and efficiency after high-temperature storage were poor, and the generation of dark spots was recognized.

Note that the emission wavelength of the organic electroluminescent elements produced in Working Example 5 was from 472 to 476 nm.

Working Example 6

Elements were produced in the same manner as in Working Example 1, except that the layer configuration was changed as follows. An evaluation was carried out in the same manner as in Working Example 1, the results of which are given in Table 6.

First layer: 2-TNATA and $F_4$ TCNQ (weight ratio of 99.7:0.3); film thickness of 120 nm
Second layer: NPD; film thickness of 7 nm
Third layer: HT-3; film thickness of 3 nm
Fourth layer: H-3 and BD-1 (weight ratio of 85:15); film thickness of 30 nm
Fifth layer: HBL material listed in Table 6; film thickness of 5 nm
Sixth layer: BAlq; film thickness of 25 nm

TABLE 5

| Element name | HBL material | Emission color | Element characteristics after high-temperature storage | | Dark spots |
| | | | Efficiency (relative value) | Drive durability (relative value) | |
| --- | --- | --- | --- | --- | --- |
| element 5-1 | compound 1 | aqua blue | 1.3 | 1.4 | ○ |
| element 5-2 | compound 2 | aqua blue | 1.2 | 1.3 | ○ |
| element 5-3 | compound 6 | aqua blue | 1.4 | 1.2 | ○ |
| comparative element 5-1 | comparative compound 1 | aqua blue | 1.0 (reference) | 1.0 (reference) | X |
| comparative element 5-2 | comparative compound 2 | aqua blue | 1.0 | 0.9 | X |

TABLE 6

| Element name | HBL material | Emission color | Element characteristics after high-temperature storage | | |
|---|---|---|---|---|---|
| | | | Efficiency (relative value) | Drive durability (relative value) | Dark spots |
| element 6-1 | compound 3 | blue | 1.4 | 1.5 | ○ |
| element 6-2 | compound 5 | blue | 1.4 | 1.2 | ○ |
| element 6-3 | compound 7 | blue | 1.3 | 1.7 | ○ |
| comparative element 6-1 | comparative compound 1 | blue | 1.0 (reference) | 1.0 (reference) | X |
| comparative element 6-2 | comparative compound 2 | blue | 0.9 | 0.8 | X |

It can be seen from Table 6 above that the organic electroluminescent elements of the respective working examples in which the compounds expressed by General Formula 1 (compounds 3, 5, and 7) were used as the material of the hole blocking layer all had good drive durability and efficiency after high-temperature storage, and no dark spots were noted.

On the other hand, the organic electroluminescent elements in Comparative Examples 1 and 2 used comparative compounds 1 and 2 as the material for the hole blocking layer, and the drive durability and efficiency after high-temperature storage were poor, and the generation of dark spots was recognized.

Note that the emission wavelength of the organic electroluminescent elements produced in Working Example 6 was from 455 to 460 nm.

[Fifty-Ninth Chemical Formula]

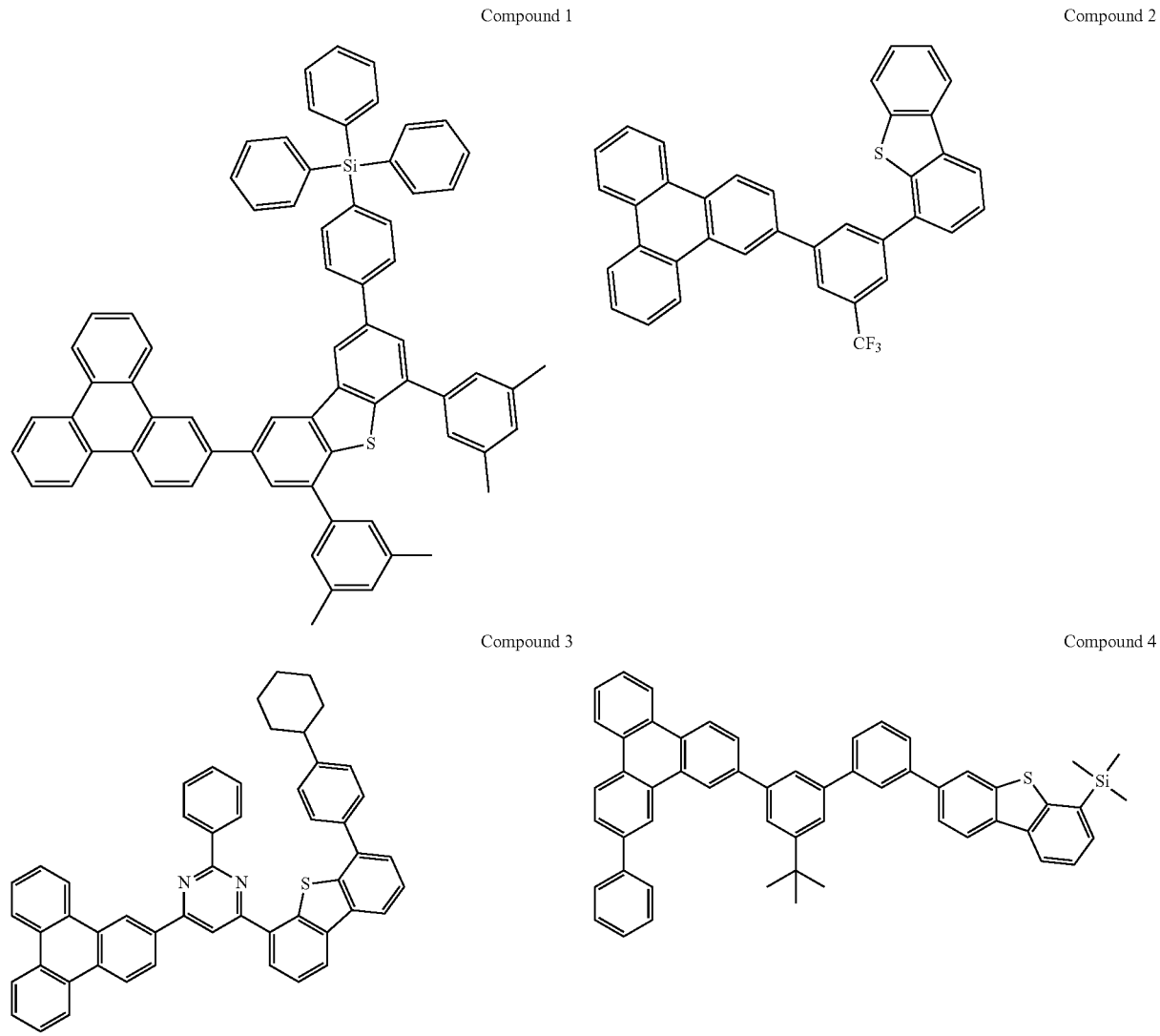

Compound 1

Compound 2

Compound 3

Compound 4

Compound 5
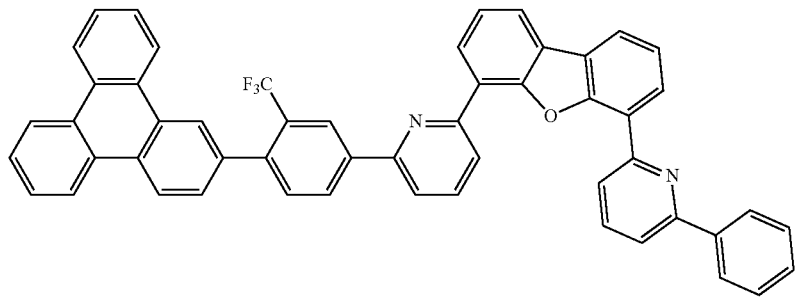
Compound 6
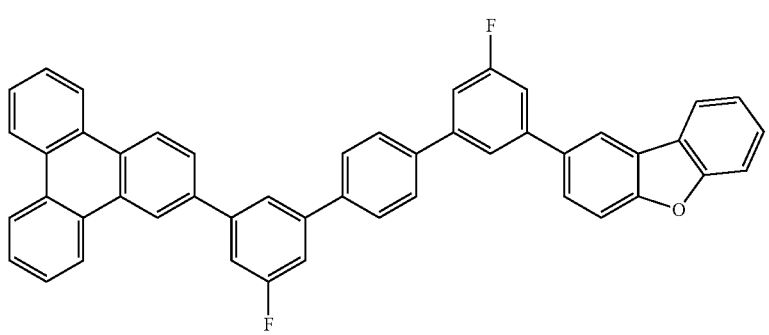
Compound 7
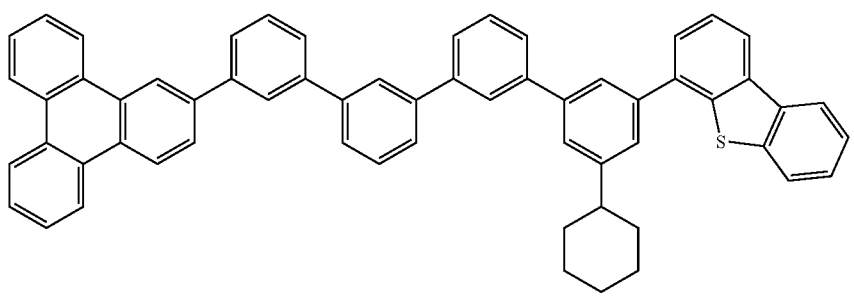
Compound 8
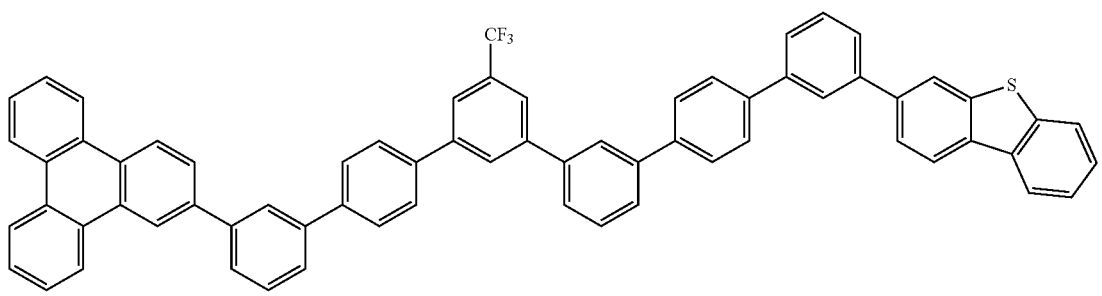
Compound 9
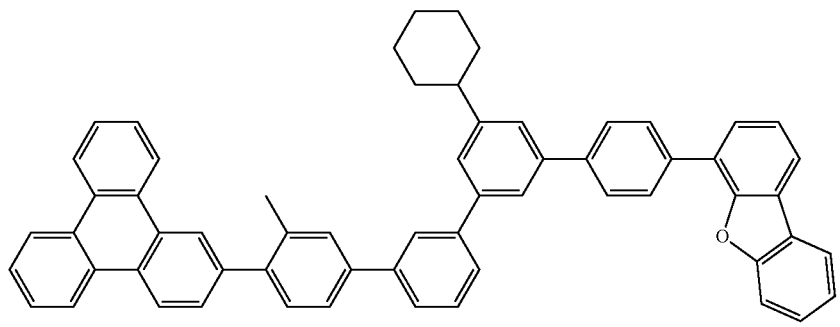

-continued
Compound 10
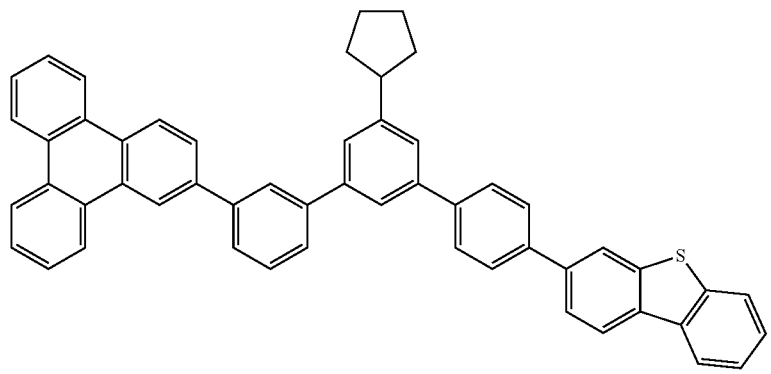
[Sixtieth Chemical Formula]
comparative compound 1
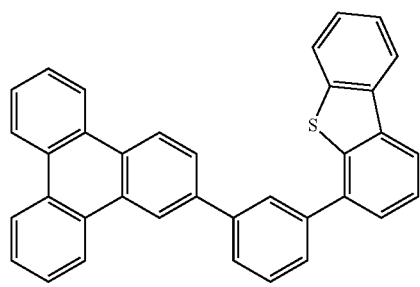
comparative compound 2
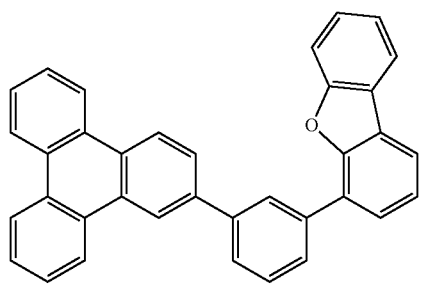
comparative compound 3
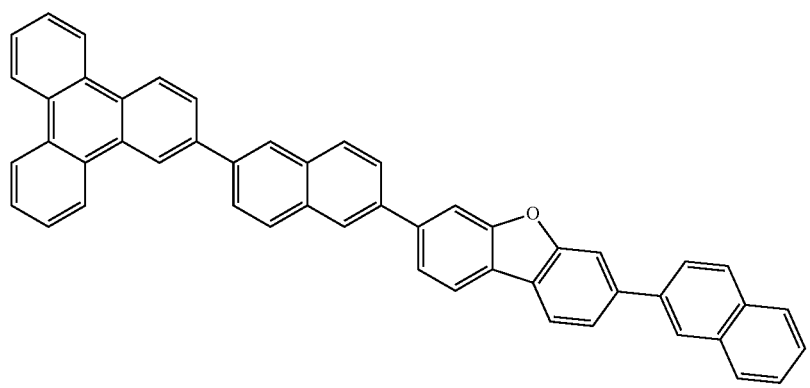
[Sixty-First Chemical Formula]
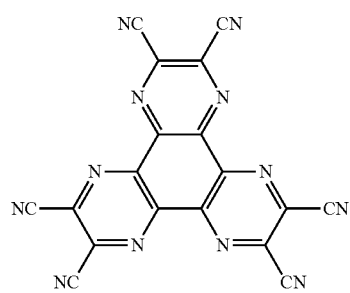
HAT-CN
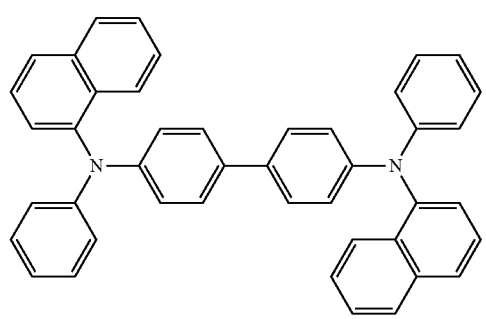
NPD -continued
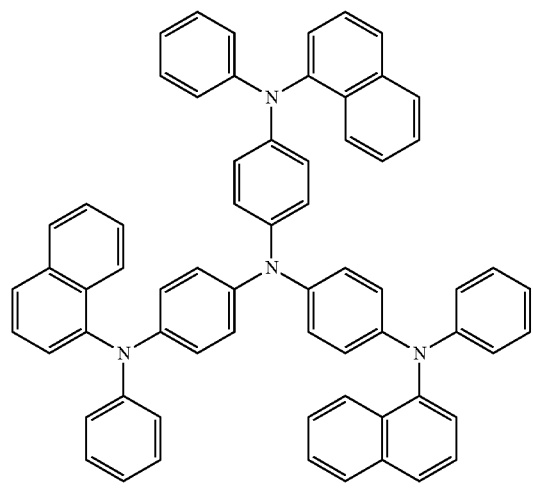
2-TNATA
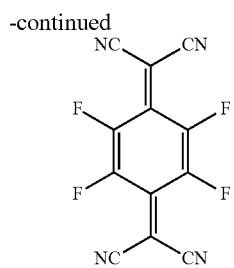
F$_4$-TCNQ
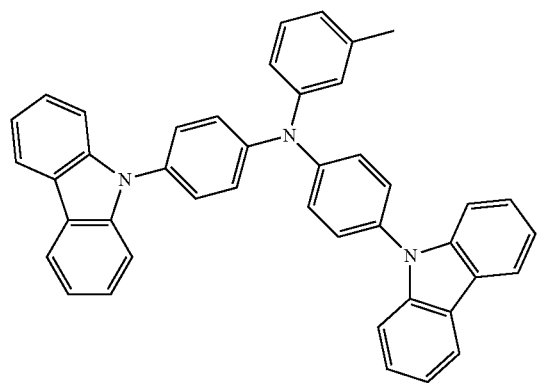
HT-1
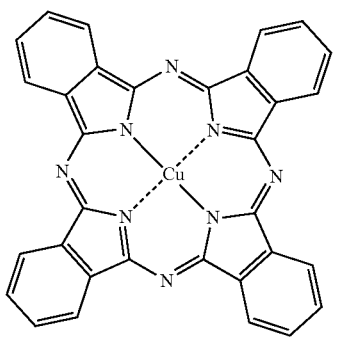
CuPc
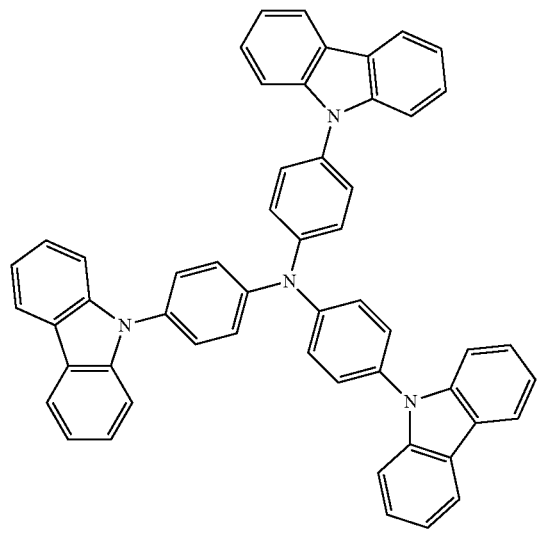
TCTA
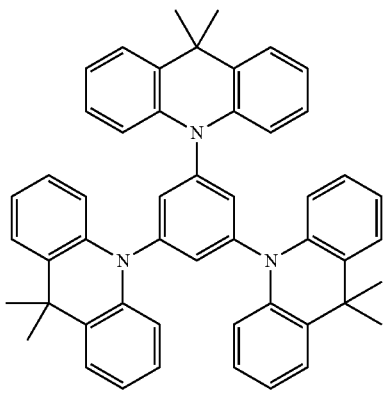
HT-2

-continued
HT-3
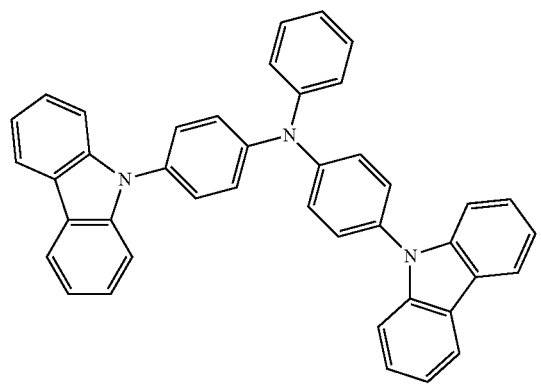
H-1
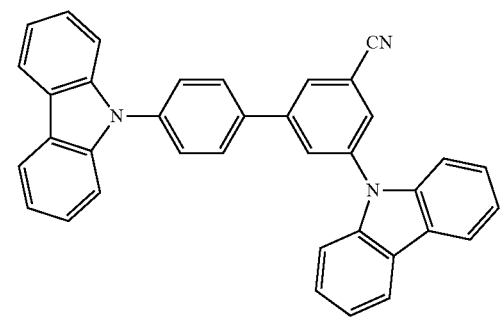
H-2
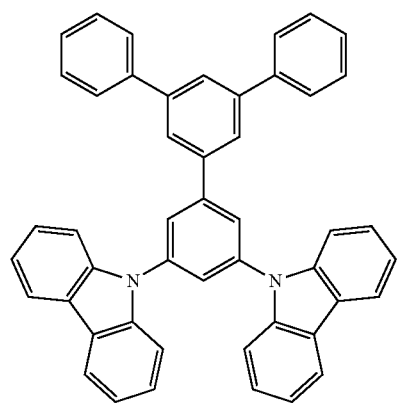
H-3
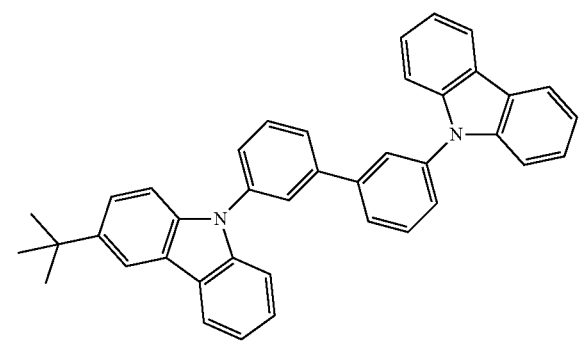
GD-1
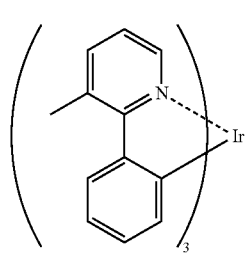
GD-2
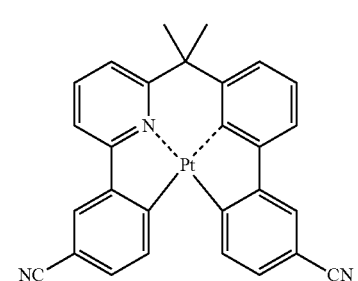
RD-1
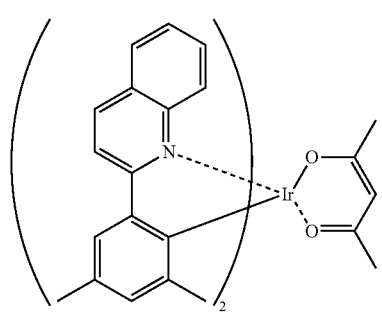
RD-2
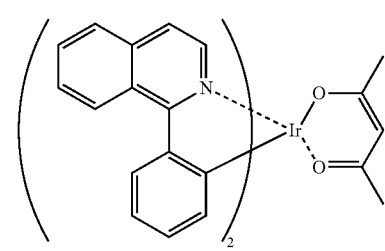

-continued
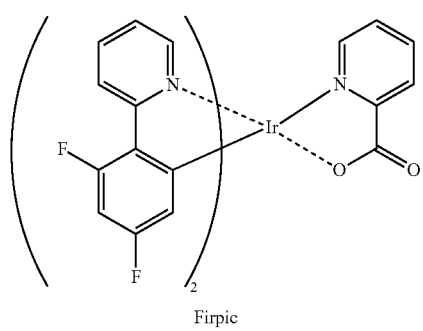
Firpic
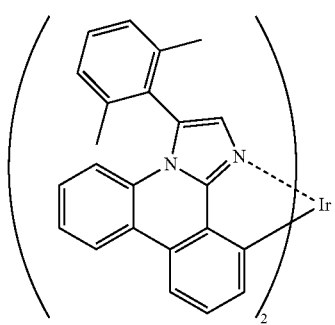
BD-1
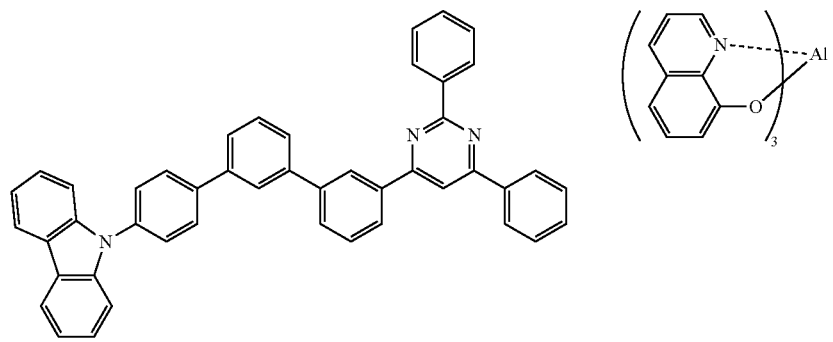
ET-1
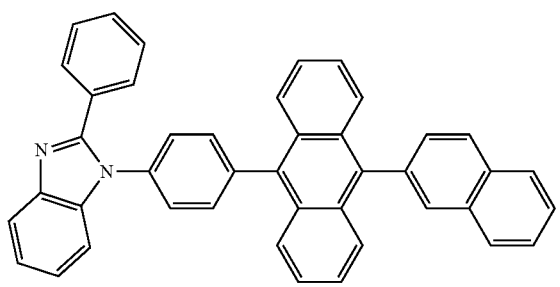
Alq
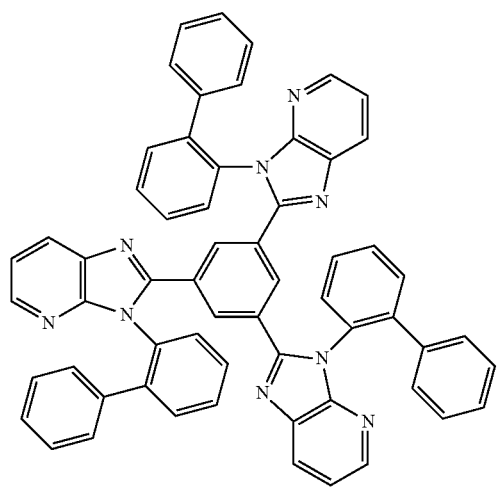
ET-2
ET-3

-continued

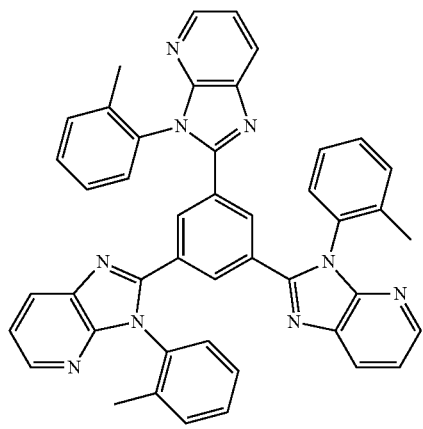

ET-4

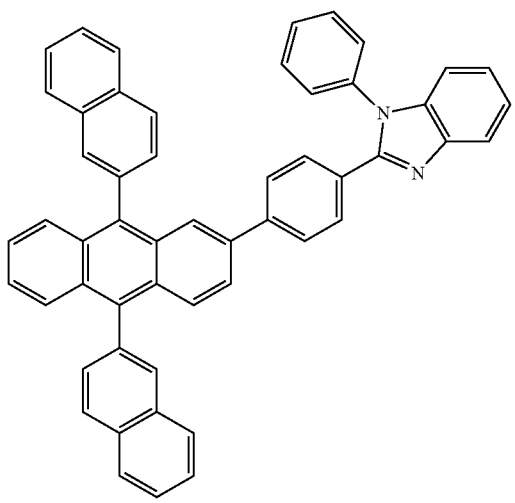

ET-5

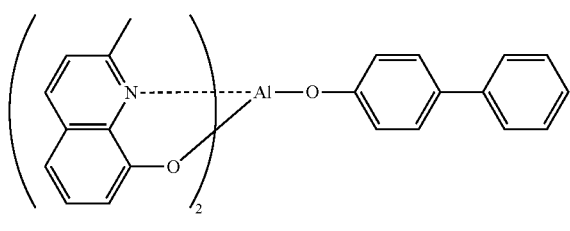

BAlq

DESCRIPTION OF SYMBOLS 2 substrate
3 anode
4 hole injection layer
5 hole transport layer
6 light-emitting layer
7 hole blocking layer
8 electron transport layer
9 cathode
10 organic electroluminescent element
11 organic layer
12 protective layer
14 adhesive layer
16 sealing container
20 light-emitting device
30 light-scattering member
31 transparent substrate
30A light incidence face
30B light emission face
32 microparticles
40 illumination device

The invention claimed is:

1. A charge transport material comprising a compound expressed by General Formula 2 below:

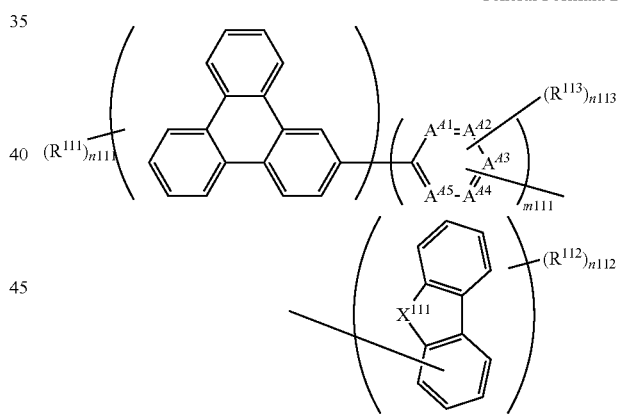

General Formula 2 wherein: $X^{111}$ represents a sulfur atom or an oxygen atom;
$R^{111}$, $R^{112}$, and $R^{113}$ each independently represent an alkyl group, an aryl group selected from the group consisting of phenyl, naphthyl, and phenanthryl, a heteroaryl group, a fluorine atom, or a silyl group, and may further be substituted with an alkyl group, an aryl group, a heteroaryl group, a fluorine atom, or a silyl group;
n111 represents an integer from 0 to 11;
n112 represents an integer from 0 to 2;
n113 represents an integer from 0 to 4;
a plurality of $R^{111}$, $R^{112}$ and $R^{113}$ groups may be the same or different;
$A^{41}$ to $A^{45}$ each independently represent CH, $CR^{113}$, or a nitrogen atom;
m111 represents an integer from 2 to 6;

however, one of $R^{111}$, $R^{112}$, or $R^{113}$ includes a fluorine atom, a fluoroalkyl group, a cycloalkyl group, a silyl group, an alkylsilyl group, or an arylsilyl group; and n111, n112, and n113 are not 0 at the same time;

with the proviso that when $A^{41}$ to $A^{45}$ each represent CH and m111 represents 2 or 3; then one of $R^{111}$, $R^{112}$, or $R^{113}$ is present and includes a silyl group, an alkylsilyl group, an arylsilyl group, or a silicon atom linking group.

2. The charge transport material according to claim 1, wherein m111 in General Formula 2 above is from 2 to 5.

3. The charge transport material according to claim 1, wherein the compound expressed by General Formula 2 above is expressed by General Formula 3 below:

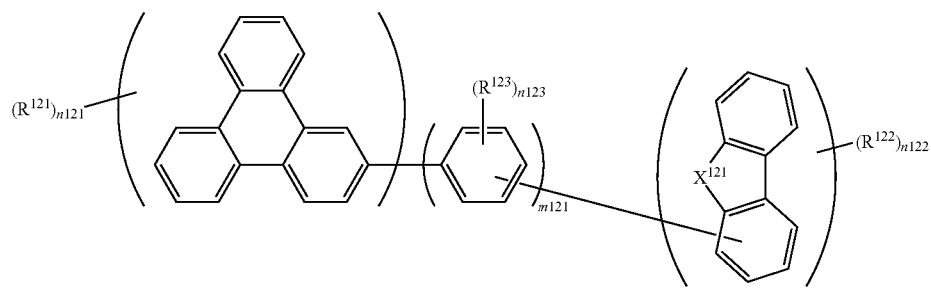

General Formula 3 wherein: $X^{121}$ represents a sulfur atom or an oxygen atom; $R^{121}$, $R^{122}$, and $R^{123}$ each independently represent an alkyl group, an aryl group selected from the group consisting of phenyl, naphthyl, and phenanthryl, a heteroaryl group, a fluorine atom, or a silyl group, and may further be substituted with an alkyl group, an aryl group, a heteroaryl group, a fluorine atom, or a silyl group;

n121 represents an integer from 0 to 11;
n122 represents an integer from 0 to 2;
n123 represents an integer from 0 to 4;
a plurality of $R^{121}$, $R^{122}$, and $R^{123}$ groups may be the same or different;
m121 represents an integer from 2 to 6;
however, one of $R^{121}$, $R^{122}$, or $R^{123}$ includes a fluorine atom, a fluoroalkyl group, a cycloalkyl group, a silyl group, an alkylsilyl group, or an arylsilyl group; and
n121, n122, and n123 are not 0 at the same time
with the proviso that when m121 represents 2, then one of $R^{121}$, $R^{122}$, or $R^{123}$ is present and includes a silyl group, an alkylsilyl group, an arylsilyl group, or a silicon atom linking group.

4. The charge transport material according to claim 1, wherein n111 in General Formula 2 above is 0.

5. The charge transport material according to claim 1, wherein the compound expressed by General Formula 2 above is composed of only carbon atoms and hydrogen atoms, excluding the oxygen atoms and sulfur atoms in the dibenzothiophene skeleton and the dibenzofuran skeleton.

6. The charge transport material according to claim 1, wherein the compound expressed by General Formula 2 above includes a cycloalkyl group.

7. The charge transport material according to claim 1, wherein the molecular weight of the compound expressed by General Formula 2 is 1200 or less.

8. An organic electroluminescent element having
a substrate,
a pair of electrodes that are disposed on this substrate and that include an anode and a cathode, and
an organic layer disposed between said anode and said cathode, wherein said organic layer includes a phosphorescent material and a charge transport material comprising a compound expressed by the charge transport material of claim 1.

9. The organic electroluminescent element according to claim 8, wherein said phosphorescent material is expressed by General Formula E-1 below:

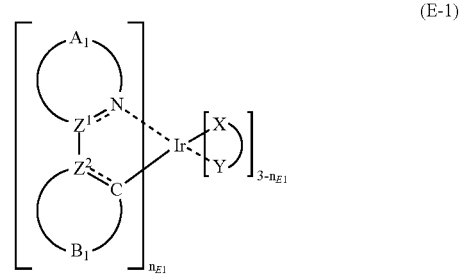

(E-1)

wherein: $Z^1$ and $Z^2$ each independently represent a carbon atom or a nitrogen atom;
$A_1$ represents a group of atoms forming a five- or six-membered heterocycle together with $Z^1$ and the nitrogen atom;
$B_1$ represents a group of atoms forming a five- or six-membered ring together with $Z^2$ and the carbon atom;
(X—Y) represents a monoanionic bidentate ligand; and
$n_{E1}$ represents an integer from 1 to 3.

10. The organic electroluminescent element according to claim 9, wherein the phosphorescent material expressed by General Formula E-1 above is expressed by General Formula E-2 below:

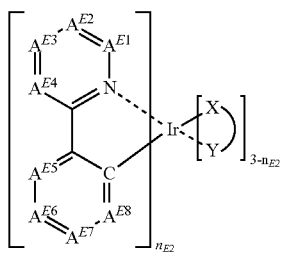

(E-2)

wherein: $A^{E1}$ to $A^{E8}$ each independently represent a nitrogen atom or a carbon atom substituted with $R^E$;

$R^E$ represents a hydrogen atom or a substituent;

(X—Y) represents a monoanionic bidentate ligand; and $n_{E2}$ represents an integer from 1 to 3.

11. The organic electroluminescent element according to claim 9, wherein the maximum emission wavelength of the phosphorescent material expressed by General Formula E-1 above is from 500 to 700 nm.

12. The organic electroluminescent element according to claim 8, wherein said organic layer includes a light-emitting layer containing said phosphorescent material and other organic layers, and said light-emitting layer includes a compound expressed by General Formula 2 above.

13. The organic electroluminescent element according to claim 8, wherein said organic layer includes a light-emitting layer containing said phosphorescent material and other organic layers, said other organic layers include a hole blocking layer disposed between said light-emitting layer and said cathode, and said hole blocking layer contains a compound expressed by General Formula 2 above.

14. A light-emitting device, display device, or illumination device characterized by using the organic electroluminescent element according to claim 8.

15. A charge transport material comprising a compound expressed by General Formula 2 below:

be substituted with an alkyl group, an aryl group, a heteroaryl group, a fluorine atom, or a silyl group;

n111 represents an integer from 0 to 11;

n112 represents an integer from 0 to 2;

n113 represents an integer from 0 to 4;

a plurality of $R^{111}$, $R^{112}$ and $R^{113}$ groups may be the same or different;

$A^{A1}$ to $A^{A5}$ each independently represent CH, $CR^{113}$, or a nitrogen atom;

m111 represents an integer from 4 to 6;

however, one of $R^{111}$, $R^{112}$, or $R^{113}$ includes a fluorine atom, a fluoroalkyl group, a cycloalkyl group, a silyl group, an alkylsilyl group, or an arylsilyl group; and n111, n112, and n113 are not 0 at the same time.

16. An organic electroluminescent element having a substrate, a pair of electrodes that are disposed on this substrate and that include an anode and a cathode, and an organic layer disposed between said anode and said cathode, wherein said organic layer includes a phosphorescent material and a charge transport material comprising a compound expressed by the charge transport material of claim 15.

General Formula 2

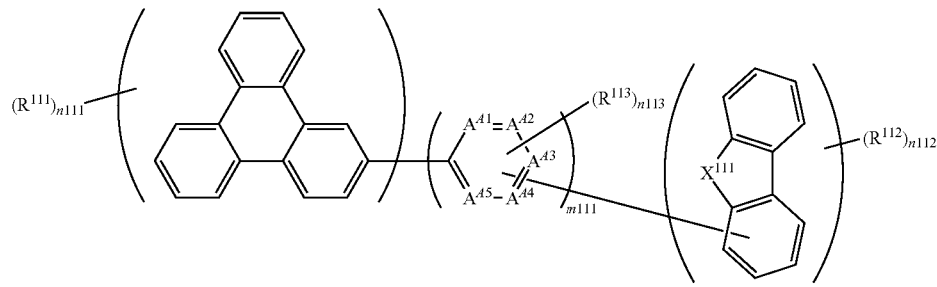

wherein: $X^{111}$ represents a sulfur atom or an oxygen atom;

$R^{111}$, $R^{112}$, and $R^{113}$ each independently represent an alkyl group, an aryl group selected from the group consisting of phenyl, naphthyl, and phenanthryl, a heteroaryl group, a fluorine atom, or a silyl group, and may further 17. The charge transport material of claim 1, wherein when either $A^{A1}$ to $A^{A5}$ each represent CH or m111 represents 2; then one of $R^{111}$, $R^{112}$, or $R^{113}$ is present and includes a silyl group, an alkylsilyl group, an arylsilyl group, or a silicon atom linking group.

* * * * *